United States Patent
Iwasato et al.

(10) Patent No.: US 8,337,812 B2
(45) Date of Patent: Dec. 25, 2012

(54) REGULATOR OF EPHRIN-EPH RECEPTOR SIGNALING AND MOUSE HAVING ABNORMAL EPHRIN-EPH RECEPTOR SIGNALING MECHANISMS

(75) Inventors: Takuji Iwasato, Saitama (JP); Shigeyoshi Itohara, Saitama (JP); Ryosuke Takahashi, Saitama (JP); Haruhisa Inoue, Saitama (JP)

(73) Assignee: RIKEN, Wako-shi (JP)

( * ) Notice: Subject to any disclaimer, the term of this patent is extended or adjusted under 35 U.S.C. 154(b) by 885 days.

(21) Appl. No.: 12/230,016

(22) Filed: Aug. 21, 2008

(65) Prior Publication Data
US 2010/0242126 A1 Sep. 23, 2010

(30) Foreign Application Priority Data
Aug. 23, 2007 (JP) .................................. 2007-217576

(51) Int. Cl.
A61K 49/00 (2006.01)
C12Q 1/00 (2006.01)
G01N 33/53 (2006.01)

(52) U.S. Cl. ................ 424/9.2; 424/9.1; 435/4; 435/7.1

(58) Field of Classification Search .................. None
See application file for complete search history.

(56) References Cited

OTHER PUBLICATIONS

Buttery et al. (2006) The diacylglycerol-binding protein alpha1-chimaerin regulates dendritic morphology. Proc. Natl. Acad. Sci. 103(6): 1924-1929.*

Van de Ven et al. (2005) The nonkinase phorbol ester receptor alphal-chimerin binds the NMDA receptor NR2A subunit and regulates dendritic spine density. J. Neurosci. 25(41): 9488-9496.*

Etienne-Manneville, S., et al., "Rho GTPases in cell biology," Nature, vol. 420, pp. 629-635 (2002).

Luo, L., "Rho GTPases in Neuronal Morphogenesis," Nature Reviews-Neuroscience, vol. 1, pp. 173-180 (2000).

Shamah, S. M., et al., "EphA Receptors Regulate Growth Cone Dynamics through the Novel Guanine Nucleotide Exchange Factor Ephexin," Cell, vol. 105, pp. 233-244 (2001).

Sahin, M., et al., "Eph-Dependent Tyrosine Phosphorylation of Ephexin1 Modulates Growth Cone Collapse," Neuron, vol. 46, pp. 191-204 (2005).

* cited by examiner

*Primary Examiner* — Anne-Marie Falk
(74) *Attorney, Agent, or Firm* — Birch, Stewart, Kolasch & Birch, LLP

(57) ABSTRACT

It is intended to provide an agent for regulating axon extension during neuranagenesis by regulating ephrin-Eph receptor signaling mechanisms and to provide a mouse having abnormal ephrin-Eph receptor signaling mechanisms. The present invention relates to a regulator of axon extension, comprising an agent for promoting or suppressing the function of α-chimerin, and to a miffy (mfy) mouse derived from a B6 strain, which displays autosomal recessive inheritance of an abnormal walking trait exhibiting a hopping gait with left-right synchronized movement of limbs and has mutation in an α-chimerin gene.

7 Claims, 53 Drawing Sheets
(9 of 53 Drawing Sheet(s) Filed in Color)

Tg883:mfy/mfy

Fig. 16

```
AB264771
DEFINITION  Mus musculus Chn1 mRNA for alpha1-chimerin,
complete cds, mutant:
            mfy.
FEATURES          Location/Qualifiers
  source          1..1263
                  /db_xref="taxon:10090"
                  /mol_type="mRNA"
                  /note="mutant: mfy"
                  /organism="Mus musculus"
                  /strain="C57BL/6"
  CDS             317..1147
                  /allele="mfy"
                  /codon_start=1
                  /gene="Chn1"
                  /note="58 aa shorter than wild-type
product"
                  /product="alpha1-chimerin"
                  /transl_table=1
                  /translation=
GAGAGATGCTGCATGCTTTGTATGGTAGCACAGACTGATTTCCTCTGCAGACTCTTAAGT
TTTCAGAAGCTTAAATATAGAGCCCTGTTATAAAAGGAAGAGAGAATTTGTGTGTTAAAT
CGGCCTTGTGAAGAAGTGCTTCATCACTCTCCTGCACCTCCCTGTGCTCTGGTGCGTGGC
GTGGCCACGGCTCTCTAGGTTAGGGCTCGGAGCTGGCTGCAGCATGCTCATGTGCTAGCT
GAGTAGAGTTCACCGGCAGTCGCAGGCTGACACAGGGTTTTTGGTTTTTGTCTTTCTAT
TCCGTTGAATATCAGAATGCCATCCAAAGAGTCTTGGTCGGGGAGGAAAGCTAACAGAGC
CACAGTCCACAAAGCAAAACCCGAGGGCCGGCAGCAAGGCTTACTGATAGCAGCCTTGGG
AATGAAACTGGGCTCTCAAAAGTCATCTGTGACAATCTGGCAACCTCTGAAACTCTTTGC
TTATTCGCAGTTGACATCACTTGTTAGAAGAGCAACTCTGAAAGAAAATGAACAAATTCC
AAAATATGAAAAGGTTCACAATTTCAAGGTGCATACGTTCCGAGGGCCACACTGGTGTGA
ATACTGTGCCAACTTCATGTGGGGCCTCATTGCTCAGGGAGTGAAATGTGCAGGTCTTAA
TTCTGAAGGACTCTACCGAGTGTCAGGATTTAGTGACCTGATTGAAGATGTCAAGATGGC
TTTTGATAGAGATGGTGAGAAGGCGGATATTTCTGTGAACATGTATGAGGACATCAACAT
TATCACTGGTGCACTTAAACTGTACTTCAGGGATCTGCCAATTCCTCTCATCACATACGA
TGCCTACCCCAAGTTCATTGAGTCTGCCAAAATTATGGACCCTGACGAGCAATTGGAGAC
CCTTCACGAAGCACTGAGATCGCTGCCGCCTGCCCACTGCGAGACGCTCCGGTACCTCAT
GGCGCATCTCAAGAGAGTGACCCTTCATGAGAAGGAGAATCTGATGAGTGCAGAGAACCT
TGGGATCGTGTTTGGACCAACCCTCATGAGATCCCCAGAGCTCGACCCCATGGCCGCCCT
GAACGACATACGCTATCAGAGACTGGTGGTGGAGCTGCTTATCAAAAACGAAGACATTTT
ATTTTAGAGTTTTGATTTGAGGAGAAGAAAAATGGTTTACAGATGAAGGAATGTTTTCTA
GTAATTTAATTAGCTTCATTAGCTGAATTGTTTCTTCGTTAGAGGTTTGGCCAAATACCC
AGA
```

Fig. 17

```
AB264772
DEFINITION  Mus musculus Chn1 mRNA for alpha2-chimerin,
complete cds, mutant:
            mfy.
FEATURES             Location/Qualifiers
     source          1..1324
                     /db_xref="taxon:10090"
                     /mol_type="mRNA"
                     /note="mutant: mfy"
                     /organism="Mus musculus"
                     /strain="C57BL/6"
     CDS             3..1208
                     /allele="mfy"
                     /codon_start=1
                     /gene="Chn1"
                     /note="58 aa shorter than wild-type
product"
                     /product="alpha2-chimerin"
                     /transl_table=1
                     /translation="
CCATGGCTCTGACCCTGTTCGATACAGATGAATATAGACCTCCTGTTTGGAAATCTTACT
TATACCAGCTGCAGCAGGAAGCCCCTCACCCTCGAAGGGTCACCTGCACTTGTGAGGTAG
AAAACAGACCAAAGTATTATGGAAGAGAGTATCATGGCATGATCTCTAGAGAAGAGACTG
ACCAGCTCCTGAGTGTGGCTGAGGGGAGCTACCTCATCCGTGAGAGCCAGCGGCAGCCAG
GAACGTACACTTTGGCTTTAAGATTTGGAAGTCAGACCAGAAACTTCAGGCTGTACTACG
ATGGAAAGCACTTTGTTGGGGAGAAACGCTTTGAGTCCATCCACGATCTGGTGACTGATG
GCTTGATTACTCTCTATATTGAAACCAAGGCAGCAGAATACATTGCCAAGATGACGATAA
ACCCAATTTATGAGCACATAGGATACACAACCTTAAACAGAGAGCCAGCATACAAACAGC
ACATGGCAGTCCTGAAAGAGACACATGATGAGAAAGAGGCTACAGGCCAGGATGGGGTAT
CAGAGAAAGGTTGACATCACTTGTTAGAAGAGCAACTCTGAAAGAAAATGAACAAATTC
CAAAATATGAAAAGGTTCACAATTTCAAGGTGCATACGTTCCGAGGGCCACACTGGTGTG
AATACTGTGCCAACTTCATGTGGGGCCTCATTGCTCAGGGAGTGAAATGTGCAGGTCTTA
ATTCTGAAGGACTCTACCGAGTGTCAGGATTTAGTGACCTGATTGAAGATGTCAAGATGG
CTTTTGATAGAGATGGTGAGAAGGCGGATATTTCTGTGAACATGTATGAGGACATCAACA
TTATCACTGGTGCACTTAAACTGTACTTCAGGGATCTGCCAATTCCTCTCATCACATACG
ATGCCTACCCAAGTTCATTGAGTCTGCCAAAATTATGGACCCTGACGAGCAATTGGAGA
CCCTTCACGAAGCACTGAGATCGCTGCCGCCTGCCCACTGCGAGACGCTCCGGTACCTCA
TGGCGCATCTCAAGAGAGTGACCCTTCATGAGAAGGAGAATCTGATGAGTGCAGAGAACC
TTGGGATCGTGTTTGGACCAACCCTCATGAGATCCCCAGAGCTCGACCCCATGGCCGCCC
TGAACGACATACGCTATCAGAGACTGGTGGTGGAGCTGCTTATCAAAAACGAAGACATTT
TATTTAGAGTTTTGATTTGAGGAGAAGAAAAATGGTTTACAGATGAAGGAATGTTTTCT
AGTAATTTAATTAGCTTCATTAGCTGAATTGTTTCTTCGTTAGAGGTTTGGCCAAATACC
CAGA
```

Fig. 18A

```
AB264773
DEFINITION  Mus musculus Chn1 pseudogene mRNA for alpha3-
chimerin, mutant:
            mfy, MT transposon-like element inserted.
FEATURES         Location/Qualifiers
 source          1..3970
                 /db_xref="taxon:10090"
                 /mol_type="mRNA"
                 /note="mutant: mfy"
                 /organism="Mus musculus"
                 /strain="C57BL/6"
 repeat_region   654..2540
                 /note="MT transposon-like element"
                 /note="inserted in Chn1 gene exon 9"
 LTR             654..1048
 LTR             2146..2540
 CDS             join(<2541..2676,3361..3854)
                 /allele="mfy"
                 /gene="Chn1"
                 /note="Intron 9 is not spliced, because of
MT
                 transposon-like element inserted in exon 9"
                 /note="alpha3-chimerin"
                 /pseudo
AGGGCTTTCCTTGCTGTGTCCCCCAGGCAGAAGGTGGAACGTCAGGAGAAGGCAGAAGAG
AAAACCCTCTCCCTTAGGCCTCTTCATAGCACCATTGACCGGTTCATGAGAAGGGACCTA
ACACCTTCCAGAAGGCCTCACCTCTCAGTATGTCATAAGAATTATGAAGAAAACAGACTC
AGATCTTAGCATTGGTGATGTGACATTCTATTATGTGTAATTATTTAACACTTAATAGTT
TTTGTGTAGGGAATCCATCATTTGATTTTGTTTTTGCTTTCTGGGGTCATTTAGGAACTT
AAATAATGAAGCACTAACCAGAATCCTAGCCTTGTTGGGTGTGATGGCACATGCCTTTAA
TTGCAGCATTCAGAGGGCAATGACTGGCAGATATCTAGAGGCCAACCTGGTCTATGTAGA
GAGTTCTGGGTCAGCCAGGGCTACATAGTGAGACCCTATCTCAAAAAGAAAGAAAATCCT
GTCCTAGCTCTAATCAAACTCTCCCAAGAGGAGAGAGCTGATGTTCCTCTCCTTGGAGGA
GCTGCACTTCTGCTGAAAGAAACACTCCAGAAAGCCCAGGCTGGAAATAGTCACGACTTT
TCCTTCATTCTTTTCACAGATTGTGGGTTGAATGTTCACAAGCAGTGTTCCAATTGTCTT
AGTCAGGGTTTCTATTCCTGCACAAACATCATGACCAAGAAGCAAGTTGGGGAGGAAAGG
GTTTATTCGGCTTACACTTCCATACTGCTGTTCATCACCAAGGAAGCCAGGACTGGAACT
CAAGCAGGTCAGGAAACAGGAGCTGATGCAGAGGCCATGGAGGGATGTTCTTTACTGGCT
TGCCTCCCCTGGCTTGCTCAGCCTGCTCTCTTATAAAACCCAAGACTACCAGCCAGGGAT
GGTCTCACCCACAAGGGGCCTTTCCCCCTTGATCACTAATTGAGAAAATGCCTTACAGTT
GGATCTCATGGAGGCATTTCCTCAACAGAAGCTCCTTTCTCTGTGATAACTCCAGCTGTG
TCAAGTTGACACAAAATTAGCCAGTACAATTGACCCCTTGTCAACTTGACACACAAAAAC
ATCACTAGTAAGCCTCAACCCTTACAATCTTATTCATCCCCAAGATCTAAATAACTTTAA
AAGTCCCACAGCCTTTACATATTCTTAAAATTTCAATCTCTTTAAAATATCCATCTCTTT
TAAAATCCAAAGTCTTTTTACAATTAAAAGTCTCTTAACTGTGGGCTCCACTAAAACAGT
```

Fig. 18B

```
TTCTTCCTTCAAGAGGGAAAATATCAGGGCACAGTCACAATCAAAAGCAAAAGTCAATCT
CCAACCGTCCAATGTCTGGGATCCAACTCACGATCTTCTGGGCTCCTCCAAGGGCTTGGG
TAACTTCTCCAGCCAGGCCCTTTGTAGCACACGCATCGTCCTCTAGGCTCCAGATGCCTG
TACCCCACTGCTGCTGCTGCTCTTGGTGGTCATCTCATGGTACTGGCATCTCCAAAACAC
TGCATGACCCCTTCAGTCCTGGGCCTTCAATTGCAACTGAGGCTGCACCTTCACCAATGG
CCTTCCATGGCCTCTCACAGTACCGAACCTCAGCTGCTTTGCGTGACCCCTTCATGCCTT
CAAAACCAGTACCACCTGGGTGACCCTTACATATTACCAAGTCCCACTGCAGCAGGAGTA
CATCCTTGGCCATCTCTGGAACACTGCCTCTTTGTGCTTTCAGAAAACACTTCCCAGAAG
ATGTCACCTCAATGATGCTGGTCTCTTCTTAATCACCGCTAATTTCTTAGCTCCAGCTAA
CCAGCATCAATAGTCCCAGTAATGCAAAGTTTTTGCTTTGGTAGTTCTGGTATCTTGTTA
ATCACAGCTGATTCTTCAGCCCCAGCTAACCAGAACTACAGAATCTTCACAAACAAAACA
GCAATGGCCCTGAAAAGAGTCTTTAATTTTTCCTCTGAAATTTCACAAACCAGAGCTCCA
TCTTCTGCAGTGTTCTCAACATTATCTTCCAAGCTCCTACATGACATCCGACAGAGCTCT
TAACAACGGATGGATCTTCAAGCCCAAAGTTCCAAAGTCCTTCCACAGTCCTCCCCAAAA
CATGGTCAGATTGTCACAGGAATACCCCACTCTGCTGGTACCAATTTGTCTTAGTCAGGG
TTTCTATTCCTGCACAAACATCATGACCAAGAAGCAAGTTGGGGAGGAAAGGGTTTATTC
GGCTTACACTTCCATACTGCTGTTCATCACCAAGGAAGCCAGGACTGGAACTCAAGCAGG
TCAGGAAACAGGAGCTGATGCAGAGGCCATGGAGGGATGTTCTTTACTGGCTTGCCTCCC
CTGGCTTGCTCAGCCTGCTCTCTTATAAAACCCAAGACTACCAGCCAGGGATGGTCTCAC
CCACAAGGGGCCTTTCCCCCTTGATCACTAATTGAGAAAATGCCTTACAGTTGGATCTCA
TGGAGGCATTTCCTCAACAGAAGCTCCTTTCTCTGTGATAACTCCAGCTGTGTCAAGTTG
ACACAAAATTAGCCAGTACAGTCCCCAATGACTGTAAGCCAGATCTGAAGCACGTGAAGA
AGGTGTACAGCTGTGACCTGACAACGCTCGTGAAAGCTCACATCACCAAGCGGCCAATGG
TGGTAGACATGTGCATCAGGGAGATCGAGTCCAGAGGTGAGGTGTTTGGACGAAGGCTGC
CGACGCCTTCACTTGGGGCTCCCTAGGCGCTTGCCTTGTCATTGATGTGGGGAATGGTGT
CAGGAGACGTGTGCTCTCACAGTGCAGTGTATTAATGAGCAAGCAGCTTGATTTCAAGGA
ACATTTAACTGGTGATGGAAAGTAGTATTTAGGATACATTAATGGATGGTGTCTGCAGTC
TGCAAAAATCTCTGGGCAGAGATGTATTCACCTTTCAGGTTTTAAGTTCTTCTCATGCCA
GGACAAAGACAGAAATGCCCTATTAAAACGTCCAGAGCAGAAACCTGAGCCGCACCCTAA
TTATTCTTGCCCCCTTGGGAAAACAGCCATAGGCCTGCTGATGCAGGCTTTCTGTTCTGT
AAAAGACTTTATGATGGAATTGGGTGATGAATGGTCTCCCTTAAGATTTAACATTACTTG
GTCTAATTAGGCAACATGATGGCCAAATTATAAATATCCAGGTGACAGTAGGTCAGAAGT
AAAAATTGTGGAACAGATTCACTTTTGGAGGATGTGGGAGAAGACTTCTAGGCATGTGTG
TTTTTTCTAACACATCGTTTGTCCAGCTTGAAGTATGGAGAGATGTTGAAATGAGAAGGA
AAGTCATGAGTTAACAGAAAAGTAGTTCCCATGCTTCATTCATTCATTCATTTTTTTCAG
GTCTTAATTCTGAAGGACTCTACCGAGTGTCAGGATTTAGTGACCTGATTGAAGATGTCA
AGATGGCTTTTGATAGAGATGGTGAGAAGGCGGATATTTCTGTGAACATGTATGAGGACA
TCAACATTATCACTGGTGCACTTAAACTGTACTTCAGGGATCTGCCAATTCCTCTCATCA
CATACGATGCCTACCCCAAGTTCATTGAGTCTGCCAAAATTATGGACCCTGACGAGCAAT
GGAGACCCTTCACGAAGCACTGAGATCGCTGCCGCCTGCCCACTGCGAGACGCTCCGGT
ACCTCATGGCGCATCTCAAGAGAGTGACCCTTCATGAGAAGGAGAATCTGATGAGTGCAG
AGAACCTTGGGATCGTGTTTGGACCAACCCTCATGAGATCCCCAGAGCTCGACCCCATGG
CCGCCCTGAACGACATACGCTATCAGAGACTGGTGGTGGAGCTGCTTATCAAAAACGAAG
ACATTTATTTTAGAGTTTTGATTTGAGGAGAAGAAAAATGGTTTACAGATGAAGGAATG
TTTTCTAGTAATTTAATTAGCTTCATTAGCTGAATTGTTTCTTCGTTAGAGGTTTGGCCA
AATACCCAGA
```

Fig. 19

```
AB264774
DEFINITION  Mus musculus Chn1 mRNA for alpha3-chimerin,
complete cds, wild
            type.
FEATURES         Location/Qualifiers
  source         1..1403
                 /db_xref="taxon:10090"
                 /mol_type="mRNA"
                 /note="wild type"
                 /organism="Mus musculus"
                 /strain="C57BL/6"
  CDS            655..1287
                 /codon_start=1
                 /gene="Chn1"
                 /note="wild type"
                 /product="alpha3-chimerin"
                 /transl_table=1
                 /translation="
AGGGCTTTCCTTGCTGTGTCCCCCAGGCAGAAGGTGGAACGTCAGGAGAAGGCAGAAGAG
AAAACCCTCTCCCTTAGGCCTCTTCATAGCACCATTGACCGGTTCATGAGAAGGGACCTA
ACACCTTCCAGAAGGCCTCACCTCTCAGTATGTCATAAGAATTATGAAGAAAACAGACTC
AGATCTTAGCATTGGTGATGTGACATTCTATTATGTGTAATTATTTAACACTTAATAGTT
TTTGTGTAGGGAATCCATCATTTGATTTTGTTTTTGCTTTCTGGGGTCATTTAGGAACTT
AAATAATGAAGCACTAACCAGAATCCTAGCCTTGTTGGGTGTGATGGCACATGCCTTTAA
TTGCAGCATTCAGAGGGCAATGACTGGCAGATATCTAGAGGCCAACCTGGTCTATGTAGA
GAGTTCTGGGTCAGCCAGGGCTACATAGTGAGACCCTATCTCAAAAAGAAAGAAAATCCT
GTCCTAGCTCTAATCAAACTCTCCCAAGAGGAGAGAGCTGATGTTCCTCTCCTTGGAGGA
GCTGCACTTCTGCTGAAAGAAACACTCCAGAAAGCCCAGGCTGGAAATAGTCACGACTTT
TCCTTCATTCTTTTCACAGATTGTGGGTTGAATGTTCACAAGCAGTGTTCCAAGATGGTC
CCCAATGACTGTAAGCCAGATCTGAAGCACGTGAAGAAGGTGTACAGCTGTGACCTGACA
ACGCTCGTGAAAGCTCACATCACCAAGCGGCCAATGGTGGTAGACATGTGCATCAGGGAG
ATCGAGTCCAGAGGTCTTAATTCTGAAGGACTCTACCGAGTGTCAGGATTTAGTGACCTG
ATTGAAGATGTCAAGATGGCTTTTGATAGAGATGGTGAGAAGGCGGATATTTCTGTGAAC
ATGTATGAGGACATCAACATTATCACTGGTGCACTTAAACTGTACTTCAGGGATCTGCCA
ATTCCTCTCATCACATACGATGCCTACCCCAAGTTCATTGAGTCTGCCAAAATTATGGAC
CCTGACGAGCAATTGGAGACCCTTCACGAAGCACTGAGATCGCTGCCGCCTGCCCACTGC
GAGACGCTCCGGTACCTCATGGCGCATCTCAAGAGAGTGACCCTTCATGAAGGAGAAT
CTGATGAGTGCAGAGAACCTTGGGATCGTGTTTGGACCAACCCTCATGAGATCCCCAGAG
CTCGACCCCATGGCCGCCCTGAACGACATACGCTATCAGAGACTGGTGGTGGAGCTGCTT
ATCAAAAACGAAGACATTTTATTTTAGAGTTTTGATTTGAGGAGAAGAAAAATGGTTTAC
AGATGAAGGAATGTTTTCTAGTAATTTAATTAGCTTCATTAGCTGAATTGTTTCTTCGTT
AGAGGTTTGGCCAAATACCCAGA
```

Fig. 20A

```
AB264775
DEFINITION  Mus musculus DNA, MT transposon-like element
inserted in Chn1 gene
            exon 9.
FEATURES             Location/Qualifiers
  source             1..2770
                     /db_xref="taxon:10090"
                     /mol_type="genomic DNA"
                     /note="mutant: mfy"
                     /organism="Mus musculus"
                     /strain="C57BL/6"
  exon               1..>653
                     /allele="mfy"
                     /gene="Chn1"
                     /note="alpha3-chimerin"
                     /number=9a
                     /pseudo
  exon               620..>653
                     /allele="mfy"
                     /gene="Chn1"
                     /note="alpha1-chimerin and alpha2-chimerin"
                     /number=9b
                     /pseudo
  repeat_region      654..2540
                     /note="MT transposon-like element"
                     /note="inserted in Chn1 gene exon 9"
  LTR                654..1048
  LTR                2146..2540
  exon               <2541..2676
                     /allele="mfy"
                     /gene="Chn1"
                     /note="alpha1-chimerin, alpha2-chimerin and
                     alpha3-chimerin"
                     /number=9
                     /pseudo
AGGGCTTTCCTTGCTGTGTCCCCCAGGCAGAAGGTGGAACGTCAGGAGAAGGCAGAAGAG
AAAACCCTCTCCCTTAGGCCTCTTCATAGCACCATTGACCGGTTCATGAGAAGGGACCTA
ACACCTTCCAGAAGGCCTCACCTCTCAGTATGTCATAAGAATTATGAAGAAAACAGACTC
AGATCTTAGCATTGGTGATGTGACATTCTATTATGTGTAATTATTTAACACTTAATAGTT
TTTGTGTAGGGAATCCATCATTTGATTTTGTTTTTGCTTTCTGGGGTCATTTAGGAACTT
AAATAATGAAGCACTAACCAGAATCCTAGCCTTGTTGGGTGTGATGGCACATGCCTTTAA
TTGCAGCATTCAGAGGGCAATGACTGGCAGATATCTAGAGGCCAACCTGGTCTATGTAGA
GAGTTCTGGGTCAGCCAGGGCTACATAGTGAGACCCTATCTCAAAAAGAAAGAAAATCCT
GTCCTAGCTCTAATCAAACTCTCCCAAGAGGAGAGAGCTGATGTTCCTCTCCTTGGAGGA
GCTGCACTTCTGCTGAAAGAAACACTCCAGAAAGCCCAGGCTGGAAATAGTCACGACTTT
```

Fig. 20B

```
TCCTTCATTCTTTTCACAGATTGTGGGTTGAATGTTCACAAGCAGTGTTCCAATTGTCTT
AGTCAGGGTTTCTATTCCTGCACAAACATCATGACCAAGAAGCAAGTTGGGGAGGAAAGG
GTTTATTCGGCTTACACTTCCATACTGCTGTTCATCACCAAGGAAGCCAGGACTGGAACT
CAAGCAGGTCAGGAAACAGGAGCTGATGCAGAGGCCATGGAGGGATGTTCTTTACTGGCT
TGCCTCCCCTGGCTTGCTCAGCCTGCTCTCTTATAAACCCAAGACTACCAGCCAGGGAT
GGTCTCACCCACAAGGGGCCTTTCCCCCTTGATCACTAATTGAGAAAATGCCTTACAGTT
GGATCTCATGGAGGCATTTCCTCAACAGAAGCTCCTTTCTCTGTGATAACTCCAGCTGTG
TCAAGTTGACACAAAATTAGCCAGTACAATTGACCCCTTGTCAACTTGACACACAAAAAC
ATCACTAGTAAGCCTCAACCCTTACAATCTTATTCATCCCAAGATCTAAATAACTTTAA
AAGTCCCACAGCCTTTACATATTCTTAAAATTTCAATCTCTTTAAAATATCCATCTCTTT
TAAAATCCAAAGTCTTTTTACAATTAAAAGTCTCTTAACTGTGGGCTCCACTAAAACAGT
TTCTTCCTTCAAGAGGGAAAATATCAGGGCACAGTCACAATCAAAAGCAAAAGTCAATCT
CCAACCGTCCAATGTCTGGGATCCAACTCACGATCTTCTGGGCTCCTCCAAGGGCTTGGG
TAACTTCTCCAGCCAGGCCCTTTGTAGCACACGCATCGTCCTCTAGGCTCCAGATGCCTG
TACCCCACTGCTGCTGCTGCTCTTGGTGGTCATCTCATGGTACTGGCATCTCCAAAACAC
TGCATGACCCCTTCAGTCCTGGGCCTTCAATTGCAACTGAGGCTGCACCTTCACCAATGG
CCTTCCATGGCCTCTCACAGTACCGAACCTCAGCTGCTTTGCGTGACCCCTTCATGCCTT
CAAAACCAGTACCACCTGGGTGACCCTTACATATTACCAAGTCCCACTGCAGCAGGAGTA
CATCCTTGGCCATCTCTGGAACACTGCCTCTTTGTGCTTTCAGAAAACACTTCCCAGAAG
ATGTCACCTCAATGATGCTGGTCTCTTCTTAATCACCGCTAATTTCTTAGCTCCAGCTAA
CCAGCATCAATAGTCCCAGTAATGCAAAGTTTTTGCTTTGGTAGTTCTGGTATCCTGTTA
ATCACAGCTGATTCTTCAGCCCCAGCTAACCAGAACTACAGAATCTTCACAAACAAAACA
GCAATGGCCCTGAAAAGAGTCTTTAATTTTTCCTCTGAAATTTCACAGACCAGAGCTCCA
TCTTCTGCAGTGTTCTCAACATTATCTTCCAAGCTCCTACATGACATCCGACAGAGCTCT
TAACAACGGATGGATCTTCAAGCCCAAAGTTCCAAAGTCCTTCCACAGTCCTCCCCAAAA
CATGGTCAGATTGTCACAGGAATACCCCACTCTGCTGGTACCAATTTGTCTTAGTCAGGG
TTTCTATTCCTGCACAAACATCATGACCAAGAAGCAAGTTGGGGAGGAAAGGGTTTATTC
GGCTTACACTTCCATACTGCTGCTCATCACCAAGGAAGCCAGGACTGGAACTCAAGCAGG
TCAGGAAACAGGAGCTGATGCAGAGGCCATGGAGGGATGTTCTTTACTGGCTTGCCTCCC
CTGGCTTGCTCAGCCTGCTCTCTTATAAACCCAAGACTACCAGCCAGGGATGGTCTCAC
CCACAAGGGGCCTTTCCCCCTTGATCACTAATTGAGAAAATGCCTTACAGTTGGATCTCA
TGGAGGCATTTCCTCAACAGAAGCTCCTTTCTCTGTGATAACTCCAGCTGTGTCAAGTTG
ACACAAAATTAGCCAGTACAGTCCCAATGACTGTAAGCCAGATCTGAAGCACGTGAAGA
AGGTGTACAGCTGTGACCTGACAACGCTCGTGAAAGCTCACATCACCAAGCGGCCAATGG
TGGTAGACATGTGCATCAGGGAGATCGAGTCCAGAGGTGAGGTGTTTGGACGAAGGCTGC
CGACGCCTTCACTTGGGGCTCCCTAGGCGCTTGCCTTGTCATTGATGTGGGGAATGGTGT
CAGGAGACGT
```

REGULATOR OF EPHRIN-EPH RECEPTOR SIGNALING AND MOUSE HAVING ABNORMAL EPHRIN-EPH RECEPTOR SIGNALING MECHANISMS

BACKGROUND OF THE INVENTION

1. Field of the Invention

The present invention relates to the regulation of ephrin-Eph receptor signaling mechanisms. Particularly, the present invention relates to the regulation of ephrinB3-EphA4 signaling mechanisms by targeting α-chimerin (α-chimaerin) in the signaling mechanisms.

2. Background Art

Ephrins are cell surface-bound proteins and are ligands for Eph receptors. Ephrin/Eph binding induces bidirectional signaling (see Noren, N. K. et al., (2004) Cell Signal. 16, 655-666 and Palmer, A. et al, (2003) Genes Dev. 17, 1429-1450). Ephrin/Eph signaling, which functions in short-range cell-to-cell communication usually through repulsive effects, plays a central role in neuronal circuit formation (see Palmer, A. et al, (2003) Genes Dev. 17, 1429-1450, Flanagan, J. G. et al., (1998) Annu. Rev. Neurosci. 21, 309-345, and Pasquale, E. B. (2005), Nat. Rev. Mol. Cell Biol. 6, 462-475). Downstream signaling mechanisms have been studied mostly through cell culture experiments. Particularly, important players are the Rho-family GTPases (Rho-GTPases), such as RhoA, Rac, and Cdc42, which are the key regulators of actin dynamics (see Noren, N. K. et al., (2004) Cell Signal. 16, 655-666, Etienne-Manneville, S. et al., (2002) Nature 420, 629-635, Luo, L. (2000), Nat. Rev. Neurosci. 1, 173-180, and Wahl, S. et al, (2000) J. Cell Biol. 149, 263-270). Rho-GTPases are directly activated by Rho-guanine nucleotide-exchange factors (Rho-GEFs) and are inactivated by Rho-GTPase-activating proteins (Rho-GAPs). Reports in recent years suggest that ephrin/Eph regulates Rho-GTPases via Rho-GEFs (see Cowan, C. W. et al., (2005) Neuron 46, 205-217, Irie, F. et al., (2002) Nat. Neurosci. 5, 1117-1118, Murai, K. K. et al., (2005) Neuron 46, 161-163, Ogita, H. et al., (2003) Circ. Res. 93, 23-31, Penzes, P. et al., (2003) Neuron 37, 263-274, Shamah, S. M. et al., (2001) Cell 105, 233-244, and Tanaka, M. et al., (2004) EMBO J. 23, 1075-1088). Among the numerous Rho-GEFs allegedly involved in ephrin/Eph, ephexin1 has been most studied. EphA receptors regulate growth-cone dynamics via ephexin1 in axon guidance (see Shamah, S. M. et al., (2001) Cell 105, 233-244 and Sahin, M. et al., (2005) Neuron 46, 191-204). In in vitro experiments, activation of RhoA induces growth-cone retraction, while activation of Rac and Cdc42 induces its extension (see Etienne-Manneville, S. et al., (2002) Nature 420, 629-635 and Luo, L. (2000), Nat. Rev. Neurosci. 1, 173-180). The binding of Eph and ephrin leads to activation of the GEF activity of ephexin1 towards RhoA, thereby causing growth-cone collapse (see Shamah, S. M. et al., (2001) Cell 105, 233-244). However, as ephexin1-knockout (KO) mice are normal (see Sahin, M. et al., (2005) Neuron 46, 191-204), the function of ephexin1 in vivo remains unknown. It is also noteworthy that, compared with the considerable attention given to Rho-GEFs, the possible involvement of Rho-GAPs in actin dynamics regulated by ephrin/Eph has been neglected.

The roles of ephrin/Eph in vivo have been studied using mouse reverse genetics. Particularly, ephrinB3→EphA4 forward signaling is extremely well-characterized. EphrinB3-KO and EphA4-KO mice have many common phenotypes, including a rabbit-like gait and abnormality in two major motor circuits: the corticospinal tract and the central pattern generator (CPG). Similar phenotypes are also displayed by EphA4$^{KD/KD}$ and EphA4$^{FF/FF}$ mice having the kinase activity of EphA4, but not by mice having ephrinB3 lacking its cytoplasmic domain (see Dottori, M. et al., (1998) Proc. Natl. Acad. Sci. USA 95, 13248-13253, Kullander, K. et al., (2003). Science 299, 1889-1892, Kullander, K. et al., (2001). Genes Dev. 15, 877-888, Kullander, K. et al., (2001) Neuron 29, 73-84, and Yokoyama, N. et al., (2001) Neuron 29, 85-97). Thus, it is apparent that ephrinB3→EphA forward signaling, but not EphA4→ephrinB3 reverse signaling, is essential for the formation of these motor circuits. CST axons, which regulate voluntary movements, arise from the motor cortex, then cross the midline at the medulla, and descend the contralateral spinal cord (see Giamino, S. et al., (1999) Brain Res. Dev. Brain Res. 112, 189-204 and Liang, F. Y. et al., (1991) J. Comp. Neurol. 311, 356-366). In wild-type mice, CST axons rarely cross back the midline (i.e., re-cross the midline) in the spinal cord, because ephrinB3 is anchored at the midline and transmits repulsive signals via EphA4 expressed on CST axon surface. In ephrinB3- or EphA4-knockout mice, due to a lack of repulsive ephrinB3/EphA4 forward signaling, many CST axons fail to stop at the midline and re-cross it (see Kullander, K. et al., (2001). Genes Dev. 15, 877-888 and Yokoyama, N. et al., (2001) Neuron 29, 85-97). Spinal CPGs are thought to generate left-right alternate stepping of limbs during walking (see Grillner, S. et al., (1985) Annu. Rev. Neurosci. 8, 233-261). Locomotor-like rhythmic activity alternating between the left and right sides can be induced in isolated wild-type spinal cords (see Nishimaru, H. et al., (2006) J. Neurosci. 26, 5320-5328), whereas the rhythmic activity of the two sides is synchronous in ephrinB3- or EphA4-knockout mice (see Kullander, K. et al., (2003). Science 299, 1889-1892). Aberrantly frequent midline crossing of EphA4-expressing CPG interneurons is thought to be responsible for such abnormality in the knockout mice (see Kullander, K. et al., (2003). Science 299, 1889-1892 and Kiehn, O., et al., (2004) Neuron 41, 317-321).

SUMMARY OF THE INVENTION

An object of the present invention is to provide an agent for regulating axon extension during neuranagenesis by regulating ephrin-Eph receptor signaling mechanisms and to provide a mouse having abnormal ephrin-Eph receptor signaling mechanisms.

The ephrin/Eph system plays a central role in neuronal circuit formation. However, its downstream mechanisms are poorly understood. The present inventor has found that a Rac-specific GTPase-activating protein (GAP) α-chimerin (α-type chimerin) mediates ephrinB3/EphA4 forward signaling.

The present inventor found a mutant mouse having a rabbit-like hopping gait with left-right synchronized movement of limbs, in the course of sib mating of mice, and designated the mutant mouse as "miffy (mfy)". In mfy mice, abnormality was detected in corticospinal tract and spinal central pattern generator axons. Using positional cloning, rescue with transgenic mice, and gene targeting, the present inventor found that miffy is novel recessive mutation, that is, disruption of α-chimerin is responsible for the mfy phenotype. The present inventor established a mfy mouse strain.

The present inventor analyzed the corticospinal tract using mfy. In wild-type mice, the right brain controls movements in the left side of the body, while the left brain controls movements in the right side of the body. Axons extending from the left and right cerebral motor cortexes cross the midline at the medulla, then descend the white matter in the contralateral spinal cord, and enter the grey matter at their respective required sites. Then, they form direct or indirect synaptic connection with peripheral motor neurons that regulate muscle movement. In this process, once the axons cross the spinal cord midline, they are prevented from crossing back (i.e., re-crossing) the midline. The present inventor analyzed the corticospinal tract of mfy using a tracer and consequently found that many axons re-cross the spinal cord midline.

The present inventor further analyzed spinal local circuits. The present inventor analyzed central pattern generator (CPG) circuits using a tracer and consequently found that many axons re-cross the spinal cord midline of mfy.

Using positional cloning, the present inventor found that α-chimerin genes belonging to the Rho-GAP (Rho-family inactivator) family are nonfunctional in mfy. Thus, the present inventor prepared α-chimerin-knockout mice and analyzed their behaviors. As a result, it was found that the knockout mice exhibit abnormal walking and abnormal circuits similar to those in mfy mice, demonstrating that α-chimerin is the causal gene of the mfy mutation.

The present inventor further studied signaling mechanisms using approaches such as biochemical analysis, cell culture analysis, and immunostaining. When EphA4 present on the growth cone surface of motor neurons recognizes ephrinB3 at the spinal cord midline, α-chimerin bound with EphA4 in the growth cones is activated. The activated α-chimerin suppresses the function of Rac. As the Rac protein functions to promote growth-cone extension, suppression of its function prevents growth-cone extension. In mfy, both ephrinB3 and EphA4 are normal, but the growth cones fail to stop due to a lack of α-chimerin, thereby causing midline re-crossing of the neurons. Therefore, abnormal walking exhibiting a hopping gait is caused.

The mfy phenotype is similar to those of EphA4- and ephrinB3-knockout mice. α-chimerin binds with EphA4 and inactivates Rac, a positive regulator of process outgrowth, in response to ephrinB3/EphA4 signaling. Furthermore, suppression of α-chimerin expression suppresses ephrinB3-induced growth-cone collapse.

The present inventor found for the first time that signaling prevents growth-cone extension via α-chimerin-induced Rac inactivation in motor neuronal circuit formation, that Rho-family GAPs play a key role in ephrin/Eph signaling, and that a Rac-specific GAP α-chimerin plays an essential role as a downstream mediator of ephrinB3/EphA4 forward signaling in CST and CPG formation.

The present inventor completed the present invention based on these findings.

Specifically, the present invention is as follows:

[1] A regulator of axon extension, comprising an agent for promoting or suppressing the function of α-chimerin.

[2] The regulator of axon extension according to [1], wherein the agent for promoting the function of α-chimerin is a DNA encoding α-chimerin.

[3] The regulator of axon extension according to [1], wherein the agent for suppressing the function of α-chimerin is an anti-α-chimerin antibody or a double-stranded RNA suppressing expression of α-chimerin through RNA interference.

[4] A method for screening a therapeutic drug for ephrin/Eph-associated disease, comprising administering candidate agents to a cell or an animal and selecting a therapeutic drug among the agents depending on whether or not each of the agents acts on Rho-GAP and regulates a series of ephrin/Eph signaling that inactivates a member of low-molecular-weight G proteins of the Rho-family via Rho-GAP.

[5] A miffy (mfy) mouse derived from a B6 strain, which displays autosomal recessive inheritance of an abnormal walking trait exhibiting a hopping gait with left-right synchronized movement of limbs and has mutation in an α-chimerin gene.

[6] The mfy mouse according to [5], which further has the features: (1) in the spinal cord, the white matter in the dorsal funiculus is reduced; and (2) CST axons re-cross the spinal cord midline.

[7] The mfy mouse according to [5] or [6], wherein the mutation in the α-chimerin gene is retroposon insertion into exon 9 of the α-chimerin gene.

[8] An α-chimerin-knockout mouse, which has the feature that the mouse has abnormal walking exhibiting a hopping gait with left-right synchronized movement of limbs.

[9] A method for screening a regulator of axon extension, comprising administering candidate agents to a cell or an animal and selecting a regulator of axon extension among the agents depending on whether or not each of the agents regulates the interaction between EphA4 and α-chimerin, compared with the case where the agent is not administered.

The agent for promoting or suppressing the function of α-chimerin according to the present invention can normally regulate axon extension during neuronal circuit formation. Moreover, the mouse of the present invention having the feature that the mouse has abnormal walking exhibiting a hopping gait with left-right synchronized movement of limbs can be used for, for example, elucidating ephrin-Eph receptor signaling mechanisms.

The patent or application file contains at least one drawing executed in color. Copies of this patent or patent application publication with color drawing(s) will be provided by the office upon request and payment of the necessary fee.

BRIEF DESCRIPTION OF THE DRAWINGS

FIG. 16 is a diagram showing sequence information on α1-Chn$^{mfy}$ cDNA.

FIG. 17 is a diagram showing sequence information on α2-Chn$^{mfy}$ cDNA.

FIG. 18A is a diagram showing sequence information on α3-Chn$^{mfy}$ cDNA.

FIG. 18B is a diagram showing sequence information on α3-Chn$^{mfy}$ cDNA (continued from FIG. 18A).

FIG. 19 is a diagram showing sequence information on α3-Chn$^{WT}$ cDNA.

FIG. 20A is a diagram showing sequence information of retroposon.

FIG. 20B a diagram showing sequence information of retroposon (continued from FIG. 20A).

DETAILED DESCRIPTION OF THE PREFERRED EMBODIMENTS

Figure 1A:
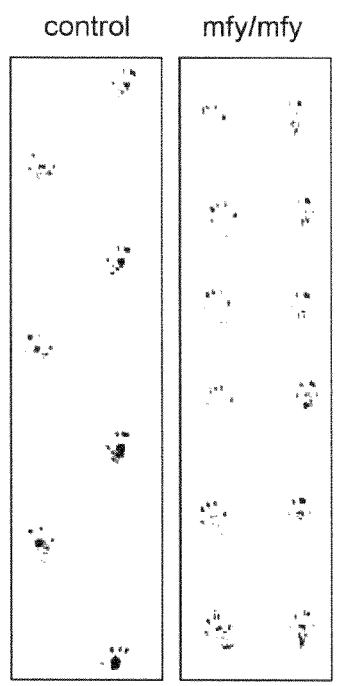
FIG. 1A is a diagram showing hind-limb footprint patterns of miffy (mfy).

Hereinafter, the present invention will be described in detail.

Low-molecular-weight G proteins of the Rho family are a molecular group that plays a key role in regulating actin cytoskeleton. They are activated by Rho-GEFs and inactivated by Rho-GAPs. Members of the family include RhoA, Rac1, and Cdc42. Chimerins, which are proteins belonging to Rho-GAPs, interact with members of low-molecular-weight G proteins of the Rho family and inactivate the members. For example, α-chimerin, a species of Rho-GAP, specifically interacts with Rac and inactivates it.

In in vivo neuronal circuit formation, ephrins bind with their receptors Ephs and transmit signals. For example, ephrinB3 binds with EphA4 and transmits signals to the EphA4. The signals are further transmitted to α-chimerin to activate it. The activated α-chimerin inactivates Rac. Specifically, α-chimerin can regulate ephrin-Eph signaling such that α-chimerin-mediated ephrinB3→EphA4 signaling reaches Rac and inactivates it.

In formation of neuronal circuits that regulate the left-right movement of the animal body, EphA4 receptors are expressed on the surface of growth cones at the tips of axons, while ephrinB3, a ligand for EphA4, is anchored at the spinal cord midline to form walls. When the growth cones come to the midline, ephrinB3 binds with EphA4 and induces signals to the EphA4. The signals inactivate Rac via α-chimerin and suppress growth-cone extension at the tips of axons. Thus, the axons do not extend over the midline.

Thus, neuronal extension and growth can be regulated by regulating α-chimerin-mediated ephrinB3→EphA4 signaling that reaches Rac and inactivates it. For the regulation of the signaling, for example, the action of α-chimerin may be regulated.

For example, nerve injuries such as spinal cord injury can possibly be treated by applying regenerative medicine. Specifically, nerves can be regenerated by utilizing neural stem cells or by promoting axon extension. Axons extending from the left and right cerebral motor cortexes cross the midline at the medulla, then descend the white matter in the contralateral spinal cord, and enter the grey matter at their respective required sites. Then, they form direct or indirect synaptic connection with peripheral motor neurons that regulate muscle movement. The axons once crossing the spinal cord midline extend over the midline, thereby causing midline re-crossing. Thus, regeneration of axons requires regulating axon extension such that the axons are initially allowed to extend over the midline at the medulla and, once crossing the midline, are prevented from crossing back the midline. For this purpose, it is effective to regulate growth-cone extension of neurons.

Thus, growth-cone extension at the tips of axons is suppressed by promoting inactivation of Rac through activation of α-chimerin during neuranagenesis. As a result, midline re-crossing can be prevented. On the other hand, growth-cone extension is promoted by suppressing inactivation of Rac through inactivation of α-chimerin. As a result, the axons can extend over the spinal cord midline.

For the activation of α-chimerin, for example, a gene encoding α-chimerin is forcedly expressed after transduction. Alternatively, an agent for activating α-chimerin may be administered. On the other hand, for the inactivation of α-chimerin, an α-chimerin-targeting agent that suppresses the action of α-chimerin or suppresses its expression may be administered.

The agent for activating α-chimerin or promoting the function of α-chimerin can be used as a suppressor of axon extension, while the agent for inactivating α-chimerin or suppressing the function of α-chimerin can be used as a promoter of axon extension.

Examples of such an agent having suppressive effects include an anti-α-chimerin antibody capable of neutralizing the action of α-chimerin. The anti-α-chimerin antibody capable of neutralizing the action of α-chimerin, that is, an antagonistic antibody against α-chimerin, can be prepared by antibody preparation methods known in the art. Such an antibody can block, for example, the binding of α-chimerin and EphA4. These antibodies are, preferably, genetically engineered antibodies that are artificially modified for the purpose of, for example, reducing xenoantigenicity to humans, including chimeric antibodies and humanized antibodies. These modified antibodies can be produced using known methods. The chimeric antibodies comprise variable regions derived from a non-human mammal antibody and constant regions derived from a human antibody. The humanized antibodies comprise a complementarity determining region derived from a non-human mammal antibody and framework and C regions derived from a human antibody. The humanized antibodies have reduced antigenicity within human bodies and are therefore useful as an active ingredient for the agent of the present invention. The humanized antibody, also called reshaped human antibodies, can be obtained by transplanting a complementarity determining region (CDR) of a non-human mammal antibody, for example, a mouse antibody, into CDR of a human antibody. Such humanized antibodies encompass a human antibody that can be obtained by administering antigens to a transgenic animal containing human antibody loci and having the ability to produce human-derived antibodies. Examples of such a transgenic animal include mice. The mice capable of producing human antibodies can be prepared according to the method described in, for example, the pamphlet of WO02/43478. The anti-α-chimerin antibody also encompasses a portion of the anti-α-chimerin antibody (partial fragment), which is an antibody fragment having the action of the antibody on antigens. Specific examples thereof include F(ab')$_2$, Fab', Fab, Fv, disulfide-stabilized Fv, single-chain Fv (scFv), and polymers thereof.

Furthermore, a compound that may be used as an α-chimerin-targeting drug capable of suppressing the activity of α-chimerin or expression of α-chimerin encompasses a compound capable of suppressing expression of α-chimerin in vivo. Examples of such a compound include a compound that can cleave target mRNA having a particular sequence through RNAi (RNA interference) and suppress expression of a gene corresponding to the mRNA. In RNAi, siRNA (short interfering RNA) comprising a sense strand having a sequence substantially identical to particular target mRNA and an antisense strand complementary to the sense strand recognizes, as guide RNA, the target sequence and cleaves the target mRNA, thereby suppressing the corresponding gene expression. The siRNA is formed from double-stranded RNA (dsRNA) through intracellular or in vivo dicer processing. Examples of the compound include double-stranded RNA having RNAi action. The double-stranded RNA comprises sense RNA having a sequence complementary to the mRNA sequence of a target gene and antisense RNA having a sequence complementary thereto. The sense or antisense strand may have an overhang at the 3' terminus, and the overhang is not limited by the type and number of nucleotides. Examples thereof include a sequence of 1 to 5, preferably 1 to 3, more preferably 1 or 2 nucleotides and specifically include UU and TT. In the present invention, the overhang refers to nucleotides added to the terminus of one strand of siRNA without having their complementary nucleotides at the corresponding position in the other strand. The overhang may be nucleotides constituting DNA. The double-stranded portion has a structure in which a RNA strand (sense strand) having a sequence capable of hybridizing with a target sequence in the sequence of the target gene, the expression of which is to be suppressed through RNA interference, is complementarily bound with an RNA strand (antisense strand) complementary to the sequence. Alternatively, the double-stranded RNA may be short-hairpin RNA (shRNA) having a stem-loop structure in which sense and antisense strands are linked via a loop sequence. The particular target sequence of the α-chimerin-encoding gene as a gene targeted by the double-stranded RNA of the present invention is a sequence in RNA corresponding to the nucleotide sequence of DNA encoding α-chimerin. The target sequence can be appropriately selected based on the human α-chimerin DNA sequence shown in SEQ ID NO: 99. The number of nucleotides thereof is not limited and selected within the range of 15 to 500 nucleotides. Preferably, the target sequence has 15 to 50, 15 to 45, 15 to 40, 15 to 35, or 15 to 30 nucleotides, more preferably 20 to 35 nucleotides, even more preferably 19 to 30 nucleotides, particularly preferably 19 to 29 or 28 nucleotides.

Furthermore, examples of the compound capable of suppressing expression of α-chimerin in vivo include an antisense nucleic acid. The antisense nucleic acid is DNA or RNA that has a sequence capable of complementarily hybridizing with a target gene of interest and can suppress expression of the target gene. The antisense nucleic acid for suppressing expression of α-chimerin according to the present invention is a nucleic acid complementary to a portion of the nucleotide sequence of DNA encoding α-chimerin or RNA sequence corresponding to the DNA sequence. The nucleic acid is 10 to 400 nucleotides, preferably 250 or less nucleotides, more preferably 100 or less nucleotides, even more preferably 50 or less nucleotides, particularly preferably 12 to 28 nucleotides, in length.

Examples of a transfection method with the double-stranded RNA or antisense nucleic acid of the present invention include hydrodynamic, calcium ion, electroporation, spheroplast, lithium acetate, calcium phosphate, lipofection, and microinjection methods.

The present invention also incorporates treatment of ephrin/Eph-associated disease, comprising regulating a series of ephrin/Eph signaling that inactivates a member of low-molecular-weight G proteins of the Rho-family via Rho-GAP. In this case, Rho-GAP such as α-chimerin may be targeted.

Thus, ephrin/Eph-associated disease can be treated by using an agent for regulating the action of Rho-GAP, such as an agent for regulating the action of α-chimerin. The ephrin/Eph-associated disease includes neurologic disease, cancer, and immunologically-related disease.

The present invention further incorporates a method for screening a therapeutic agent for ephrin/Eph-associated disease, which targets Rho-GAP such as α-chimerin. The screening method can comprise administering candidate agents to an isolated cell, tissue, or animal and selecting an effective agent among the agents depending on whether or not each of the agents acts on Rho-GAP and regulates a series of ephrin/Eph signaling that inactivates a member of low-molecular-weight G proteins of the Rho family via Rho-GAP.

The present invention further incorporates a method for screening a regulator of axon extension, comprising administering candidate agents to a cell or an animal and selecting a regulator of axon extension among the agents depending on whether or not each of the agents regulates the interaction between EphA4 and α-chimerin, compared with the case where the agent is not administered. Specifically, α-chimerin, as described above, binds with EphA4 and is activated through ephrinB3/EphA4 signaling. The activated α-chimerin inactivates Rac. As a result, axon extension is suppressed. Thus, axon extension can be expected to be regulated by adjusting (suppressing/promoting) the interaction between EphA4 and α-chimerin partly responsible for this signaling. Moreover, such an agent can be used as a regulator of axon extension. More specifically, the substance for promoting the interaction between EphA4 and α-chimerin can be used as a suppressor of axon extension, while the substance for suppressing or inhibiting the interaction between EphA4 and α-chimerin can be used as a promoter of axon extension.

The present invention further incorporates treatment of human hereditary or congenital disease having abnormal α-chimerin. Examples of the hereditary disease include hereditary disease exhibiting mirror movement, such as Klippel-Feil syndrome. For the treatment of the hereditary disease, for example, an α-chimerin gene may be forcedly expressed after administration. The present invention incorporates a pharmaceutical composition for gene therapy of hereditary disease having abnormal α-chimerin, comprising, as an active ingredient, DNA encoding α-chimerin or an expression vector containing the DNA. Furthermore, α-chimerin and Rac-family genes can be utilized for searching a causal gene of human hereditary or congenital disease. Specifically, to search a causal gene of human hereditary or congenital disease associated with, for example, abnormal motor control, an α-chimerin or Rac-family gene involved in motor control-circuit formation can be targeted.

The present invention further incorporates a mouse having abnormal walking characterized by a rabbit-like hopping gait with left-right synchronized movement of limbs due to lost or reduced function of an α-chimerin gene. The mouse has abnormal ephrin-Eph receptor signaling mechanisms.

The mouse of the present invention can be established by, for example, the following method:

Sib mating of inbred mice such as B6 mice is repeated, and mice characterized by a rabbit-like hopping gait with left-right synchronized movement of limbs are selected. The selected mice are backcrossed to mice of the same strain to obtain F1 mice. The F1 mice are heterozygous for the gene associated with abnormal walking and are therefore free from abnormal walking. Subsequently, crossing between the F1 mice is performed to obtain F2 mice. 25% of the F2 mice have abnormal walking. Further crossing between the F2 mice produce mice, 100% of which have abnormal walking. In this stage, the mouse of the present invention having abnormal walking can be established. The crossing between the F2 mice may further be repeated.

The mice thus established has mutation in an α-chimerin-encoding gene located at the 3.27-Mb interval between SNPs rs13476571 and rs13459064 on chromosome 2. Specifically, the mutation is retroposon (Tn) (its sequence is shown in SEQ ID NO: 98) insertion into exon 9 of the α-chimerin gene. Therefore, the transcript has deletion of exon 9. In the present invention, the mutant gene is called mfy mutation (miffy mutation), which is autosomal recessive mutation. The mouse of the present invention having abnormal walking is homozygous for the mfy mutation. In the present invention, the mouse is called a miffy (mfy) mouse.

The mfy mouse of the present invention has the following features:

(1) it has a rabbit-like hopping gait with left-right synchronized movement of limbs;

(2) in the spinal cord, the white matter in the dorsal funiculus is reduced, prominently at the lumbar levels; and (3) CST axons re-cross the spinal cord midline.

The present invention further incorporates an α-chimerin-knockout mouse having an α-chimerin gene made nonfunctional by deleting the whole or a portion of the α-chimerin gene. The α-chimerin-knockout mice lacks, for example, exon 9 or exons 9 and 10 of the α-chimerin gene.

The knockout mouse can be prepared by methods known in the art, such as homologous recombination. Examples thereof include a method using recombinase and recognition sites of the recombinase. In the method, animals are transfected with DNA in which an α-chimerin gene to be knocked out is flanked by two nucleotide sequences of the recombinase recognition sites, and with DNA in which a promoter is linked upstream of the recombinase. The expressed recombinase cleaves the α-chimerin gene between the recombinase recognition sites to make the gene nonfunctional. Examples of such a method include a method using a Cre-loxP system. The Cre-loxP system is described in, for example, Sauer, B. et al., Proc. Natl. Acad. Sci. USA, 85: 5166-5170, 1988; and Gu, H., et al., Cell, 73, 1155-1164, 1993. The α-chimerin-knockout mice can be prepared using the Cre-loxP system according to the description of the documents. Hereinafter, the knockout of the α-chimerin gene using the Cre-loxP system will be described in detail. Cre is a 38-KD protein derived from bacteriophage P1 and is recombinase belonging to the integrase family. Cre recognizes 34-bp loxP sites and specifically causes DNA recombination at the sites. In the present invention, a Cre gene is linked downstream of a promoter, while the α-chimerin gene to be deleted is flanked by two loxP sequences. The produced Cre gene product can cleave the α-chimerin gene between the loxP genes to obtain a mouse lacking the α-chimerin gene. The preparation of the mouse of the present invention requires mice of two strains: a transgenic mouse having DNA in which a promoter is linked upstream of a Cre gene; and a transgenic mouse having an α-chimerin gene (floxed α-chimerin gene) flanked by two loxP genes. These transgenic mice can be prepared according to methods known in the art, for example, the method described in Pro. Natl. Acad. Sci. USA 77: 7380-7384, 1980.

For example, an appropriate vector containing DNA in which a promoter is linked upstream of Cre, and an appropriate vector containing DNA in which loxP genes are linked to the 3' and 5' termini of the α-chimerin gene to flank the α-chimerin gene, are used. These DNAs are introduced to mouse totipotent cells such as embryonic stem cells (ES cells), and the cells are allowed to develop to individuals. Individuals having the transgenes incorporated in the chromosomes of the somatic and germ cells can be selected to prepare knockout mice. The transgenic mouse having DNA in which a promoter is linked upstream of a Cre gene may be, for example, a CAG-Cre mouse that contains a CAG promoter and is capable of systemically expressing Cre enzymes. The α-chimerin-knockout mouse can be prepared by crossing the mice of these two strains. The α-chimerin-knockout mouse (α-Chn-KO mouse) of the present invention has the same features as those of the mfy mouse.

The mfy and α-chimerin-knockout mice can be used, for example, as a model mouse of human hereditary disease caused by abnormal α-chimerin, for elucidating the disease state or screening a therapeutic drug. These mice can be used as a mouse for studying ephrinB3/EphA4 forward signaling or α-chimerin-mediated signaling.

EXAMPLES

The present invention will be described specifically with reference to Examples below. However, the present invention is not intended to be limited by these Examples.

In the present Examples, materials and methods described below were used.
Preparation of Antibody A KLH-coupled synthetic peptide (MALTLFDTDEYRP-PVWKC (SEQ ID NO: 1)) corresponding to the N-terminus of α2-chimerin (FIG. 11A) was used to prepare a rabbit polyclonal antibody (BSI Research Resources Center).

Sera were affinity-purified on the same peptide.

Commercially available antibodies were used, including anti-EphA4 (07-309, Upstate Cell Signaling Solutions), anti-ephrin (sc-7281, Santa Cruz Biotechnology), and anti-actin (MAB1501, Chemicon) antibodies. Anti-myc and GFP mouse monoclonal antibodies, an anti-HA rabbit polyclonal antibody (Santa Cruz Biotechnology), an anti-HA rat monoclonal antibody (Roche), and anti-Rac 1 mouse monoclonal antibody (Transduction Laboratories), and a horseradish peroxidase-conjugated secondary antibody (DAKO) were further used.
Accession Numbers of DNA Nucleotide Sequences Information on the DNA nucleotide sequences was deposited in the DNA Data Bank of Japan (DDBJ).

Accession numbers are: AB264771 (α1-Chn$^{mfy}$ cDNA) (SEQ ID NO: 94, FIG. 16), AB264772 (α2-Chn$^{mfy}$ cDNA) (SEQ ID NO: 95, FIG. 17), AB264773 (α3-Chn$^{mfy}$ cDNA) (SEQ ID NO: 96, FIG. 18), AB264774 (α3-Chn$^{WT}$ cDNA) (SEQ ID NO: 97, FIG. 19), and AB264775 (retroposon) (SEQ ID NO: 98, FIG. 20).
Histological Study The brains and the spinal cords were removed from mice and fixed in 4% paraformaldehyde (PFA) in a 0.1 M phosphate buffer (PB) (pH 7.4).

A microslicer (Dosaka, Japan) or freezing microtome (Yamato Kohki, Japan) was used for preparation of sections.

From 3 wild-type mice, 16 heterozygous mice, and 17 homozygous mice, all of which were adults, unstained 400-μm thick serial sections (in the horizontal or transverse direction) or Nissl-stained 60- or 100-μm thick serial sections (in the horizontal, coronal, sagittal or transverse direction) were prepared for examining the gross morphologies of the brain and spinal cord.

The transverse sections (50 to 60 μM thick) of the brain stems and spinal cords of littermate mice at P2 to P11 were subjected to immunohistochemical experiments using an anti-α2-chimerin (1:4,000) or anti-EphA4 (Upstate; 1:2,000) antibody.

These experimental approaches follow the method described in Iwasato et al., 2004, Genesis, 38, 130-138.
Tracing Experiment of Corticospinal Tract and Spinal Local Circuits Based on the description of Kullander et al., 2001, Neuron 29, 73-84, the anterograde tracing experiment was conducted with some modifications. Adult mice were anaesthetized with a ketamine/xylazine mixture, and an anterograde tracer biotinylated dextran amine (15% BDA in 0.01 M PB; Invitrogen, Eugene; 0.2 μl/site into 8-10 injection sites) was injected into the left motor cortex under pressure.

Nine to 34 days later, these mice were perfused with a saline and subsequently with 4% PFA in 0.1 M PB (pH 7.4). The brains and the spinal cords were removed, then fixed, and cryoprotected, and their 60-μm thick sections were prepared using a freezing microtome (Yamato Kohki, Japan). The prepared sections were reacted in 3% $H_2O_2$ in a phosphate-buffered saline (PBS) for 10 minutes, subsequently treated with an ABC kit (Vector), and developed in 3,3'-diaminobenzidine (DAB).

In the experiment, 7 mfy/mfy mice, 8 mfy/+ mice, 3 α-Chn-KO mice, and 3 wild-type mice were used.

Based on the description of Yokoyama et al., 2001, Neuron 29, 85-97, the retrograde tracing experiment was conducted with some modifications.

An Alexa Fluor 488 conjugate of cholera toxin subunit B (1% CTB in 0.01 M PB; Invitrogen; 0.1 μl/site into 3-5 injection sites) was injected into the left half of the spinal cords of anaesthetized adult mice at lumbar levels. Six to 11 days later, the mice were perfused. The brains and the spinal cords were recovered, then fixed, and cryoprotected, and their 60-μm thick sections were prepared using a freezing microtome.

A quantitative comparison of cortex neurons was conducted using a microscope (Leica DMR) for 4 serial sections.

Unilateral injection was verified for 6 serial spinal cord sections of the injection sites.

Neurons that extended in the ipsilateral side were analyzed according to the method described in Kullander et al., 2003, Science 299, 1889-1892, with some modifications.

The spinal cords isolated from mice at P1 to P5 were fixed in 4% PFA in 0.1 M PB.

A small DiI (Molecular Probes, Oregon, USA) crystal was added to unilateral sections prepared at L4 levels, and the spinal cords were incubated in the same fixing solution in the dark at 37° C. for 11 to 15 days according to the method described in Lee et al., 2005, Neurol. 485, 280-292, to diffuse the stain.

The DiI-labeled spinal cords were cut in the transverse direction at L2 levels using a microslicer, and sections (100 μm thick) with most visualized cell bodies of descending commissural interneurons were selected from each mouse.

Figure 10:
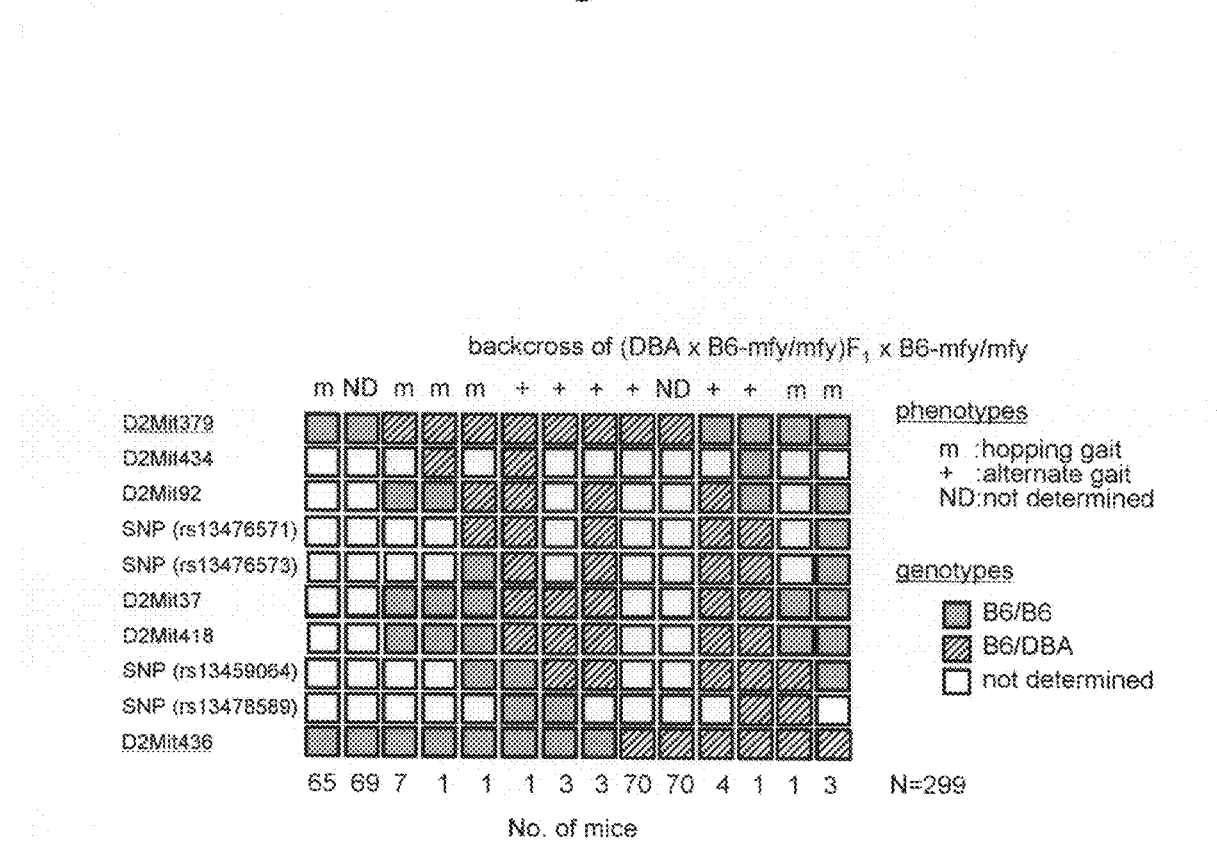
FIG. 10 is a diagram showing gene mapping of mfy mutation.

Images were obtained using a DC300F digital camera (Leica). Signal intensity was measured using Image-J software (NIH). The experiment was conducted, in which observers were blinded to genotype information.
Linkage Analysis For linkage analysis, mfy/mfy mice in a B6 background were crossed with WT DBA/2 (DBA) mice, and the obtained F1 (mfy/+) mice were backcrossed to the mfy/mfy parents. The obtained mouse progeny was genotyped using microsatellite markers (Mouse Genome Informatics) and phenotype (walking)-associated SNPs (National Center for Biotechnology Information). "Boundary" markers (D2Mit379 and D2Mit436) for a mfy mutation-containing site were identified. Then, all the obtained backcross progeny was genotyped using D2Mit379 and D2Mit436. Mice that displayed a recombination with these markers were further analyzed, and the mfy locus was mapped. Finally, the mfy locus was mapped to the 3.27-Mb interval between SNPs rs13476571 and rs13459064 on chromosome 2 (FIG. 10). PCR primers for the microsatellite markers and SNPs were designed using the Mouse Genome Informatics (http://www.informatics.jax.org/) and National Centre for Biotechnology Information (http://www.ncbi.nlm.nih.gov/SNP/) databases, respectively, and verified by PCR using the genomic DNAs of inbred B6 and DBA/2 mice and B6/DBA F1 hybrid mice. The following PCR primers for the selected SNPs were used:

```
rs13476571:
5'-GGC TCA GTG TGG TGC TTT GG-3'   (SEQ ID NO: 2)
5'-TAG TTG GTA CCA CGC AGCAG-3'    (SEQ ID NO: 3)

rs13476573:
5'-AGC TTT GAG CCT GGT GAT CT-3'   (SEQ ID NO: 4)
5'-AGA ACG ATGTGC TAC ACA TG-3'    (SEQ ID NO: 5)

rs13459064:
5'-CTG GCA TTT CAC TGA ACA CA-3'   (SEQ ID NO: 6)
5'-TTA GGG CCG TTC TGT TTG AC-3'   (SEQ ID NO: 7)

rs13476589:
5'-CCT CAA CAC TGA CTGAAC TA-3'    (SEQ ID NO: 8)
5'-TCT TAA TGC ACT GCA GTG TC-3'   (SEQ ID NO: 9)
```

Expression Profiling of Candidate Genes

According to the NCBI database, 30 genes have been reported within the 3.27-Mb interval between SNPs rs13476571 and rs13459064. The transcript sizes and levels of 20 candidate genes (groups 2 to 4, Table 1) were compared among the mfy/mfy (n=3), mfy/+ (n 3), and wild-type (n=1) P5 mouse brains by RT-PCR using primer pairs amplifying P5 cDNA between the 5' and 3' untranslated regions. The following PCR forward primers were used:

```
B230120H23Rik:
TATGAGATGTCGTCTCTCGG            (SEQ ID NO: 10)

Cdca7:
TGTGTTCCGACGAACTATCC            (SEQ ID NO: 11)

Sp3:
GGTGATTTGGCTTCTGCACA            (SEQ ID NO: 12)
and

TGAGCTGTCCTAAACACAC             (SEQ ID NO: 13)

1700011J10Rik:
AAGGTATGCCTGCTGCTCAT            (SEQ ID NO: 14)

2810409H07Rik:
CACGATGCCCCCGAAAAAGG            (SEQ ID NO: 15)

Sp9:
CAGCCCAAAACCTGCTATGG            (SEQ ID NO: 16)
and

TGCTATGGCCACGTCTATAC            (SEQ ID NO: 17)

1700023B02Rik:
GACGCCAAGATGGGGAAGTC            (SEQ ID NO: 18)

Scrn3:
GAGAAATGGAACCCTATTCC            (SEQ ID NO: 19)

Gpr155:
AAGAACTCAACGCTTGCTGG,           (SEQ ID NO: 20)

TCTGATTGTTGACCAGCAAC,           (SEQ ID NO: 21)
and

AGGCCAGTTTGGAAGTGGAG            (SEQ ID NO: 22)

Chrna1:
TTCTGGGCTCCGAACATGAG            (SEQ ID NO: 23)
and

TGGAGCTCTCGACTGTTCTC            (SEQ ID NO: 24)

α1-Chn:
GAGAGATGCTGCATGCTTTG            (SEQ ID NO: 25)

α2-Chn:
CCATGGCTCTGACCCTGTTC            (SEQ ID NO: 26)

α3-Chn:
AGGGCTTTCCTTGCTGTGTC            (SEQ ID NO: 27)

Atp5g3:
CGCCAGGAAGAAAGATGTTC            (SEQ ID NO: 28)

Lnp:
CCGCTTTTCTCAGCTGTGAC            (SEQ ID NO: 29)

Hoxd8:
ATGAGCTCGTACTTCGTGAA            (SEQ ID NO: 30)
and

TGAACCCGCTGTACTCCAAC            (SEQ ID NO: 31)

6720416L17Rik:
AAGAAGGTGTGCCCAAGGCT            (SEQ ID NO: 32)

Hoxd1:
GAAGCCACTATTTACCTCGG            (SEQ ID NO: 33)
and

AGCGAGCCATGAGCTCTTAC            (SEQ ID NO: 34)

Mtx2:
CTCTGCTCGTCTTAGCGTTG            (SEQ ID NO: 35)

A330043C09Rik:
CCAGGAGCCATTTATCTCAG            (SEQ ID NO: 36)
and

GCAAGACAGATGGGACTTTC.           (SEQ ID NO: 37)
```

The following PCR reverse primers were used:

```
B230120H23Rik:
GCATCTGACCCAATCCCTCA            (SEQ ID NO: 38)

Cdca7:
ATCTTCAGGCTCTACGCTTG            (SEQ ID NO: 39)

Sp3:
ACTGTGACAAGCTGTAAAGG            (SEQ ID NO: 40)
and

GGTTAGACTACCATTCGCA             (SEQ ID NO: 41)

1700011J10Rik:
GTGCTCATGTGAGTATCTTC            (SEQ ID NO: 42)

2810409H07Rik:
AAAACACCCATCCCCCCAAG            (SEQ ID NO: 43)

Sp9:
CTCTAGGAGTCGTTGGGACC            (SEQ ID NO: 44)
```

-continued

```
and

TTATGTCGGAGGATGGCTCG            (SEQ ID NO: 45)

1700023B02Rik:
TGCTCCGAAGCTCTGTTGAG            (SEQ ID NO: 46)

Scrn3:
TTACCAGGGCAGTGAGGAAG            (SEQ ID NO: 47)

Gpr155:
CTAGCACTTGAGTTCGTTAC,           (SEQ ID NO: 48)

TCTGGCACTTAAGTCTTAGG,           (SEQ ID NO: 49)
and

AGATGACCTGCCCAAGGTCA            (SEQ ID NO: 50)

Chrna1:
TGTGAGACATACACGTAGGC,           (SEQ ID NO: 51)

TCAGCCTCTGCTCATCCTTG,           (SEQ ID NO: 52)
and

AGGACATGTAGAACACTGCA            (SEQ ID NO: 53)

α-Chn:
TCTGGGTATTTGGCCAAACC            (SEQ ID NO: 54)

Atp5g3:
TACAGTCTTCGGAGTCACAG            (SEQ ID NO: 55)

Lnp:
ATCCAGTTGAAGGCACATGG            (SEQ ID NO: 56)

Hoxd8:
TGGTGTCCACCAGTATATAC            (SEQ ID NO: 57)
and

CAAGAGCAGTGACATTAAGG            (SEQ ID NO: 58)

6720416L17Rik:
CCGGGTCTTCGAGAAGCAAA            (SEQ ID NO: 59)

Hoxd1:
AAGGCTCTTGAGCCTGAGAA            (SEQ ID NO: 60)
and

CGTTTAGGCAGGTAGCTAAG            (SEQ ID NO: 61)

Mtx2:
CCTCACAGCATCATCACGTG            (SEQ ID NO: 62)

A330043C09Rik:
TCACGCTGATGATACCATCA,           (SEQ ID NO: 63)

AGCAAGGGGGTTTCTGTTGG,           (SEQ ID NO: 64)
and

CCAGACATCTGGATGTCAGT.           (SEQ ID NO: 65)
```

TABLE 1

| Name | Group* |
|---|---|
| Between SNPs rs13476571 and rs13476573 | |
| B230120H23Rik | 3 |
| Cdca7 | 3 |
| Sp3 | 3 |
| 1700011J10Rik | 3 |
| 2810409H07Rik | 3 |
| Sp9 | 2 |
| Between SNP rs13476573 and D2Mit379 | |
| 1700023B02Rik | 3 |
| Scrn3 | 3 |
| Gpr155 | 3 |
| Waspip | 1 |
| Chrna1 | 2 |
| α-Chn | 4 |
| Atf2 | 1 |
| Atp5g3 | 3 |
| Lnp | 3 |
| Evx2 | 1 |
| Hoxd13 | 1 |
| Hoxd12 | 1 |
| Hoxd11 | 1 |
| Hoxd10 | 1 |
| Between D2Mit379 and D2Mit418 | |
| Hoxd9 | 1 |
| Hoxd8 | 2 |
| Hoxd4 | 1 |
| Hoxd3 | 1 |
| 6720416L17Rik | 3 |
| Hoxd1 | 2 |
| Mtx2 | 3 |
| Between D2Mit418 and SNP rs13459064 | |
| A330043C09Rik | 2 |
| Hnrpa3 | 3 |
| Nfe212 | 3 |

Group 1: gene group that was excluded because their knockout mice have been shown to survive to adulthood and have normal gaits.

Group 2: genes that are not expressed in the P5 mfy/mfy, mfy/+, or wild-type brain.

Group 3: genes that do not vary in transcript size and level between wild-type and mfy/mfy mice.

Group 4: α-Chn gene that varies in transcript size and level between wild-type and mfy/mfy mice.

Real-Time Quantitative RT-PCR

Total RNAs were isolated from the motor cortex and spinal cord of mice (n=3) at P4 using RNeasy Mini Kit (QIAGEN). All the samples were digested on columns using RNase-free DNase. cDNAs were synthesized from the total RNAs (1.2 µg/sample) using Superscript III two-step qRT-PCR kit (Invitrogen). Real-time quantitative RT-PCR was conducted in ABI Prism 7700 (ABI) using Platinum SYBR green qRT-PCR Super mix UDG with ROX (Invitrogen). PCR parameters involved 45 cycles each involving 50° C. for 2 minutes, 95° C. for 2 minutes, and 95° C. for 15 seconds, 65° C. for 30 seconds, and 72° C. for 30 seconds. Melting profile analysis was conducted in the final stage of each step. All quantitative RT-PCR reactions were performed at 3 cycles. The following primer sets were used:

For α1-Chn, 5'-GAGAGATGCTGCATGCTTTG-3' (SEQ ID NO: 66) and 5'-TGAAGCACTTCTTCACAAGG-3' (SEQ ID NO: 67); for α2-Chn, 5'-GCTACCTCATCCGT-GAGAGC-3' (SEQ ID NO: 68) and 5'-CCCAACAAAGT-GCTTTCCAT-3' (SEQ ID NO: 69); and for α3-Chn, 5'-AGGGCTTTCCTTGCTGTGTC-3' (SEQ ID NO: 70) and 5'-TAGGTCCCTTCTCATGAACC-3' (SEQ ID NO: 71). Linear plasmids pS80 (α1-Chn cDNA), pM2 (α2-Chn cDNA), and pM3 (α3-Chn cDNA) were diluted and used as absolute standards for cDNA quantification.

Preparation of Knockout Animals

A Tg construct was prepared by modifying the RP23-413N9 BAC clone (Roswell Park Cancer Institute, NY, USA) derived from B6 mouse genomic DNA. The Tg founder mice were prepared by injecting the linearized constructs into fertilized eggs. α-chimerin-KO mice were prepared using MS12 ES cells derived from the B6 strain. Details will be shown below. All the mice were maintained according to the institutional guidelines of the animal facilities of the RIKEN-BSI.

BAC Transgenic and α-Chn-KO Mice

A BAC α-Chn Tg construct was prepared using a Red/ET recombination system (Gene Bridges, Germany). A fragment containing SV40 poly(A) and FRT-Amp-FRT followed by α2-Chn cDNA was amplified using DNA polymerase Pyrobest (Takara, Japan) and primers 347 (5'-GTTGACAT-CACTTGTTAGAAG-3' (SEQ ID NO: 72)) and 348 (5'-TCAAAGGCATCCAAAGATGAGCCTGTAA-CACTGCACACTCCAAGCACTGAGCATT CCCTTGACCAAGTTGCTGAAG-3' (SEQ ID NO: 73)). *E. coli* strains containing the RP23-413N9 BAC clone derived from C57BL/6 (B6) mouse genomic DNA (Roswell Park Cancer Institute, NY, USA) that covered exons 1 to 7 of α2-Chn were transformed with pSC101-BAD-gbaA (Gene Bridges, Germany) and subsequently with the purified PCR product. The Amp gene was removed from the construct by transforming *E. coli* with a 706-FLP plasmid (Gene Bridges, Germany). The obtained BAC α-Chn Tg construct was verified by digestion with restriction enzymes, and its DNA sequence was determined according to the method described in Iwasato et al., 2004, Genesis 38, 130-138. The NotI fragment was purified using a Sepharose column according to the method described in Hammes and Schedl, 2000, Generation of transgenic mice from plasmids, BACs and YACs. In Mouse genetics and transgenics, I. J. Jackson, and C. M. Abbott, eds. (Leeds, Oxford University Press), pp. 217-245. Removal of the BAC vector was confirmed by pulsed-field gel electrophoresis (FIGE Mapper: Bio-Rad, CA, USA). The purified DNA fragment (2 ng/μl) was injected into pronuclei in the fertilized eggs of B6/DBA F2 mice to prepare TG mice (BSI Research Resources Center).

The α-Chn-knockout (KO) allele was prepared by crossing α-Chn flox mice (T.I. M.I and S.I., unpublished results) with CAG-Cre deleter mice. In the KO allele, the KpnI-HindIII fragment containing exons 9 and 10 was replaced with a loxP site. These mice were prepared using MS12 embryonic stem cells (ES cells) derived from the B6 strain and maintained in a B6 background.

Genotyping

The following primer pairs were used in genotyping:

```
5'-AGGGCTTTCCTTGCTGTGTC-3'    (SEQ ID NO: 74)/
5'-ACGTCTCCTGACACCATTCC-3'    (SEQ ID NO: 75)
(for WT, 0.9 kb and 2.8 kb; for mfy-KO allele,
no bands), 5'-GGAGTTCCAGCTCCATTGTG-3'    (SEQ ID NO: 76)/
5'-ACCATGACAGTGAGCTTTCC-3'    (SEQ ID NO: 77)
(for KO allele, 234 bp),
and 5'-CTTCACGAAGCACTGAGATC-3'    (SEQ ID NO: 78)/
5'-AGGTTCTCTGCACTCATCAG-3'    (SEQ ID NO: 79)
(for Tg, 119 bp).
```

Western Blot Analysis

Western blot analysis was conducted according to the method described in Helmbacher et al., 2000, Development 127, 3313-3324, with modifications. The mouse brain and spinal cord were homogenized in a lysis buffer (containing 10 mM Tris pH 7.5, 150 mM NaCl, 5 mM EDTA, 10% glycerol, 1% Triton X-100, and a protease inhibitor) or Pro-PREP protein extraction solution (iNtRON Biotechnology, Inc.), and the homogenates were clarified by centrifugation. Proteins were separated by SDS-PAGE and blotted to a polyvinylidene difluoride membrane. The membrane was stained with an anti-EphA4 polyclonal antibody (1:2,000; Upstate Cell Signaling Solutions, Lake Placid, N.Y., #07-309), an anti-ephrinB3 polyclonal antibody (1:100; Santa Cruz Biotechnology, Santa Cruz, Calif., sc-7281), an anti-EphB1 polyclonal antibody (1:200; Santa Cruz Biotechnology, sc-926), an anti-α2-chimerin polyclonal antibody (1:2,000), an anti-ephrinA2 monoclonal antibody (1:500; Techne Corporation, Minneapolis, Minn., 43458), and an anti-actin monoclonal antibody (1:5,000; Chemicon International Inc, Temecula, Calif., MAB1501R) and autoradiographed using enhanced chemiluminescence (Amersham Pharmacia Biotechnology, EPN2132; Santa Cruz Biotechnology, sc-2048).

DNA Construct

EphA4 cDNA of the B6 mouse brain was amplified using high-fidelity DNA polymerase Pyrobest (Takara, Japan) and the following primer set: 5'-TGAGCTCTAGAAGCTGG-GATTTTCTATTTCATC-3' (SEQ ID NO: 80) and 5'-TGCG-GCCGCTCAGACAGGAACCATCCTGCCATG-3' (SEQ ID NO: 81). Subsequently, the amplification product was inserted into a pcDNA3 (Invitrogen) vector having Igk-Myc-tag at the N-terminus. EphA4$^{FF}$ (Y596F/Y602F) mutants were prepared by a PCR-based method using the following primer sets: CCATGGCTGGGATTTTCTATTTC (SEQ ID NO: 82)/AAGTTCTAACACCTTGATTCAAA (SEQ ID NO: 83), TGAGCTCTAGAAGCTGGGATTTTC-TATTTCATC (SEQ ID NO: 84)/AAGGGATCCA-CAAAAGTTCTAACACCTTGATTC (SEQ ID NO: 85), CGAAGACCCCAACCAGGCAGT (SEQ ID NO: 86)/GCT-CAGACAGGAACCATCCTG (SEQ ID NO: 87), and GTG-GATCCCTTTACATTCGAAGACCCCAACCAGGCAG (SEQ ID NO: 88)/TGCGGCCGCTCAGACAGGAAC-CATCCTGCCATG (SEQ ID NO: 89).

Wild-type and mfy α2 (or α1)-Chn were separately amplified from the cDNAs of the wild-type and mfy/mfy mouse brains, respectively, and the amplification product was inserted into a pEF-BOS vector having HA-tag at the N-terminus. A pGEX vector (Amersham) was used to prepare a glutathione S-transferase (GST)-fusion protein-expression plasmid. An enhanced yellow fluorescent protein (EYFP)-expression plasmid having a CAG promoter was provided by Dr. Miyazaki (Osaka University, Japan) and Dr. Saito (Chiba University, Japan). A U6 RNA polymerase III promoter derived from a pSilencer short-hairpin RNA (ShRNA)-expression vector was inserted downstream of the EYFP gene in pCAG-EYFP to cause expression of shRNA and EYFP proteins within the same cells. siRNA for rat α-chimerin was designed based on the description of Van de Ven et al., 2005, J. Neurosci. 25, 9488-9496. siRNA oligonucleotides (5'-TC-GAGGCTTCCTCTCATCACCTACGAT-TCAAGAGATCGTAGGTGATGAGAGGAAT TTTTTG-GAA-3' (SEQ ID NO: 90) and 5'-CTAGAAGGTTTTTAAGGAGAGTAGTG-GATGCTAGAGAACTTAGCATCCACTACT CTCCT-TCGG-3' (SEQ ID NO: 91)) or negative control oligonucleotides (5'-TCGAGGCTTCAGTACATCCTCCTCCATT CAAGAGATGGAGGAGGATGTACTGAAT TTTTTG-GAA-3' (SEQ ID NO: 92) and 5'-CTAGAAGGTTTTT-TAAGTCATGTAGGAGGAGGTAGAGAACT-TACCTCCTCCTACA TGACTTCGG-3' (SEQ ID NO: 93)) were annealed and cloned into the XhoI/BamHI site of the pCAG-EYFP-hu6 vector. All the encoded sequences and siRNA sequences in each construct were confirmed by sequencing.

Cell Culture and Transfection

HEK293T and COS-7 cells were separately cultured in a Dulbecco's modified eagle's medium containing 10% fetal bovine serum, 4 mM glutamine, 100 units/ml penicillin, and 0.2 mg/ml penicillin under conditions involving 5% $CO_2$ and 37° C. These cells were transfected using Lipofectamine Plus and Lipofectamine 2000, respectively.

Immunoprecipitation

Twenty-four hours after transfection, the HEK293T cells ($1 \times 10^6$ cells/60-mm culture dish) were lysed with an ice-cold cell lysis buffer (20 mM Tris-HCl, pH 7.5, 150 mM NaCl, 2 mM $MgCl_2$, 1% Triton X-100, 10 mM NaF, 1 mM $Na_3VO_4$, 1 mM PMSF, 10 µg/ml aprotinin, and 10 µg/ml leupeptin). After centrifugation, the supernatant was clarified in advance at 4° C. for 1 hour using protein G Sepharose beads (Amersham Biosciences). The lysates were incubated with 1 µg/ml ephrinA1-Fc fusion proteins (R&D Systems) for 2 hours and then incubated using protein G Sepharose beads for 1 hour. To detect the interaction between endogenous α-chimerin and EphA4, cortical neurons of E18.5 rats were plated at a cell density of $1 \times 10^6$ cells onto a 60-mm dish coated with poly-D-lysine, and cultured in a neurobasal medium supplemented with 2% B27 for 2 days. The neurons were stimulated with 5 µg/ml pre-clustered ephrinB3-Fc or control Fc for 5 minutes or 15 minutes. Then, cell lysates were prepared from the anterior dorsomedial to dorsal neocortex of wild-type mice at P3. After centrifugation, the supernatant was incubated with an anti-α2-chimerin antibody for 2 hours and subsequently incubated with protein G Sepharose beads for 1 hour. The beads were washed with a lysis buffer, and bound proteins were analyzed by SDS-PAGE and immunoblotting. Densitometry analysis was conducted using Image-J software, and relative Rac activity was determined based on GST-CRIB-bound Rac1 levels normalized to Rac1 levels in the cell lysate.

Pull-Down Assay

Recombinant GST-fused α2-chimerin and its deletion mutant were purified from *E. coli* according to the method described in Katoh et al., 1998, J. Biol. Chem. 273, 2489-2492. Protein concentrations were determined by comparison with bovine serum albumin standards stained with Coomassie Brilliant Blue after SDS-PAGE. For pull-down assay, HEK293T cells ($1 \times 10^6$ cells) transfected with Myc-tagged EphA4 were lysed with an ice-cold cell lysis buffer (20 mM Tris-HCl, pH 7.5, 150 mM NaCl, 2 mM $MgCl_2$, 1% Triton X-100, 10 mM NaF, 1 mM $Na_3VO_4$, 1 mM PMSF, 10 µg/ml aprotinin, and 10 µg/ml leupeptin). After centrifugation, the supernatant was incubated with 10 µg of GST-fusion proteins at 4° C. for 1 hour and subsequently incubated with glutathione-Sepharose beads at 4° C. for 1 hour. The beads were washed with an ice-cold cell lysis buffer, and bound proteins were lysed in a Laemmli sample buffer and analyzed by SDS-PAGE and immunoblot using an anti-Myc antibody.

Measurement of Rac1 Activity

The CRIB domain of αPak (amino acids 70 to 150) was expressed as a fusion protein with GST in *E. coli*, and the fusion protein was purified with glutathione-Sepharose beads and isolated from the beads using 16 mM reduced glutathione. The purified protein was dialyzed against 10 mM Tris-HCl, pH 7.5, 2 mM $MgCl_2$, and 0.1 mM dithiothreitol (DTT) and stored at −80° C. Protein concentrations were determined by comparison with bovine serum albumin standards stained with Coomassie Brilliant Blue after SDS-PAGE. Twenty-four hours later, transfected COS-7 cells ($5 \times 10^5$ cells/60-mm culture dish) were stimulated with 2 µg/ml pre-clustered ephrinB3-Fc or Fc in a serum-free medium for 10 minutes. Subsequently, the cells were lysed for 5 minutes with an ice-cold cell lysis buffer (50 mM Tris-HCl, pH 7.4, 100 mM NaCl, 2 mM $MgCl_2$, 1% Nonidet P-40, 10% glycerol, 1 mM DTT, 1 mM phenylmethanesulfonyl fluoride (PMSF), 1 mg/ml aprotinin, and 1 µg/ml leupeptin) containing 4 µg of GST-CRIB. The cell lysate was centrifuged at 10,000 g at 4° C. for 5 minutes, and the supernatant was incubated with glutathione-Sepharose beads at 4° C. for 30 minutes. The beads were washed with a lysis buffer, and bound proteins were analyzed by SDS-PAGE and immunoblotting.

Immunofluorescence Microscopy

Cortical neurons primarily cultured on cover slips were fixed using 4% PFA in PBS for 20 minutes and washed 5 times with PBS. The cells were permeabilized with 0.2% Triton X-100 in PBS for 10 minutes and incubated using 10% FBS in PBS for 30 minutes to block non-specific antibody binding. Subsequently, the cells were incubated with an anti-α2-chimerin antibody (1:4000 dilution) in PBS for 1 hour and then incubated with an Alexa 594-conjugated goat anti-rabbit IgG antibody (1:2000 dilution, Molecular Probes) in PBS for 1 hour. The cells on cover slips were mounted in 90% glycerol containing 0.1% p-phenylenediamine dihydrochloride in PBS. The cells were photographed using a Leica DC350F digital camera system containing a Nikon Eclipse E800 microscope.

Growth Cone Collapse Assay

Primary neurons were dissociated from the anterior dorsomedial to dorsal neocortex of E16.5 mice or E18.5 rats according to the method described in Ishikawa et al., 2003, J. Neurosci. 23, 11065-11072; and Kullander et al., 2001, Neuron 29, 73-84. The neurons were plated at a density of $1.0 \times 10^4$ cells (mouse neuron) or $4.0 \times 10^4$ cells (rat neuron) onto poly-D-lysine- and laminin (Sigma)-coated cover slips (round, 13 mm in diameter) and cultured in a neurobasal medium supplemented with 2% B27 (Invitrogen). Subsequently, they were stimulated with 5 µg/ml ephrinB3-Fc-fused proteins (R&D Systems) or only with Fc (Jackson ImmunoResearch) as a control for 30 minutes. The Fc and the ephrin-Fc were pre-clustered with an anti-Fc antibody (1/10 w/w anti-Fc/Fc; Jackson ImmunoResearch) at room temperature for 1 hour before use. The cells were fixed using 4% PFA in PBS and stained with rhodamine-conjugated phalloidin (Invitrogen). The tips of longest neural spines were analyzed as described in Oinuma et al., 2004, Science 305, 862-865, and growth cone-positive cells were identified as having a lobopodium and a filopodium in visualization by F-actin staining. For expression of short-hairpin RNAs (shRNAs), the neurons were transfected with pCAG-EYFP-U6-shRNA using Lipofectamine 2000 or Amaxa rat neuron nucleofector kit (Amaxa Biosystems).

The following results were obtained in the present Examples:

1. A Novel Autosomal Recessive Mutation Leading to a Rabbit-like Gait

The present inventor unexpectedly discovered mutant mice with a rabbit-like gait in the course of preparation of transgenic mice homozygous for a ChAT-Cre#23 construct (Inoue et al., 2003, EMBO J. 22, 6665-6674). This novel mutation, which was designated as miffy (mfy), was autosomal recessive. It was initially assumed that the mfy mutation was caused by gene disruption attributed to transgene (Tg) insertion. However, this assumption was not correct, because mfy segregated from Tg in the course of crosses, suggesting that the mfy mutation arose spontaneously. Homozygous (mfy/mfy) mice were healthy and fertile. Their bodies were slightly smaller during the postnatal developmental period. However, such differences were not evident in adulthood. Wild-type and heterozygous (mfy/+) mice exhibited normal walking with left-right alternate stepping of limbs. By contrast, the mfy/mfy mice (n>100) were found to move their left and right hind limbs synchronously, resulting in a rabbit-like hopping gait (FIG. 1A). The mean±SEM proportion of left-right synchronized gaits among 40 randomly selected gaits analyzed was 0 for mfy/+ (n=13) mice and 98.42±0.61% for mfy/mfy (n=19) mice (p<0.0001, unpaired t-test). The general structure of the mfy/mfy mouse brain had no distinguishable abnormality (WT (wild-type) and mfy/+ mice; FIGS. 8A and 8B). By contrast, a morphological analysis of the spinal cord revealed that the white matter in the dorsal funiculus was reduced, most prominently at lumbar levels (FIG. 8C).

Figure 8:
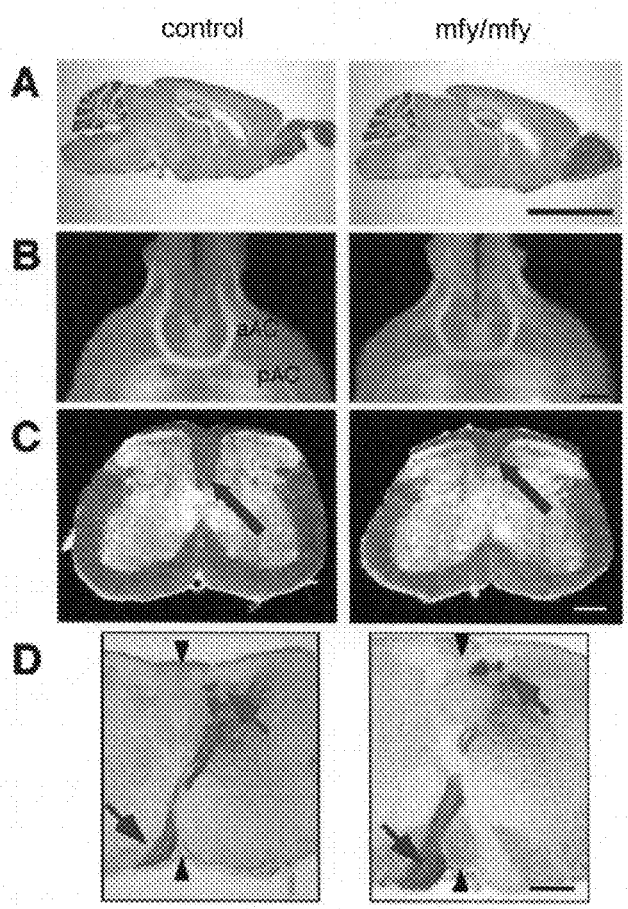
FIG. 8 is a diagram showing abnormal morphology in the spinal cord of mfy mice.

FIG. 8 shows abnormal morphology in the spinal cord of mfy. FIG. 8A shows results of Nissl-staining sagittal sections of adult mice. The brain was histologically indistinguishable between the mfy and control mice. The scale bar in FIG. 8A represents 5 mm. FIG. 8B shows results of dark-field observation of unstained horizontal sections of the fore-brain. Neither of the mice had detectable abnormality in the anterior and posterior branches of the anterior commissures (aAC and pAC). The scale bar in FIG. 8B represents 1 mm. FIG. 8C shows results of dark-field observation of the lumbar spinal cord. Ventral extensions (arrowhead) of the dorsal funiculus in mfy are shorter than those in control mice. The scale bar in FIG. 8C represents 250 μm.

2. Re-crossing of CST Axons at the Spinal Cord Midline in mfy/mfy Mice

Figure 1B:
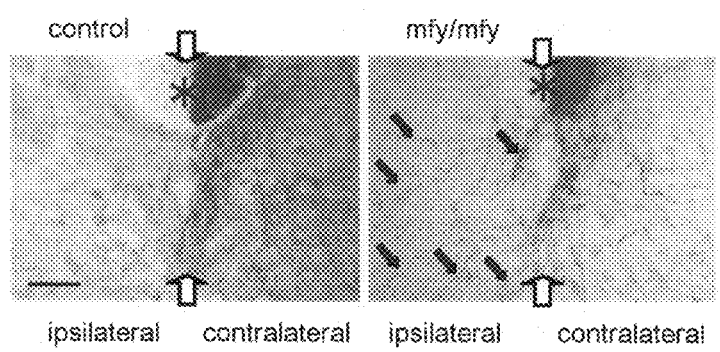
FIG. 1B is a diagram showing abnormal CST axon guidance in mfy and is a diagram showing results of anterograde tracings of CST axons using biotinylated dextran amine (BDA).
Figure 1C:
FIG. 1C is a diagram showing abnormal CST axon guidance in mfy and is a schematic diagram of CST axons in the spinal cord.
Figure 1D:
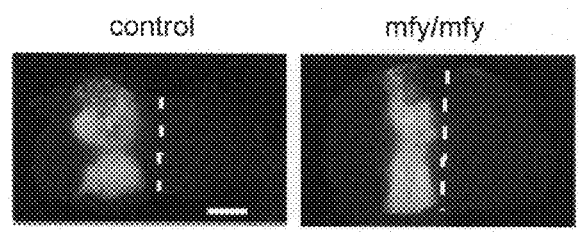
FIG. 1D is a diagram showing abnormal CST axon guidance in mfy and is a diagram showing results of unilaterally injecting a fluorescent retrograde tracer cholera toxin B (CTB) into the lumbar spinal cord.
Figure 1E:
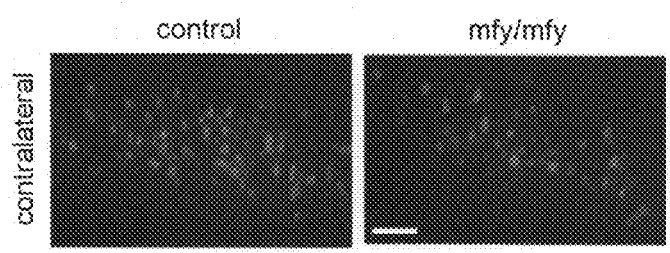
FIG. 1E is a diagram showing abnormal CST axon guidance in mfy and is a diagram showing the location of labeled cells in the motor cortex layer V.
Figure 1F:
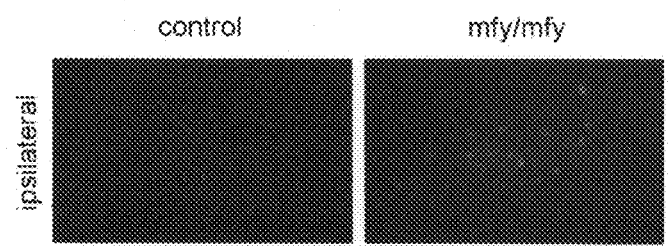
FIG. 1F is a diagram showing abnormal CST axon guidance in mfy and is a diagram showing the location of labeled cells in the motor cortex layer V.
Figure 1G:
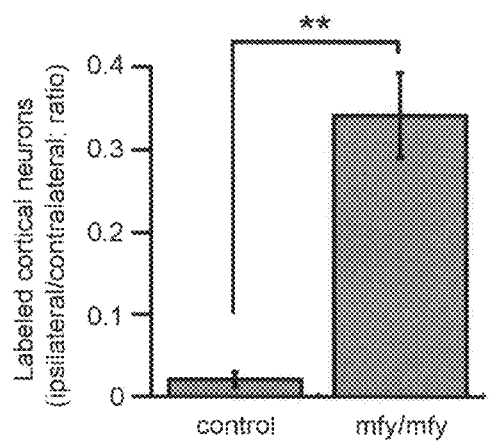
FIG. 1G is a diagram showing abnormal CST axon guidance in mfy and is a diagram showing the ipsilateral/contralateral ratio of the numbers of labeled cells.

The CST axons regulate spinal peripheral motor neurons via direct or indirect contact Pang et al., 1991, J. Comp. Neurol. 311, 356-366). To visualize these axons, an anterograde tracer was injected into the motor cortex, and CST projections were analyzed in the medulla and spinal cord. CST axons arising from the left cortex crossed the midline at the medulla in both mfy and control mice, and projected into the right side (FIG. 8D). However, in the spinal cord of control mice, CST axons projected only into the contralateral (right) gray matter and barely re-crossed the midline into the ipsilateral (left) gray matter. By contrast, aberrant midline re-crossing of these axons was observed in all of the spinal cords of mfy (n=7; FIGS. 1B and 1C). To reconfirm the anterograde tracing results, a retrograde tracer was unilaterally injected into the lumbar spinal cord (FIG. 1D). In wild-type mice, most of the retrograde-labeled CST neurons were located in layer V of the contralateral cortex (FIG. 1E). However, in mfy/mfy mice, the ipsilateral cortex also contained many labeled neurons (FIG. 1F). Cell-count analysis of the motor cortex revealed that the ipsilateral/contralateral ratio of the numbers of labeled cells was 2.02±0.92% for wild-type (n=4) mice and 34.26±5.22% times for mfy/mfy (n=7) mice, which was statistically significant (p<0.002; FIG. 1G).

FIG. 8 shows abnormal morphology in the spinal cord of mfy. FIG. 8D shows results of unilaterally injecting an anterograde tracer into the motor cortex and analyzing CST axons at medulla levels. In both of the mice, CST axons not only crossed the midline (arrowhead) but also shifted from the ventral (blue arrow pointing diagonally down to the right in FIG. 8D) to dorsal (red arrow pointing diagonally up to the left in FIG. 8D) sides. The scale bar in FIG. 8D represents 400 μm.

FIG. 1 shows walking of the novel mutant mice "miffy (mfy)" and abnormal CST axon guidance in mfy.

FIG. 1A shows one example of hind-limb footprint patterns. Hind limbs were pained with black ink, and the mice were placed on white paper to obtain their footprint patterns. FIG. 1B shows results of anterograde tracings of CST axons using biotinylated dextran amine (BDA) and sectioning at cervical levels of the spinal cord. CST axons descending the dorsal funiculus (asterisk) on the contralateral side to the tracer injection projected into the grey matter in both mfy and control mice. However, only in the mfy mice, many CST axons (blue arrow pointing diagonally down to the right) re-crossed the midline (white arrow). FIG. 1C shows a schematic diagram of CST axons (red curve coming from the central upper portion of the spinal cord) in the spinal cord. FIG. 1D shows results of unilaterally injecting a fluorescent retrograde tracer cholera toxin B (CTB) into the lumbar spinal cord. FIGS. 1E and 1F show that in the motor cortex layer V of wild-type mice, most of the labeled cells were located in the contralateral side. FIG. 1E shows that in mfy/mfy mice, the ipsilateral side also contained many labeled cells. FIG. 1G shows that the ipsilateral/contralateral ratio of the numbers of labeled cells in mfy mice (n=7) was significantly higher than that of control mice (n=4). Data are presented as the mean±standard deviation: Student's t-test, p<0.002. The scale bar in the drawing represents 100 μm.

3. Abnormal Spinal CPG Axon Guidance in mfy Mice

A tracer was unilaterally injected into the ventral side of the spinal cords of 4-day-old mfy and control mice. In the mfy mice, most of axons presumably derived from ipsilateral-projecting interneurons were found to cross the midline (FIG. 2, quantitative analysis results are shown in FIGS. 9B and 9C).

Figure 2:
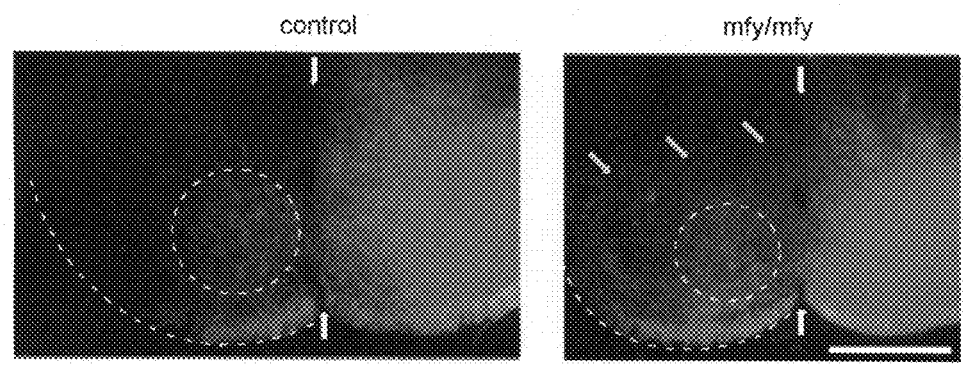
FIG. 2 is a diagram showing CST axon guidance in mfy.

In FIG. 2, transverse spinal cord sections (100 μm thick) at the L2 level were prepared by unilaterally applying DiI on the ventral side of L4. More neuronal fibers (diagonal yellow arrow) presumably derived from ipsilateral-projecting interneurons were observed to cross the midline (white arrow) into the contralateral (left) side in the mfy mouse spinal cords than in the control mouse spinal cords. The cell bodies (dotted circle) of descending commissural interneurons were indistinguishable. The scale bar in FIG. 2 represents 500 μm.

Figure 9A:
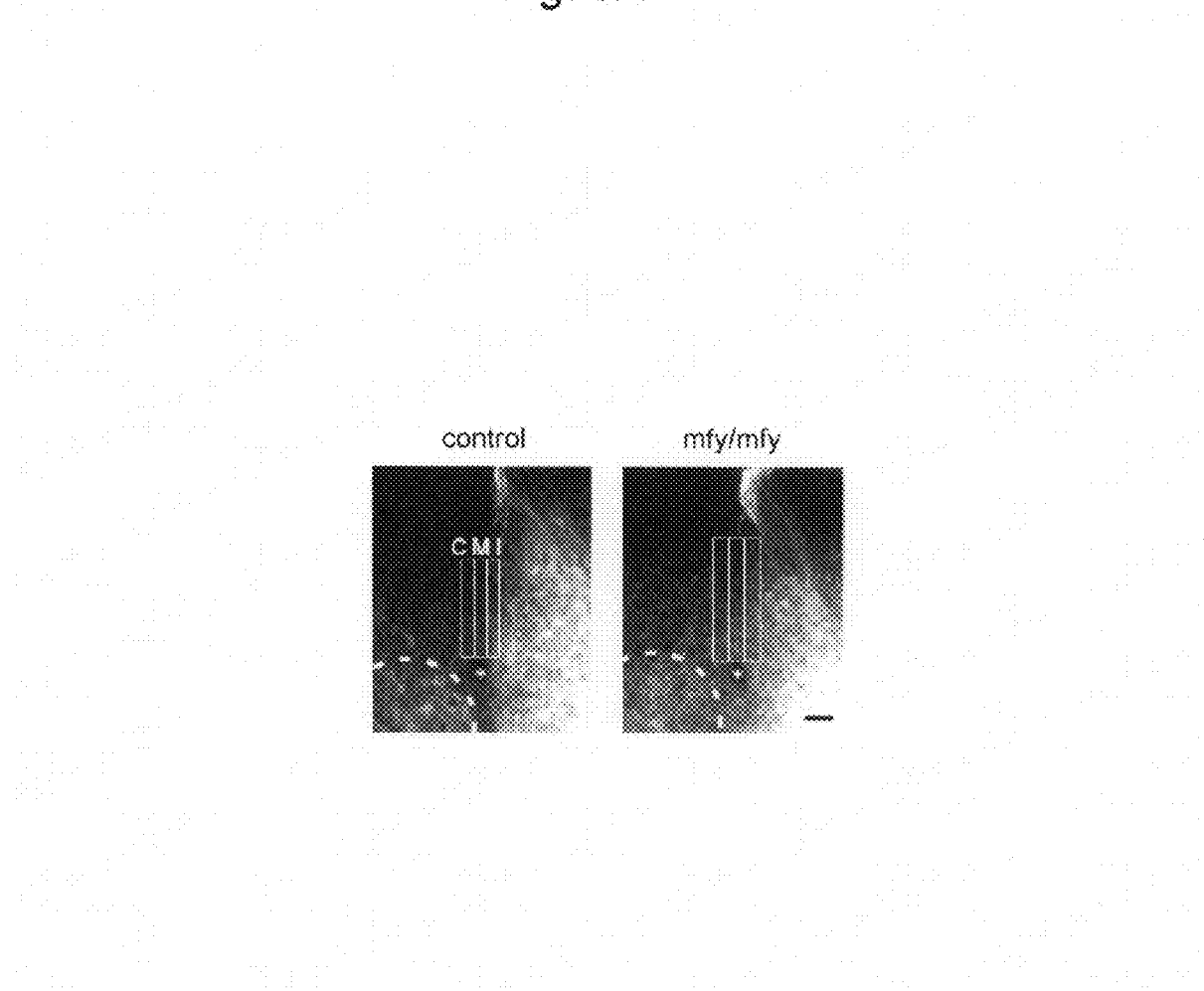
FIG. 9A is a diagram showing results of quantitative analysis of midline crossing of spinal local circuit neurons.
Figure 9B:
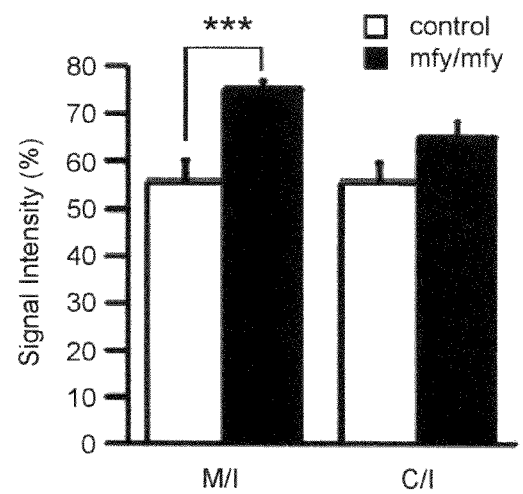
FIG. 9B is a diagram showing results of quantitative analysis of midline crossing of spinal local circuit neurons.
Figure 9C:
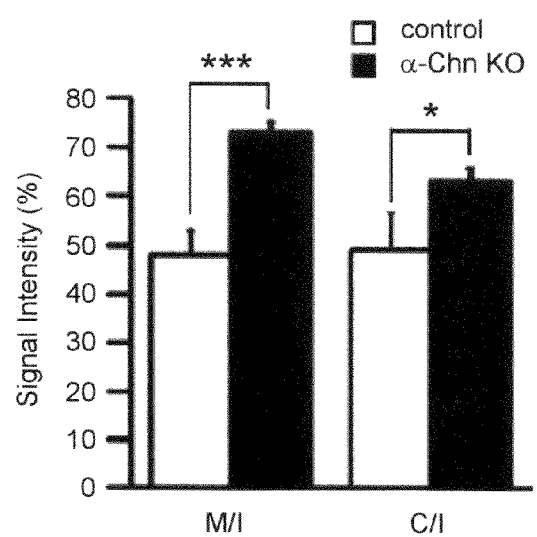
FIG. 9C is a diagram showing results of quantitative analysis of midline crossing of spinal local circuit neurons.

FIG. 9 shows results of quantitative analysis of midline crossing of spinal local circuit neurons. FIG. 9A shows results of measuring fluorescence signal intensity in the dorsal midline (M) of a 100 μm-thick spinal cord section unilaterally labeled with DiI (see FIG. 2D) and in its adjacent contralateral (C) and ipsilateral (I) grey matters. To minimize the influence of fluorescence derived from descending commissural fibers (dotted line), measurement was not performed on the ventral side of the central canal (asterisk). An area with the vertical length between the dorsal funiculus and the central canal and the width of the central canal as a horizontal width was measured. The width of the central canal was almost indistinguishable between control and mfy mice. The mean±standard deviation was 63.54±5.10 μm for control (n=6) and 78.24±5.12 μm for mfy (n=9) at P4 (p>0.05). The scale bar represents 100 μm. FIG. 9B shows results of comparing the ratios (M/I and C/I) of measurement values between control and mfy. The M/I ratio in mfy/mfy (n=9) was significantly higher than that in wild-type (n=6) (***p<0.001). The C/I ratio showed no statistically significant difference between them, but displayed similar trends (p>0.05). The significant difference was tested by unpaired Student's t-test.

4. The mfy Locus Encodes Rac-specific GAP α-Chimerin

Figure 3A:
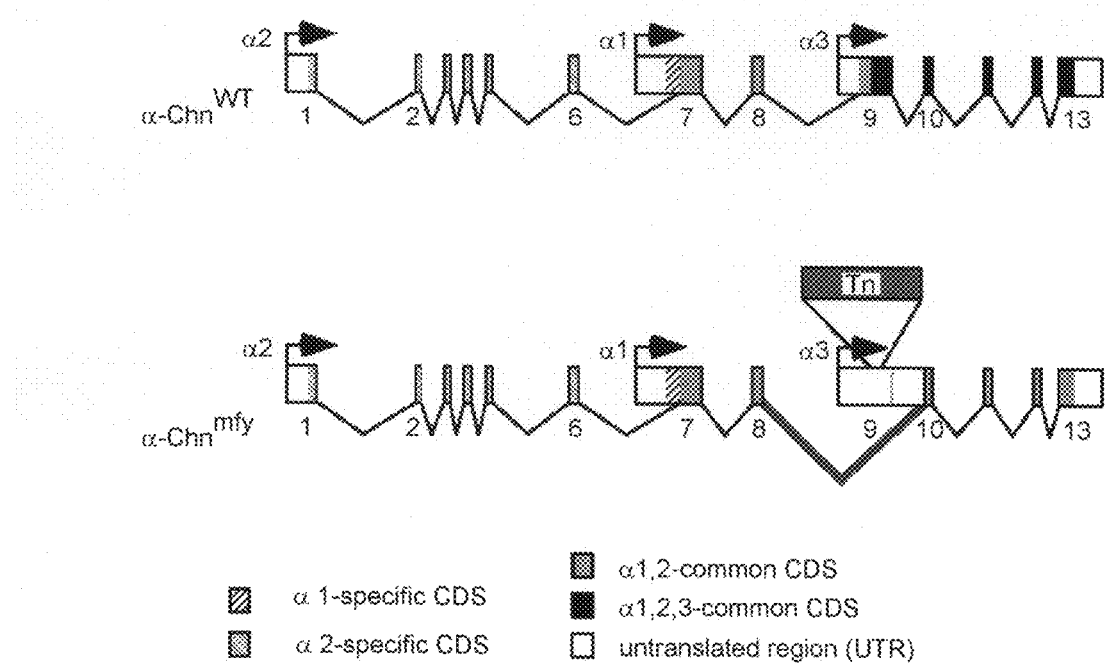
FIG. 3A is a schematic diagram of exon-intron structures of wild-type and mfy α1-Chn, α2-Chn, and α3-Chn splicing isoforms.
Figure 3B:
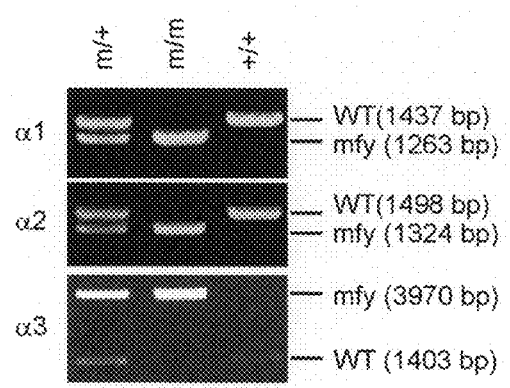
FIG. 3B is a diagram showing results of electrophoresis of RT-PCR products.
Figure 3C:
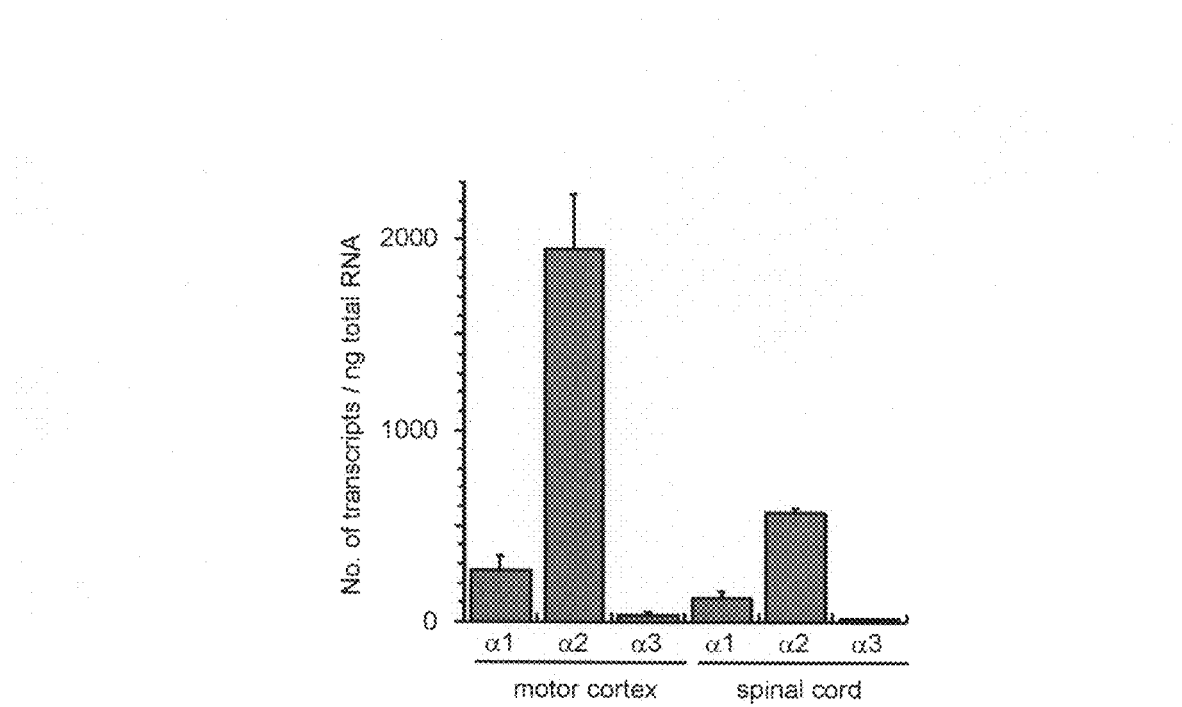
FIG. 3C is a diagram showing results of quantitative RT-PCR using the motor cortex and spinal cord of wild-type mice at P4.
Figure 3D:
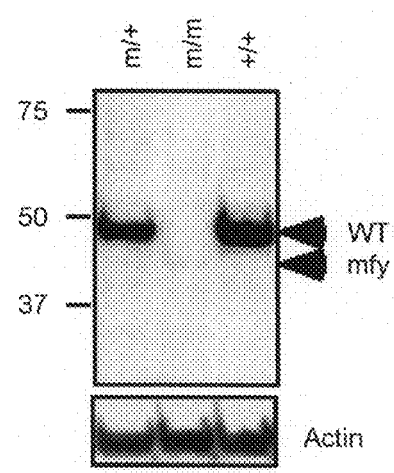
FIG. 3D is a diagram showing results of western blot using an α2-chimerin-specific antibody.
Figure 3E:
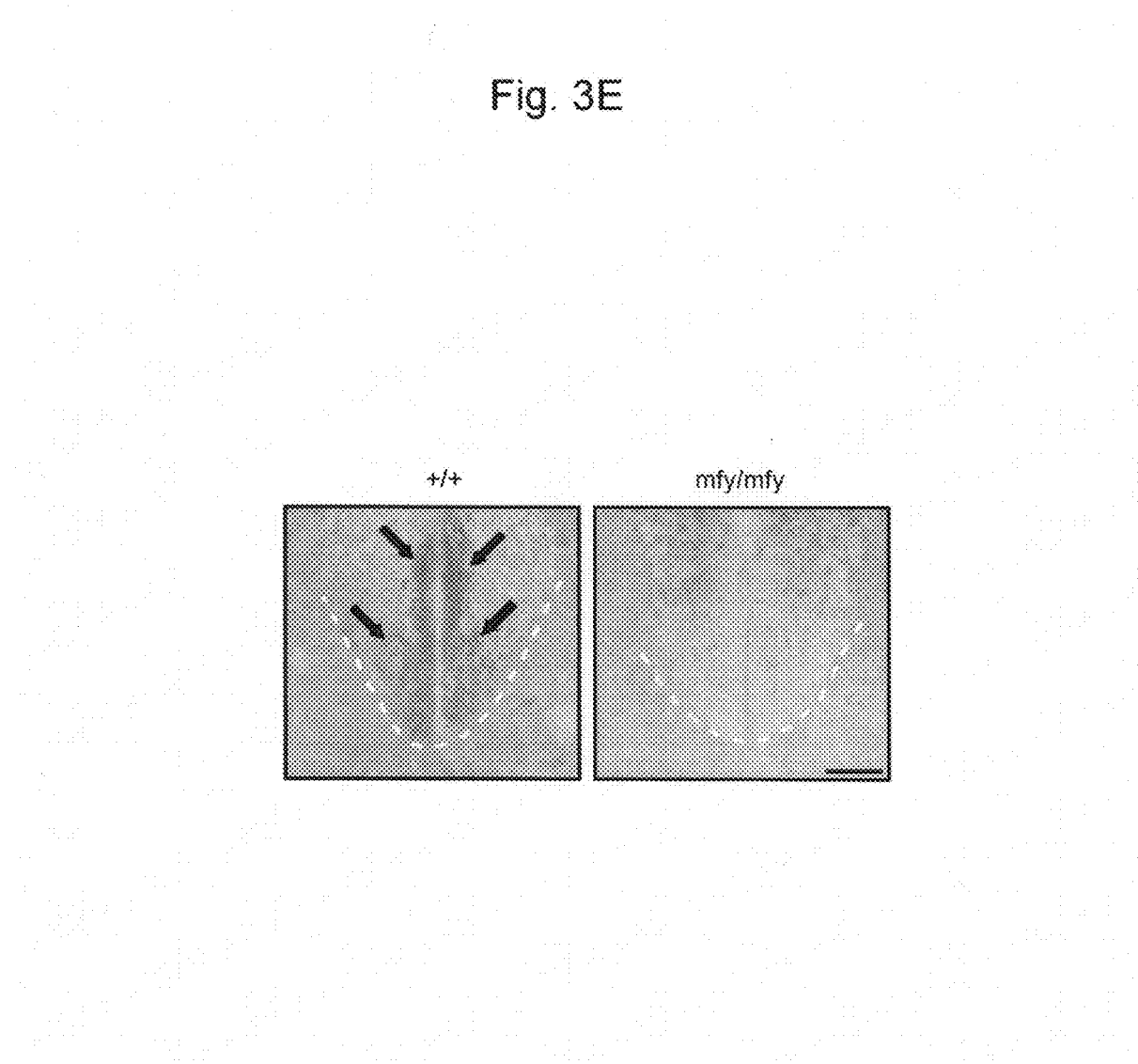
FIG. 3E is a diagram showing results of immunohistochemistry using an α2-chimerin-specific antibody.
Figure 11A:
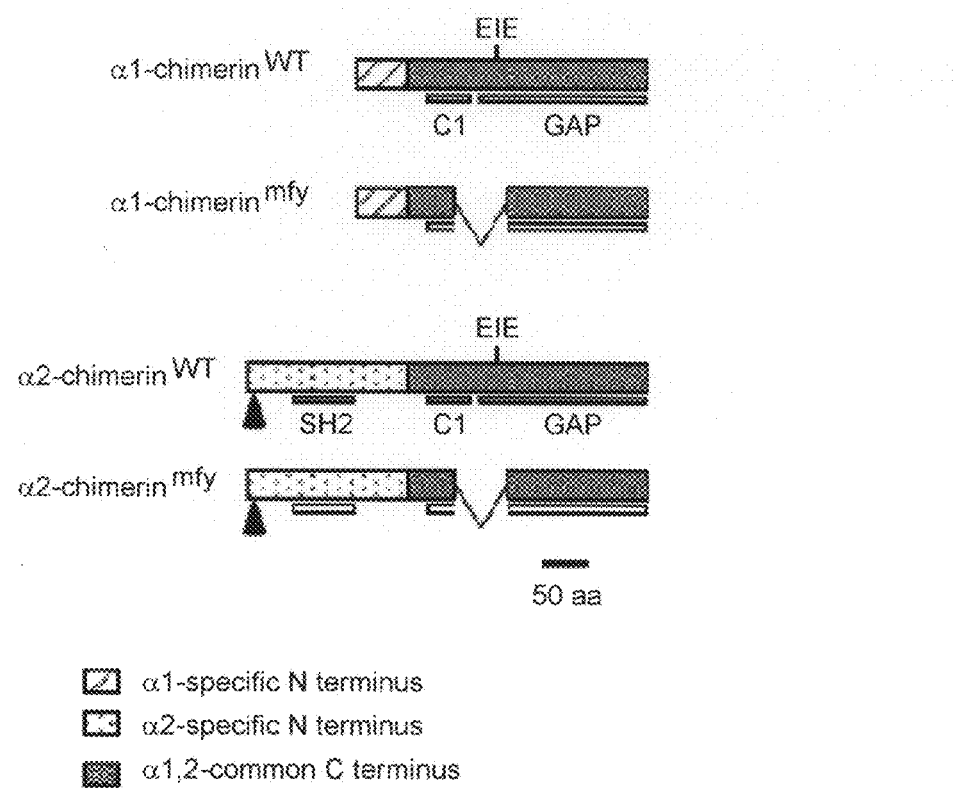
FIG. 11A is a schematic diagram of wild-type and mfy α1 and α2 isoforms.
Figure 11B:
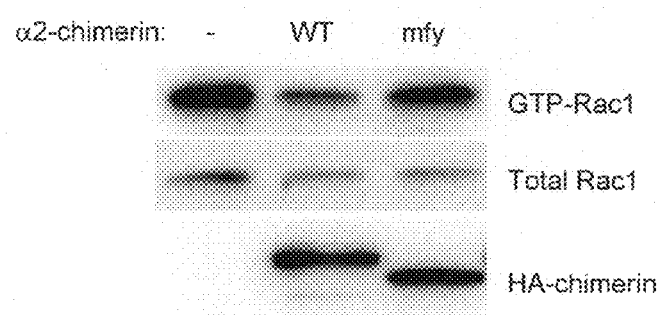
FIG. 11B is a diagram showing the Rac1-GAP activity of mfy α2-chimerin.
Figure 11C:
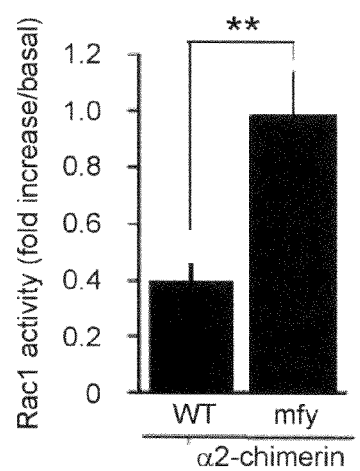
FIG. 11C is a diagram showing the Rac1-GAP activity of mfy α2-chimerin.

To locate the mfy mutation, microsatellites and SNPs that can distinguish between the alleles of two inbred strains, DBA/2 (DBA) and C57BL/6 (B6), were used. The mfy mutant was identified and maintained in a B6 background. Thus, mfy mice were crossed with wild-type DBA mice to obtain mfy/+ mice in a B6/DBA F1 background. These F1 mice were backcrossed to mfy/mfy mice, and their 299 progeny were genotyped, thereby finding that the mfy mutation was located between SNPs rs13476571 and rs13459064 on chromosome 2 (FIG. 10). Thirty genes are known within this 3.27-Mb interval (Table 1). Among them, 10 genes were excluded, because their knockout mouse lines have been previously reported to have normal gaits (Table 1). The transcript sizes and levels of the remaining 20 genes were compared between wild-type and mfy. This experiment was conducted by RT-PCR using primers amplifying P5 cDNA between the 5' and 3' untranslated regions (UTRs). As a result, it was found that the transcripts of only the α-chimerin (α-Chn) gene differed in size (FIGS. 3A and 3B, Table 1). α-chimerin is a Rho-GAP that is specific for Rac, a positive regulator of actin polymerization (Diekmann et al., 1991, Nature 351, 400-402; Hall et al., 1990, J. Mol. Biol. 211, 11-16; and Hall et al., 1993, Mol. Cell Biol. 13, 4986-4998). Recent reports using over-expression or siRNA-mediated knock-down in cultured neurons or tissue slices suggest that α-chimerin is involved in regulating dendritic morphology and spine density (Buttery et al., 2006, Proc. Natl. Acad. Sci. USA 103, 1924-1929; and Van de Ven et al., 2005, J. Neurosci. 25, 9488-9496). Its involvement in semaphoring 3A-induced growth-cone collapse has also been reported (Brown et al., 2004, J. Neurosci. 24, 8994-9004). However, the function of α-chimerin in vivo remains unknown.

α-Chn is known to have two splicing isoforms: α1 and α2 (Hall et al., 1990, J. Mol. Biol. 211, 11-16; and Hall et al., 1993, Mol. Cell Biol. 13, 4986-4998). A comparison of the nucleotide sequences of wild-type and mfy α1-Chn and α2-Chn cDNAs revealed that exon 9 (174 base pairs (bp)) was deleted in α1-Chn and α2-Chn of mfy. Exon 9 encodes 58 amino acids, three of which (EIE) are known to be essential for the Rac-GAP activity of α-chimerin (Ahmed et al., 1994, J. Biol. Chem. 269, 17642-17648). Mutant α2-chimerin was indeed confirmed to lack Rac-GAP activity (FIGS. 11A to 11C). In addition to the α1 and α2 isoforms, a novel isoform was identified and designated as α3. In transcripts of mutant α3-Chn, four nucleotides (GATG) of exon 9, including the putative initiation codon, were replaced with retroposon sequences, and intron 9 failed to be excised by splicing (FIG. 3A). The cloning and sequencing of the genomic DNA of mfy revealed an insertion of a retroposon into exon 9. This insertion appeared to impair both the donor and acceptor splicing functions for exon 9 (FIG. 3A). Quantitative RT-PCR using the motor cortex and spinal cord of wild-type mice at P4 revealed strong α2-Chn expression, weak α1-Chn expression, and little α3-Chn expression (FIG. 3C). Thus, subsequent analyses were focused on the α2 isoform. An α2-chimerin-specific polyclonal antibody was prepared, and it was confirmed by western blot that wild-type α2-chimerin was not detected in the brain of mfy (FIG. 3D). Furthermore, even mutant α2-chimerin was barely detected in the brain and spinal cord of mfy (FIGS. 3D and 3E), suggesting that endogenous mutant α2-chimerin is less unstable than mutant one over-expressed in cultured cells (FIG. 11B).

FIG. 10 shows gene mapping of mfy mutation. For linkage analysis, mfy mice (B6 background) were crossed with DBA/2 (DBA) mice, and the obtained F1 mice were further backcrossed to mfy mice. The obtained backcross progeny was genotyped using microsatellite markers (Mouse Genome Informatics) and SNPs (National Center for Biotechnology Information), and the determined genotypes were compared with phenotypes (gait patterns). The microsatellite markers and SNPs used are described in the left column in FIG. 10. The mouse phenotypes are described in the upper row in FIG. 10 (m=rabbit-like; +=normal; ND=not determined). The mfy locus was demonstrated to be located between D2Mit379 and D2Mit436. Then, all the mice were first analyzed using these two boundary markers. Only mice that displayed a recombination with these two markers were analyzed in more detail. Finally, the mfy locus was mapped to the 3.27-Mb interval between SNPs rs13476571 and rs13459064 on chromosome 2.

FIG. 3 shows α-chimerin Rac-GAP mutation in mfy. FIG. 3A shows schematic diagram of exon-intron structures of wild-type and mfy α1-Chn, α2-Chn, and α3-Chn splicing isoforms. In the mfy mutation, retroposon (Tn) insertion into exon 9 resulted in deletion (indicated by the red thick line in the drawing) of exon 9 (174 bp) in the α1 and α2 transcripts, and deletion of four nucleotides (including the putative initiation codon) and impairment of intron 9 splicing in the α3 transcript. CDS represents coding sequences. FIG. 3B shows results of electrophoresis of RT-PCR amplification products from between the 5' UTR and the 3' UTR of the α1-Chn, α2-Chn, and α3-Chn splicing isoforms in cDNAs derived from P5 WT (+/+), mfy/+ (m/+), and mfy/mfy (m/m) brains. PCR products were purified and cloned, and their nucleotide sequences were determined. FIG. 3C shows that α2-Chn expression predominated in the developing motor cortex and spinal cord. Quantitative RT-PCR was conducted using the motor cortex and spinal cord of wild-type mice at P4. All data are presented as the mean±standard deviation (n=3 mice). FIG. 3D shows results of western blot using an α2-chimerin-specific antibody. Wild-type α2-chimerin proteins were not detected in mfy mice. Unexpectedly, even expression of mfy α2-chimerin was barely detected in the mfy mice. Total lysates prepared from the P10 mouse telencephalon were used. FIG. 3E shows results of immunohistochemistry using an α2-chimerin-specific antibody. Strong expression of α2-chimerin proteins was detected (arrow) in the CST of the dorsal funiculus (dotted line) of the wild-type spinal cord. This result suggests that α2-chimerin functions in developing CST. α2-chimerin was not detected in the mfy mouse spinal cord. The scale bar in the drawing represents 50 μm.

FIG. 11 shows disruption of the Rac1-GAP activity of mfy α2-chimerin. FIG. 11A shows a schematic diagram of WT and mfy α1 and α2 isoforms. The C-terminus having the C1 and GAP domains are common to α1 and α2 isoforms. By contrast, the N-terminus is specific to each isoform, and the α2 N-terminus contains the SH2 domain. A comparison of the nucleotide sequences of wild-type and mfy transcripts revealed that exon 9 (174 base pairs (bp)) was deleted in the α1-Chn and α2-Chn transcripts of mfy (FIG. 3A). Exon 9 encodes 58 amino acids including the amino acid sequence (EIE) essential for GAP activity. Polyclonal antibodies were prepared using α2 N-terminal 17 amino acids (arrowhead). In FIG. 11B, COS cells were transfected with the indicated plasmid. Cell lysates were incubated with GST-fusion proteins of the Rac1-bound domain of pPak. Bound and total proteins were analyzed by SDS-PAGE and immunoblot. A GTP-bound Rac1 level was measured and normalized to the corresponding total Rac1 level. FIG. 11C shows that Rac1 was inactivated by wild-type α2-chimerin but not by mfy α2-chimerin. Rac1 activity is indicated by a ratio to the basal level in untransfected COS cells. All data are presented as means and standard deviations. n=8 (WT) or 4 (mfy). (**p<0.01, Student's t-test).

5. Improved Walking of mfy Mice Expressing Tg-α-Chimerin

Figure 4A:
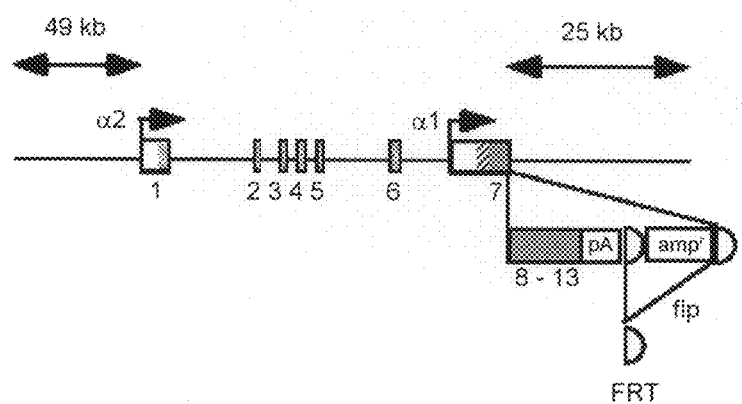
FIG. 4A is a schematic diagram of a Bac Tg construct.
Figure 4B:
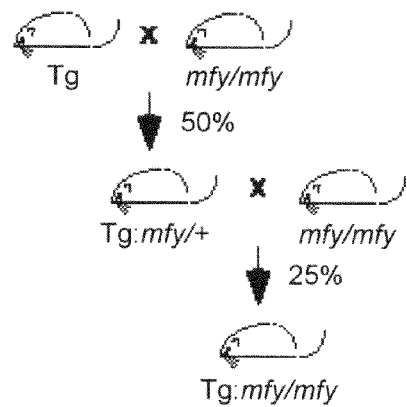
FIG. 4B is a diagram showing preparation of Tg mice.

To confirm that α-chimerin causes the mfy mutation, whether Tg expression of α-chimerin can rescue the mfy phenotype was analyzed. A BAC clone that covered the 49-kb upstream region and exons 1 to 7 of α-chimerin was modified using a Red/ET system to prepare a BAC-α-chimerin construct. In the construct, exon 7 was followed by cDNA encoding exons 8 to 13 and a poly(A) signal (FIG. 4A). BAC transgenic mice of two strains (#539 and #883) were prepared by microinjecting the construct into pronuclei in fertilized eggs. The transgenic mice were further crossed with mfy mice to prepare transgenic mice in the mfy background (FIG. 4B).

Figure 4C:
FIG. 4C is a diagram showing improved walking of Tg#883:mfy/mfy mice.
Figure 12A:
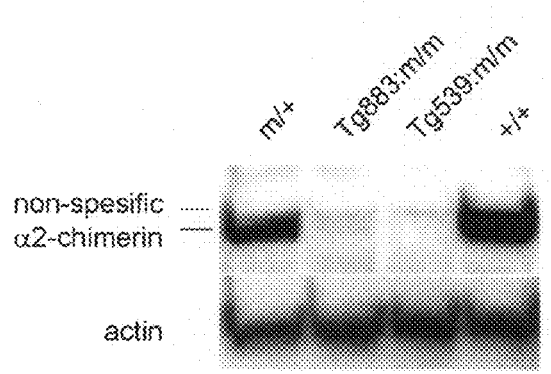
FIG. 12A is a diagram showing results of western blot analysis of α2-chimerin protein levels in Tg:mfy/mfy and α-Chn-KO mice.
Figure 12B:
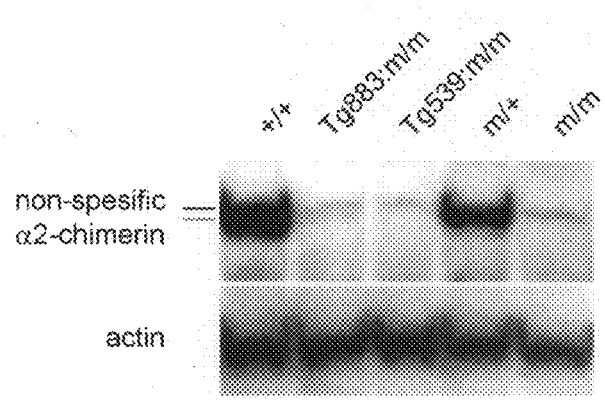
FIG. 12B is a diagram showing results of western blot analysis of α2-chimerin protein levels in Tg:mfy/mfy and α-Chn-KO mice.
Figure 12C:
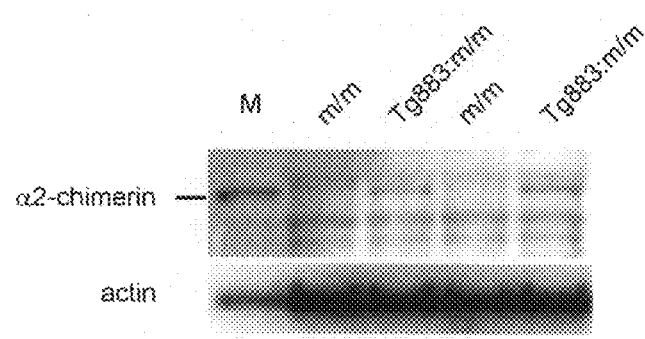
FIG. 12C is a diagram showing results of western blot analysis of α2-chimerin protein levels in Tg:mfy/mfy and α-Chn-KO mice.

No improvements were observed in the gaits of the Tg#539: mfy/mfy mice. This is consistent with the fact that α-chimerin expression was not detected in these mice (FIGS. 12A and 12B). By contrast, considerable improvement was observed in the gaits of the Tg#883:mfy/mfy mice (FIG. 4C). The mean±SEM proportion of left-right synchronized gaits in 40 randomly selected gaits of Tg#883:mfy/mfy mice (n=13) analyzed was 53.65±6.56%, which was substantially less than in mfy/mfy mice (n=6, 99.58±0.42%; $p<0.0001$, unpaired t-test). α-chimerin proteins were observed to be weakly expressed in Tg#883:mfy/mfy mice (FIGS. 12A to 12C). This is consistent with the moderate rescue in the mice. These results strongly suggest that α-chimerin is the causal gene of the mfy mutation.

FIG. 4 shows that disruption of α-Chn causes the mfy phenotype. FIG. 4A shows a schematic diagram of the Bac Tg construct. A cDNA fragment containing exons 8 to 13, a poly(A) signal, and a drug resistance marker flanked by two FRT sites was inserted immediately after exon 7 of a BAC clone using Red/ET recombination in E. coli. The drug resistance marker was removed therefrom by expressing flp recombinase in the E. coli clone. In the experiment shown in FIG. 4B, transgenic mouse strains were prepared by injecting the linearized construct into fertilized mouse eggs. Mice of two strains were prepared and crossed with mfy mice to prepare transgenic mice in the mfy background. FIG. 4C is a diagram showing improved walking of Tg#883:mfy/mfy mice.

FIG. 12 shows results of western blot analysis of α2-chimerin protein levels in Tg:mfy/mfy and α-Chn-KO mice. FIGS. 12A and 12B respectively show results of blotting total lysates derived from the adult mouse telencephalon with anti-α2-chimerin and anti-actin antibodies. Wild-type α2-chimerin was not detected in Tg#539:mfy/mfy mice, as in the mfy/mfy (m/m) mice. This is consistent with the result showing no detectable improvements in the gaits of the mice. The mean±standard deviation proportion of left-right synchronized movement of hind limbs in 40 randomly selected gaits of Tg#539:mfy/mfy mice (n=11) was 99.09±0.51%, which was indistinguishable from their littermate mfy control group (n=5, 100%) ($p>0.2$). By contrast, wild-type α2-chimerin proteins derived from Tg were detected, albeit at low levels, in Tg#883:mfy/mfy mice. This result is consistent with the result showing moderate improvement in the gaits of Tg#883: mfy/mfy mice. As shown in FIG. 12C, wild-type α2-chimerin proteins were also detected in lysates from the whole brain of Tg#883:mfy/mfy mice at P7. In FIG. 12C, M represents results obtained with a small amount of wild-type mouse-derived total lysates used as a size marker for wild-type α2-chimerin proteins.

6. Preparation and Analysis of α-Chn-KO Mice

Figure 4D:
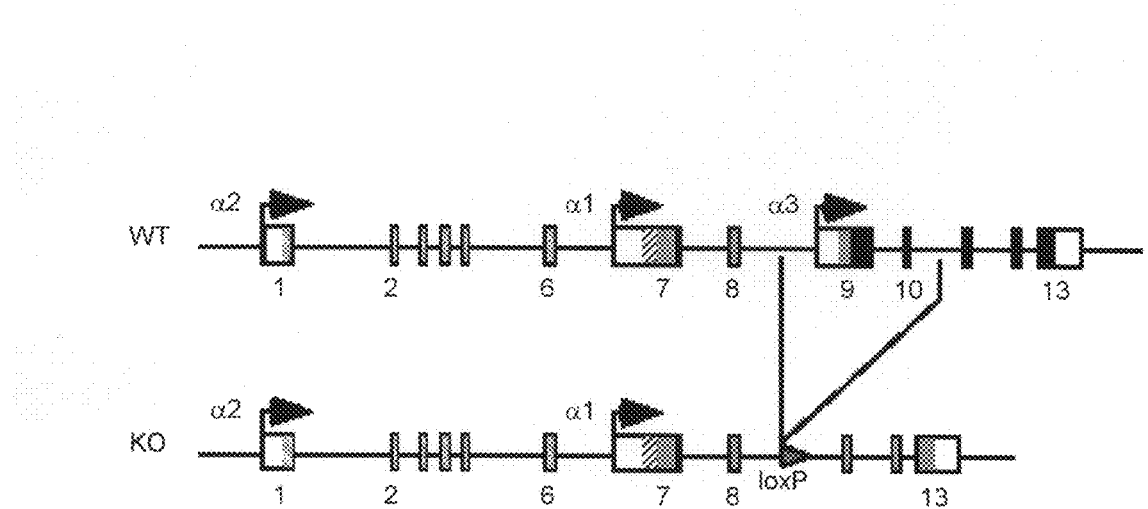
FIG. 4D is a schematic diagram of the KO locus in knock-out mice.
Figure 4E:
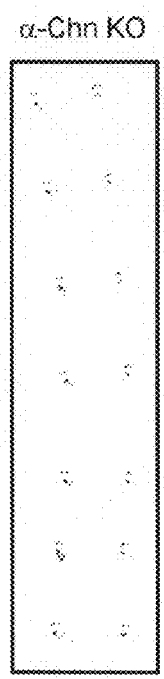
FIG. 4E is a diagram showing hind-limb footprint patterns of α-Chn-KO mice.
Figure 12D:
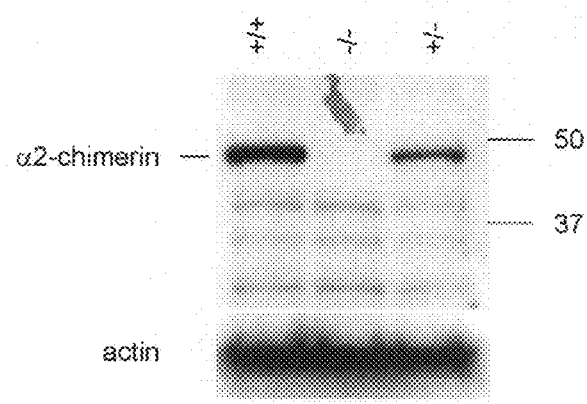
FIG. 12D is a diagram showing results of western blot analysis of α2-chimerin protein levels in Tg:mfy/mfy and α-Chn-KO mice.

To further confirm that α-chimerin is the causal gene of the mfy mutation, exons 9 and 10 were deleted from the α-chimerin allele by homologous recombination in ES cells and Cre/loxP recombination in the mouse germline to prepare mice homozygous for the targeted allele (α-Chn-KO mice) (FIGS. 4D and 12D). The knockout mice had a rabbit-like gait (FIG. 4E). They also demonstrated midline crossing of CST (FIG. 4F) and CPG (FIG. 9C) axons in the spinal cord and a shorter length of the dorsal funiculus in the spinal cord. All of these phenotypes are similar to those of mfy mice. Taken together, it was concluded that α-chimerin is the causal gene of the mfy phenotype.

FIG. 4 shows that disruption of α-Chn causes the mfy phenotype. FIG. 4D shows a schematic diagram of the KO locus. Exons 9 and 10 were deleted by homologous recombination in ES cells and Cre/loxP recombination in the mouse germline. FIG. 4E shows hind-limb footprint patterns of α-Chn-KO mice showing gait patterns similar to those of mfy mice. FIG. 4F shows sections at cervical levels of the spinal cord in anterograde tracings of CST axons. The CST axons of α-Chn-KO mice re-crossed the spinal cord midline, as in mfy mice. The scale bar in the drawing represents 100 µm.

FIG. 12 shows results of western blot analysis of α2-chimerin protein levels in Tg:mfy/mfy and α-Chn-KO mice. FIG. 12D shows results of western blot using an α2-chimerin-specific antibody. The α-Chn-KO (−/−) mice were confirmed to lack wild-type α2-chimerin. Moreover, even the mutant proteins were barely detected.

FIG. 9 shows results of quantitative analysis of midline crossing of spinal local circuit neurons. FIG. 9C shows M/C and I/C ratios compared between α-Chn-KO (n=10) and control (WT or +/−) (n=5) mice. Both the M/I (***$p<0.001$) and C/I (*$p<0.05$) ratios were significantly higher in the knockout mice than in the control mice. The significant difference was tested by unpaired Student's t-test.

7. α-Chimerin Proteins are Present in CST

It is noteworthy that all of the phenotypes of mfy and α-chimerin-KO mice are identical to those reported for ephrinB- or EphA4-KO mice (Dottori et al., 1998, Proc. Natl. Acad. Sci. USA 95, 13248-13253; Kullander et al., 2003, Science 299, 1889-1892; Kullander et al., 2001, Genes Dev. 15, 877-888; and Yokoyama et al., 2001, Neuron 29, 85-97) and for mice expressing EphA4 lacking kinase activity (EphA4$^{FF/FF}$ and EphA4$^{KD/KD}$) (Kullander et al., 2001, Neuron 29, 73-84). By contrast, the anterior commissure, the formation of which is known to be dependent on EphA4 reverse signaling (Kullander et al., 2001, Neuron 29, 73-84), was normal in mfy mice (FIG. 8B). These results suggest that the mfy phenotype is likely to be attributed to abnormal ephrinB3/EphA4 forward signaling. Immunohistochemistry revealed that α2-chimerin is co-localized with EphA4 in the developing CST (FIGS. 13A and 13C). In α-chimerin-knockout mice, α2-chimerin proteins were not detected, but the levels of EphA4 proteins were unaltered (FIGS. 13B and 13D). It was also found that the α2-chimerin protein is present in the growth cones of cultured neurons prepared from the developing motor cortex (FIG. 14C). These results suggested that α-chimerin functions as a downstream mediator of ephrinB3/EphA4 forward signaling in developing CST axons.

Figure 13:
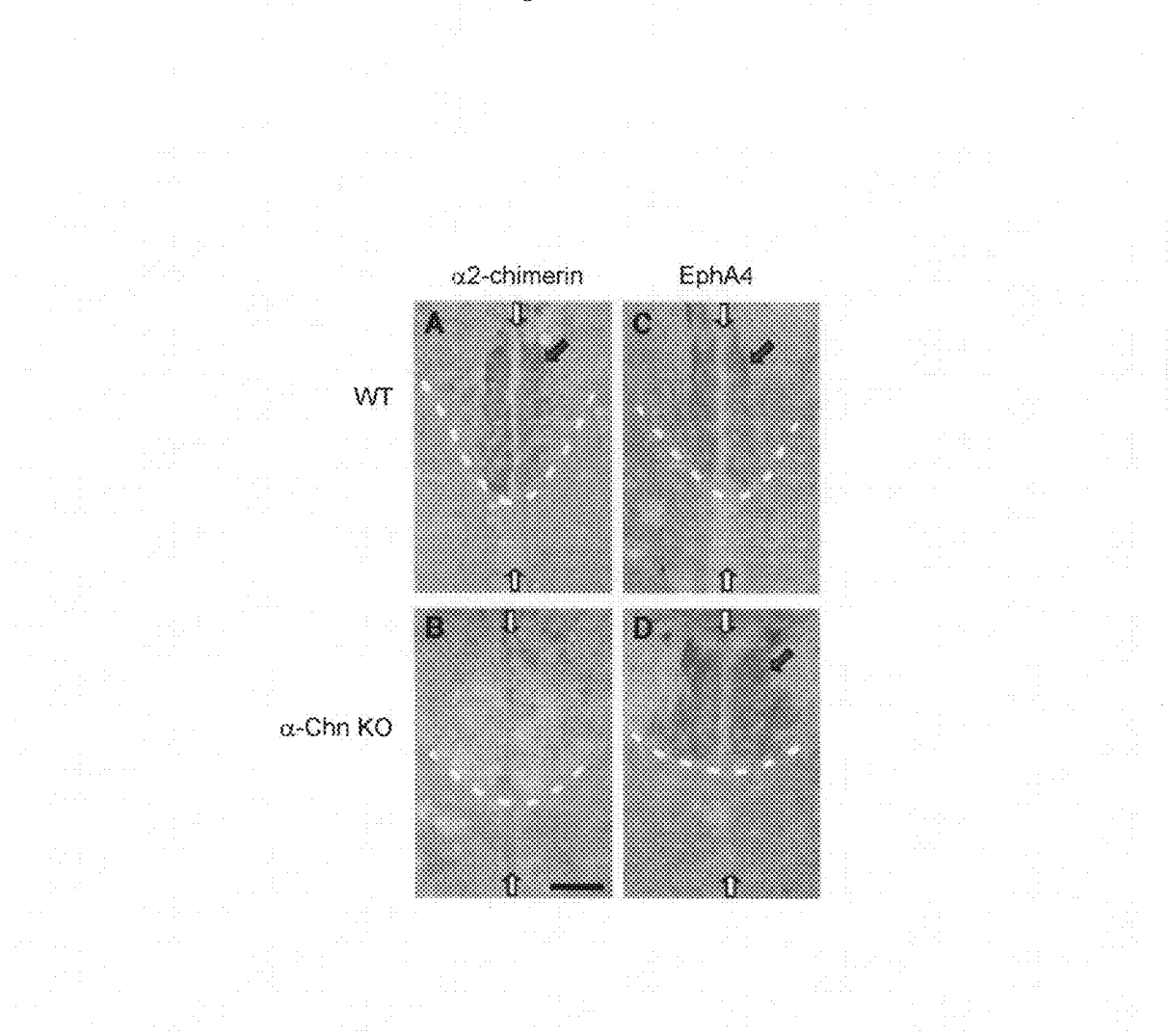
FIG. 13 is a diagram showing co-localization of α2-chimerin with EphA4 in developing CST.

FIG. 13 shows co-localization of α2-chimerin with EphA4 in developing CST. FIGS. 13A to 13D show results of immunohistochemistry of sections at cervical levels of the spinal cords of wild-type (FIGS. 13A and 13C) and α-Chn-KO (FIGS. 13B and 13D) mice at P11, using an α2-chimerin (FIGS. 13A and 13B) or EphA4 (FIGS. 13C and 13D)-specific antibody. In the wild-type spinal cord, co-localization of α2-chimerin and EphA4 was observed in CST (blue arrow) of the dorsal funiculus (dotted line). In the α-Chn-KO mouse spinal cord, α2-chimerin was not detected, but no reductions were observed in EphA4 expression. White arrow: midline. The scale bar in the drawing represents 50 µm.

Figure 14:
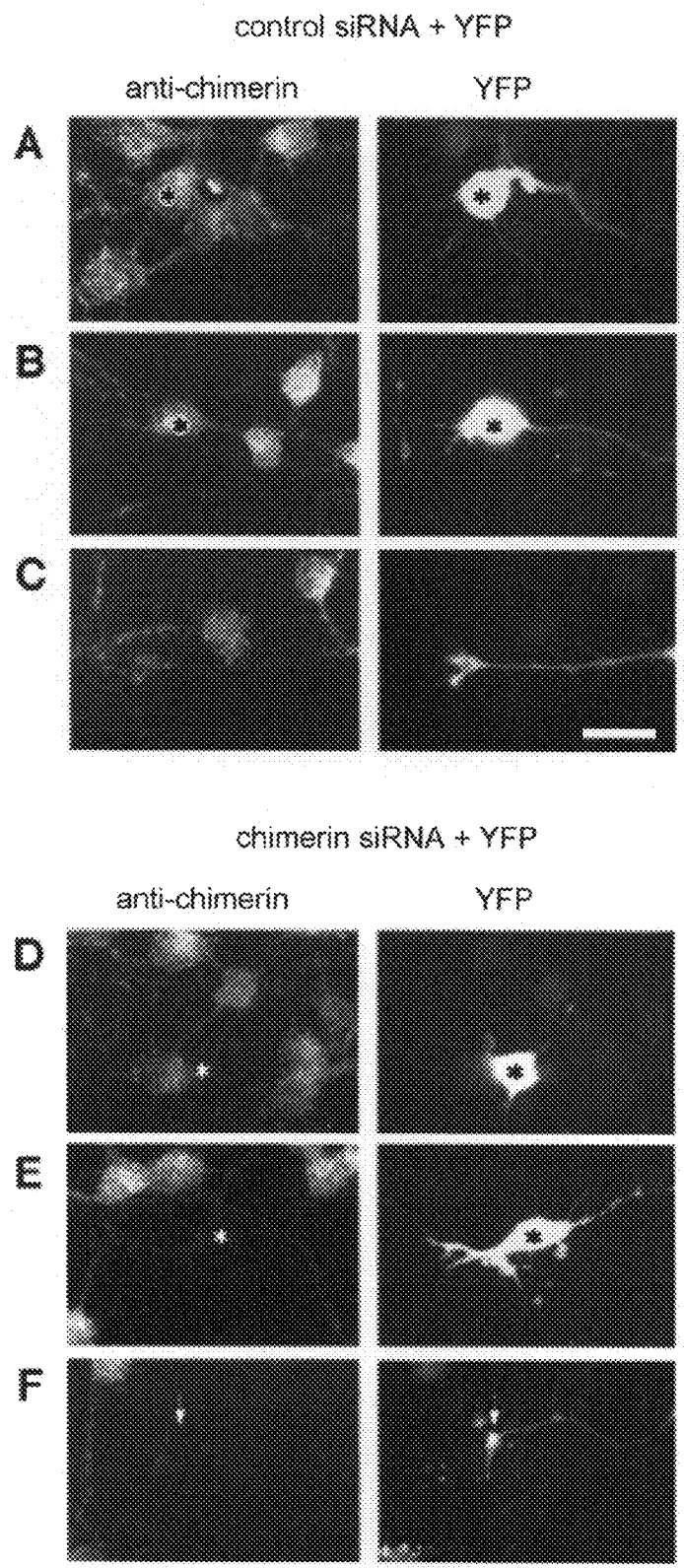
FIG. 14 is a diagram showing localization of α2-chimerin proteins in the cell bodies and growth cones of cultured cortical cells, and down-regulation of α2-chimerin proteins by siRNA.

FIG. 14 shows localization of α2-chimerin proteins in the cell bodies and growth cones of cultured cortical cells, and down-regulation of α2-chimerin proteins by siRNA. FIGS. 14A to 14C show results of immunostaining with an α2-chimerin-specific antibody. The results indicated that α-chimerin proteins are present in E18.5 rat-derived cell bodies (FIGS. 14A to 14C) and growth cones (FIG. 14C). The cells indicated by asterisks were transfected with a plasmid simultaneously expressing EYFP and control siRNA. FIGS. 14D to 14F show that the α-chimerin protein was detected in neither the cell bodies (asterisk: FIGS. 14D and 14E) nor growth cones (arrow: FIG. 14F) of neurons transfected with a plasmid simultaneously expressing EYFP and α-chimerin-specific siRNA. The scale bar in the drawing represents 50 μm.

8. Binding of α-chimerin and EphA

Figure 5A:
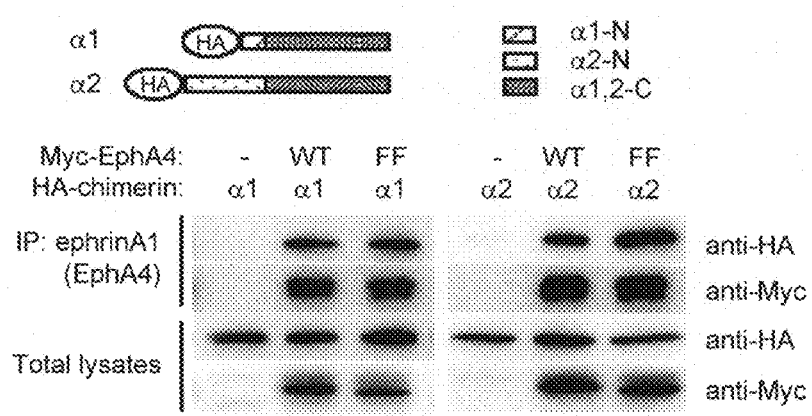
FIG. 5A is a diagram showing the binding of α1-chimerin and EphA4.
Figure 5B:
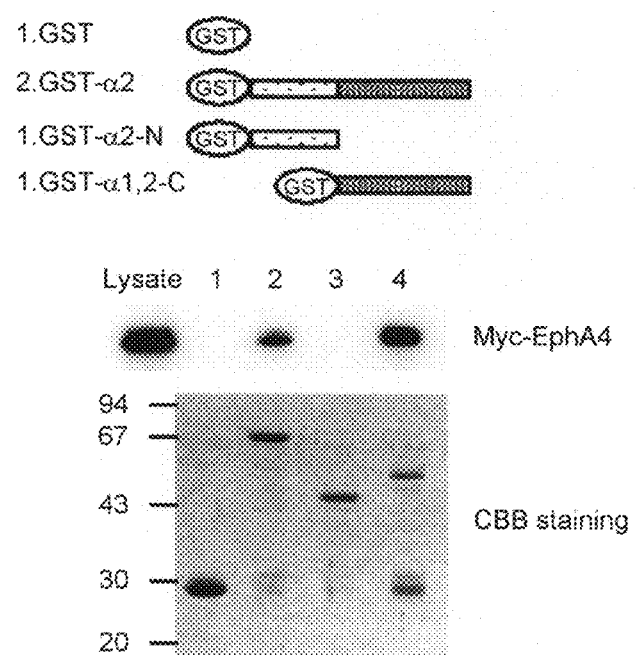
FIG. 5B is a diagram showing the binding of α-chimerin C-terminus and EphA4.
Figure 5C:
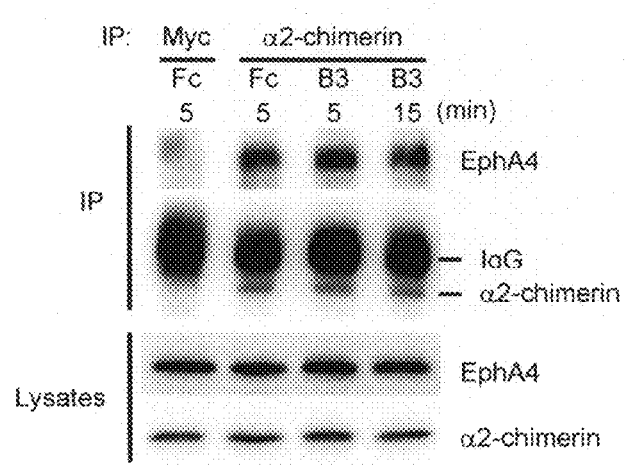
FIG. 5C is a diagram showing whether the binding of endogenous α-chimerin and EphA4 in neurons is enhanced by ephrinB3 stimulation.
Figure 5D:
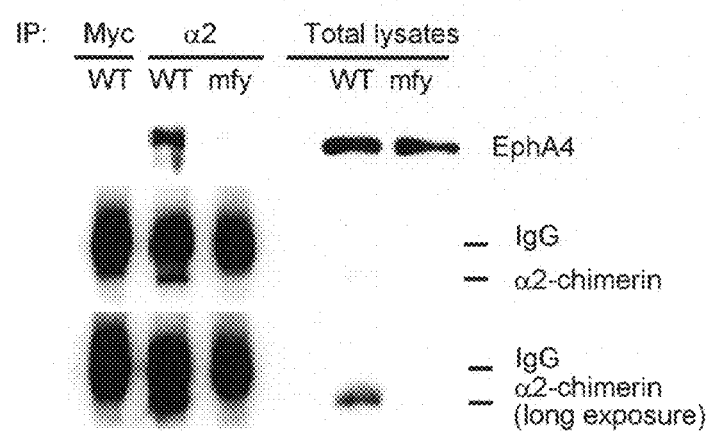
FIG. 5D is a diagram showing the binding of endogenous α-chimerin and EphA4 in the mouse brain.
Figure 15:
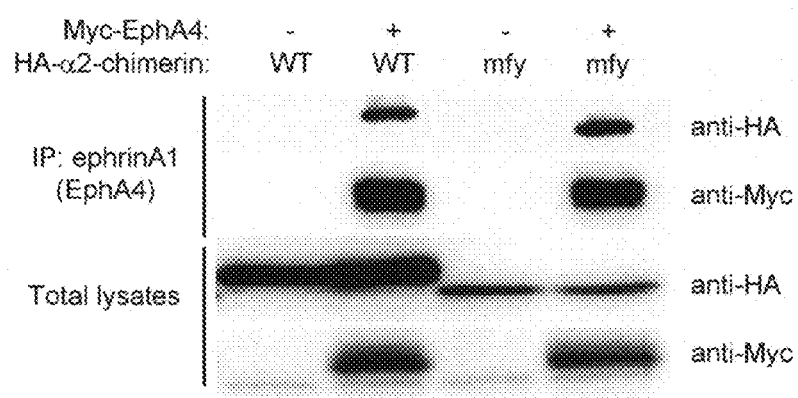
FIG. 15 is a diagram showing the Rac-GAP activity of α-chimerin required for the binding of EphA4 and α2-chimerin.

To test whether α-chimerin binds with EphA4, EphA4 and α-chimerin expression was caused in 293T cells, and EphA4 was immunoprecipitated from cell lysates using Fc region-fused ephrinA1. Both wild-type α1-chimerin and α2-chimerin were co-precipitated with wild-type EphA4 and EphA4 lacking kinase activity (FIG. 5A). mfy α2-chimerin was also co-precipitated with wild-type EphA4 (FIG. 15). These results suggested that α-chimerin binds with EphA4 in vitro, and that this binding requires neither the kinase activity of EphA4 nor the Rac-GAP activity of α-chimerin. To identify the region of α-chimerin responsible for the binding with EphA4, GST-fusion protein pull-down assay was conducted. EphA4 bound to full-length α2-chimerin and the α1- and α2-common C-terminus, but not to the α2-specific N-terminus (FIG. 5B). These results indicate that EphA4 binds with α1-chimerin and α2-chimerin at their common C-termini. Subsequently, whether α-chimerin binds with EphA4 in neurons, and, if so, whether ligand stimulation enhances the binding, were examined. EphA4 was co-immunoprecipitated with α2-chimerin without ephrinB3 stimulation, and the binding was not enhanced by stimulation with clustered ephrinB3 (FIG. 5C). These results indicate that α-chimerin binds with EphA4 in neurons, and that the binding is independent of ephrinB3 stimulation. Finally, lysates were prepared from the developing motor cortex of wild-type mice and immunoprecipitated using an α-chimerin-specific antibody. In this experiment as well, EphA4 bound with α2-chimerin (FIG. 5D).

FIG. 5 shows that α-chimerin binds with EphA4 and regulates Rac1 activity in response to ephrinB3→EphA4 forward signaling. FIG. 5A shows that EphA4 binds with α1-chimerin and α2-chimerin isoforms in vitro. EphA4$^{FF}$ lacking kinase activity also binds with both the isoforms. 293T cells were transfected with the indicated expression vector. Total lysates were precipitated with Fc region-fused ephrinA1, and α-chimerin and EphA4 were detected with anti-HA and anti-Myc antibodies, respectively. Total lysates were also blotted with anti-HA and anti-Myc antibodies. FIG. 5B shows that EphA4 bound with the α-chimerin C-terminus common to the α1 and α2 isoforms. For pull-down assay, lysates were prepared from HEK293T cells transfected with Myc-tagged EphA4, and supernatants were incubated with GST-fusion proteins of full-length or partial α2-chimerin and further incubated with glutathione-Sepharose beads. Bound proteins were detected by SDS-PAGE and immunoblot using an anti-Myc antibody. The lower panel shows results of Coomassie Brilliant Blue (CBB) staining of the GST-fusion proteins used in this experiment. FIG. 5C shows that endogenous α-chimerin and EphA4 bound with each other in neurons, and the binding was not enhanced by ephrinB3 stimulation. Cortical neurons prepared from E18.5 rats were stimulated with pre-clustered ephrinB3-Fc or control Fc for 5 minutes or 15 minutes. Bound and total proteins were detected with anti-EphA4 and anti-α2-chimerin antibodies. FIG. 5D shows that endogenous α-chimerin and EphA4 bound with each other in the mouse brain. Lysates from the P3 mouse cortex were immunoprecipitated with an anti-α2-chimerin or anti-Myc (negative control) antibody. The mfy cortex was also used as a second negative control. Bound and total proteins were detected with anti-EphA4 and anti-α2-chimerin antibodies.

FIG. 15 shows that the binding of EphA4 and α2-chimerin does not require the Rac-GAP activity of α-chimerin. EphA4 bound with mfy α2-chimerin in vitro. 293T cells were transfected with the indicated plasmid. Total lysates were precipitated with Fc region-fused ephrinA1. α-chimerin and EphA4 were detected by immunoprecipitating them with anti-HA and anti-Myc antibodies, respectively. Total lysates were also blotted with HA- and Myc-specific antibodies.

9. α-Chimerin Inactivates Rac in Response to EphrinB3/EphA4 Signaling

Figure 5E:
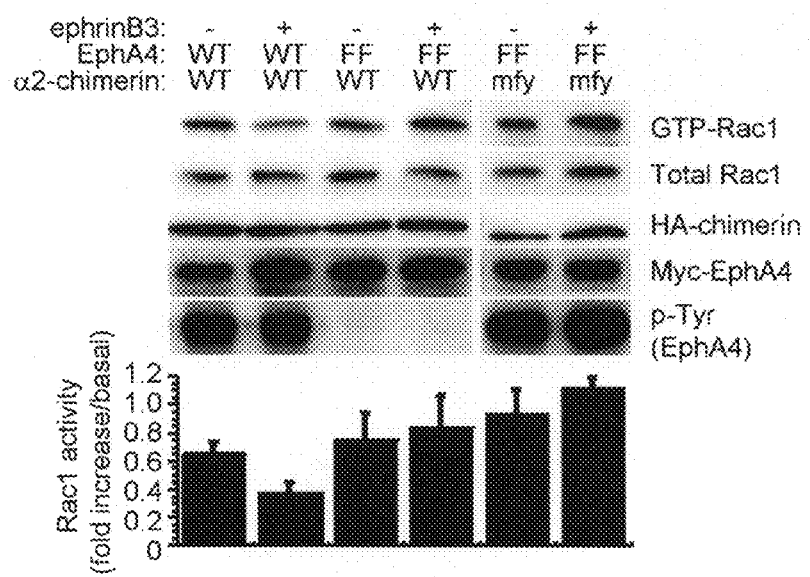
FIG. 5E is a diagram showing Rac1 activity.
Figure 5F:
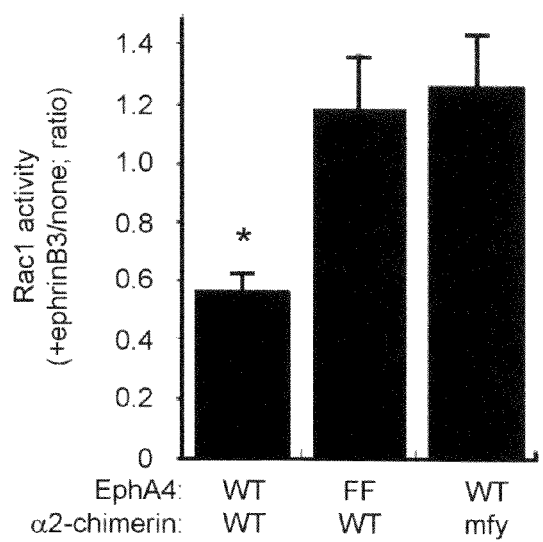
FIG. 5F is a diagram showing Rac1 activity.

No previous reports have suggested the involvement of α-chimerin in ephrin/Eph signaling. To analyze whether α-chimerin regulates Rac activity in response to ephrinB3/EphA4 forward signaling, EphA4 (wild-type or kinase dead) and α2-chimerin (wild-type and mfy) expression was caused in COS-7 cells, and Rac activity was measured before and after ephrin stimulation (FIG. 5E). EphrinB3 stimulation induced Rac inactivation in cells expressing both wild-type EphA4 and α-chimerin, but not in cells expressing mutant EphA4 and wild-type α-chimerin or wild-type EphA4 and mutant α-chimerin (FIG. 5F). These results indicate that both EphA4 kinase activity and functional α2-chimerin are essential for ephrinB3-induced Rac inactivation. It is noteworthy that the EphA4 proteins over-expressed in COS cells were phosphorylated (i.e., kinase-active), but were unable to fully activate α-chimerin in the absence of ephrinB3 stimulation (FIG. 5E). These results suggest that EphA4 kinase activity alone is not sufficient for inducing the Rac-GAP activity of α-chimerin.

FIG. 5 shows that α-chimerin binds with EphA4 and regulates Rac1 activity in response to ephrinB3→EphA4 forward signaling. In the experiment that produced results shown in FIG. 5E, COS-7 cells were transfected with the indicated plasmid and stimulated with pre-clustered ephrinB3-Fc (+) or Fc (−) for 10 minutes. GST-fused Rac1 was detected by SDS-PAGE and immunoblot, and its levels were measured and normalized to the corresponding total Rac1 levels. Rac1 activity (fold increase/basal) is presented as means and standard deviations. FIG. 5F shows results of statistical processing of the data shown in FIG. 5E. EphrinB3 stimulation inactivated Rac in cells expressing both wild-type EphA4 and α-chimerin, but not in cells expressing nonfunctional EphA4 and normal α-chimerin or normal EphA4 and nonfunctional α-chimerin. n=4 (EphA4$^{WT}$+α2-chimerin$^{WT}$), 5 (EphA4$^{FF}$+α2-chimerin$^{WT}$), or 3 (EphA4$^{WT}$+α2-chimerin$^{mfy}$). All data are presented as the mean±standard deviation. (*p<0.05, ANOVA/Tukey HSD).

Figure 6A:
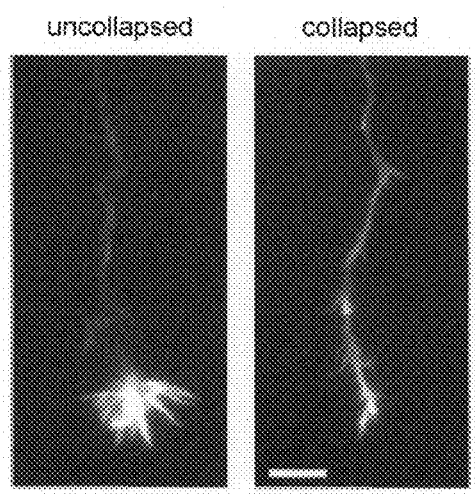
FIG. 6A is a diagram showing growth cones in phalloidin-stained cultured cortical neurons treated with pre-clustered Fc control (uncollapsed) or ephrinB3-Fc (collapsed).
Figure 6B:
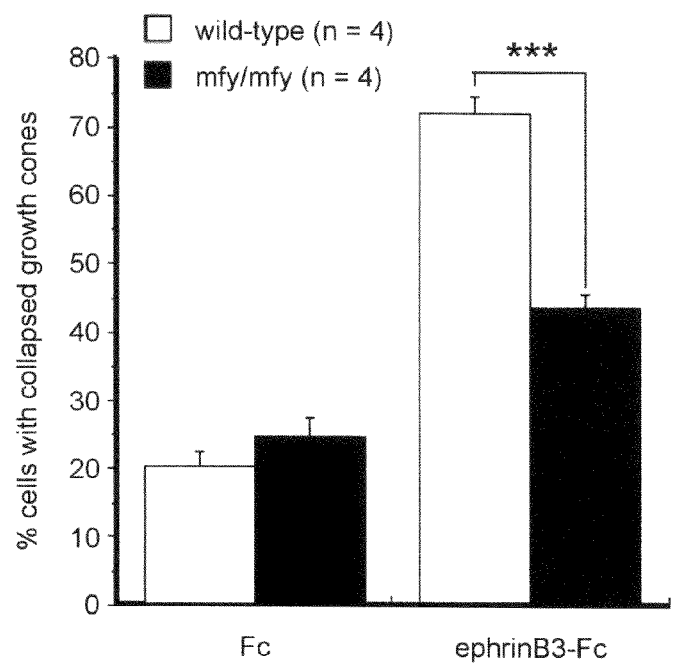
FIG. 6B is a diagram showing changes in growth cones brought by ephrinB3 stimulation in wild-type and mfy mice.
Figure 6C:
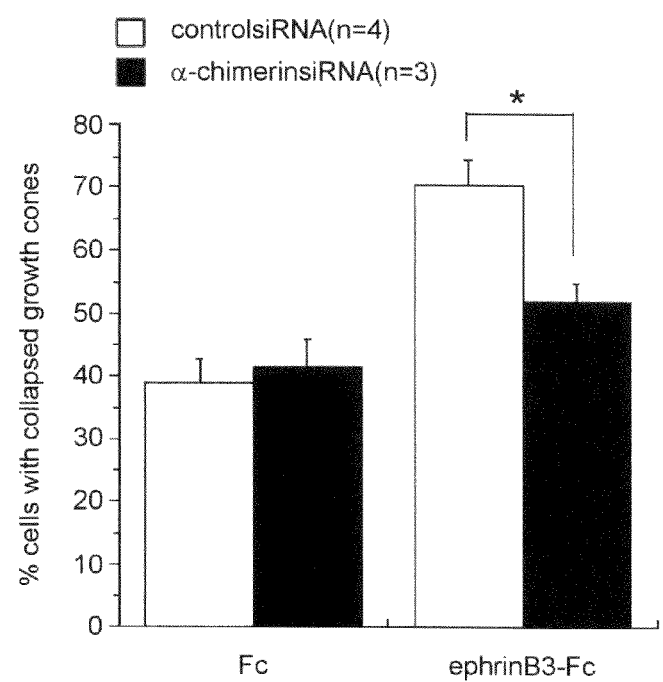
FIG. 6C is a diagram showing that down-regulation of α-chimerin by siRNA suppresses ephrinB3-induced growth-cone collapse.
Figure 6D:
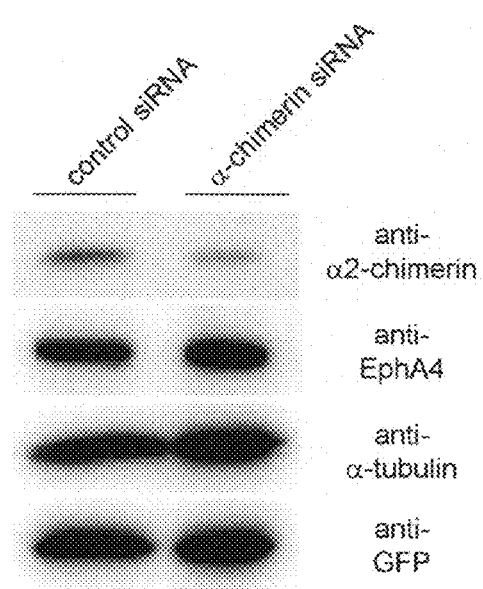
FIG. 6D is a diagram showing changes in the level of α-chimerin proteins brought by α-chimerin-specific siRNA.

10. Down-Regulation of α-Chimerin Suppresses Ephrin-Induced Growth-Cone Collapse in Cultured Cortical Neurons EphrinB3/EphA4 forward signaling is known to induce growth-cone collapse in cultured neurons derived from the motor cortex (Egea et al., 2005, Neuron 47, 515-528; and Kullander et al., 2001, Neuron 29, 73-84). To determine whether α-chimerin regulates growth-cone collapse in the ephrinB3/EphA4 forward signaling pathway, two experiments were conducted. First, neurons derived from the motor cortex of wild-type and mfy mice on embryonic day 16.5 (E16.5) were cultured and stimulated with pre-clustered Fc or ephrinB3. EphrinB3 induced growth-cone collapse in wild-type cortical neurons, as previously reported (Kullander et al., 2001, Genes Dev. 15, 877-888, FIGS. 6A and 6B). However, in the mfy cortical neurons, the frequency of collapse was significantly reduced (FIG. 6B). Second, cultured neurons prepared from the E18.5 rat motor cortex were transfected with an α-chimerin-specific siRNA-expression vector (FIG. 14). The frequency of ephrinB3-induced growth-cone collapse was significantly reduced in the transfected cells (FIG. 6C). Indeed, western blot using an anti-α-chimerin antibody demonstrated that α-chimerin protein levels were drastically (90% or more) reduced in the transfected cells (FIG. 6D).

From these results, it was concluded that α-chimerin Rac-GAP acts downstream of ephrinB3/Eph signaling to cause growth-cone collapse of cortical neurons.

Taken together, the results of the in vitro and in vivo experiments confirm that α-chimerin is a key molecule that links ephrinB3-induced EphA4 activation to the inactivation of Rac, a positive regulator of process outgrowth, thereby causing growth-cone collapse and, eventually axonal repulsion at the spinal cord midline.

FIG. 6 shows that down-regulation of α-chimerin suppresses ephrinB3-induced growth-cone collapse. FIG. 6A shows representative examples of growth cones in phalloidin-stained cultured cortical neurons treated with pre-clustered Fc control (uncollapsed) or ephrinB3-Fc (collapsed). The scale bar in FIG. 6A represents 10 p.m. FIG. 6B shows that growth-cone collapse was induced by ephrinB3 stimulation in cultured neurons derived from the wild-type cortex, but was barely seen in those derived from the mfy cortex. All data are presented as the mean±standard deviation of four independent experiments in each of which 100 cells were counted (***$p<0.001$, Student's t-test). FIG. 6C shows that down-regulation of α-chimerin by siRNA suppressed ephrinB3-induced growth-cone collapse. Cultured neurons derived from the E18.5 rat cortex were transfected with an siRNA- and EYFP-expression vector. In each experiment, 34 to 67 neurons expressing EYFP were counted. (*$p<0.05$, Student's t-test).

In conclusion, it can be said from the present Examples that:

α-chimerin is a key mediator of ephrinB3/EphA4 forward signaling and causes repulsion of CST axons at the spinal cord midline.

Figure 4F:
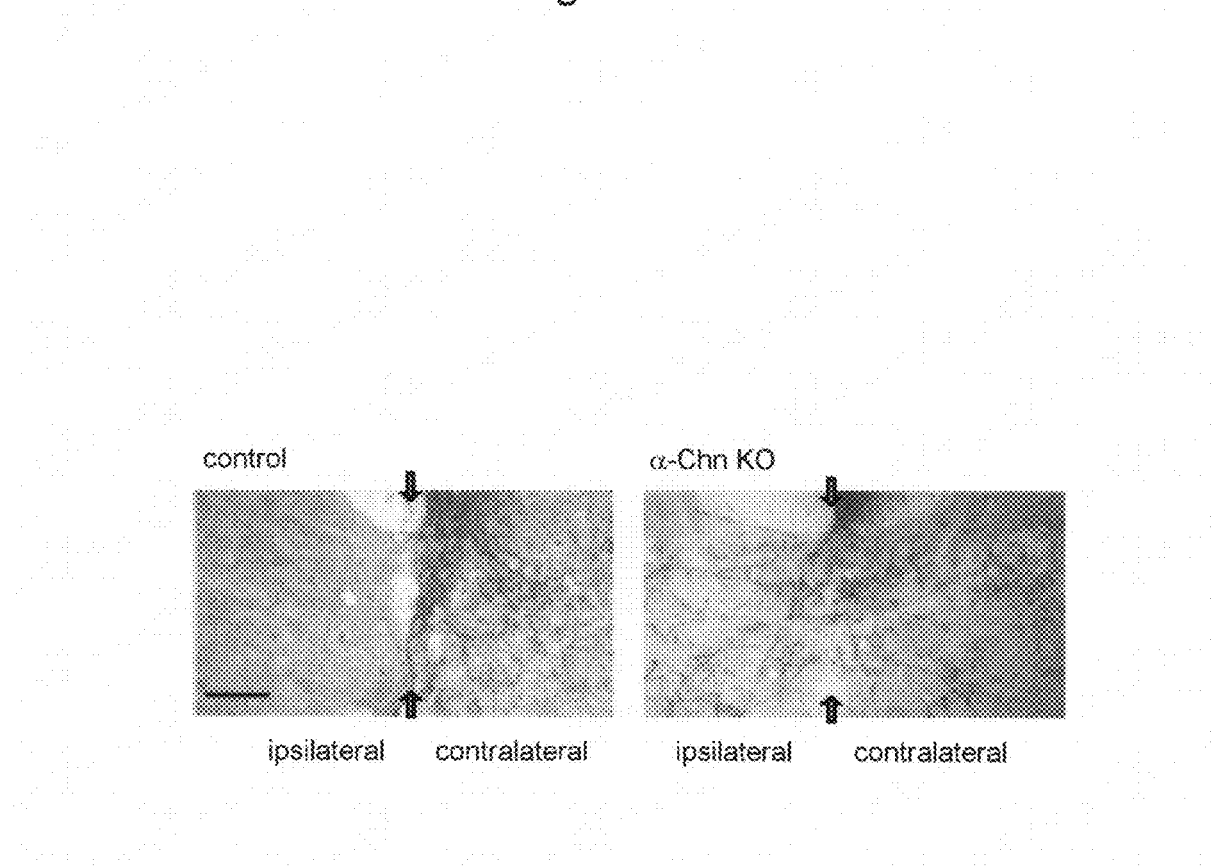
FIG. 4F is a diagram showing sections at cervical levels of the spinal cord in anterograde tracings of CST axons.
Figure 7A:
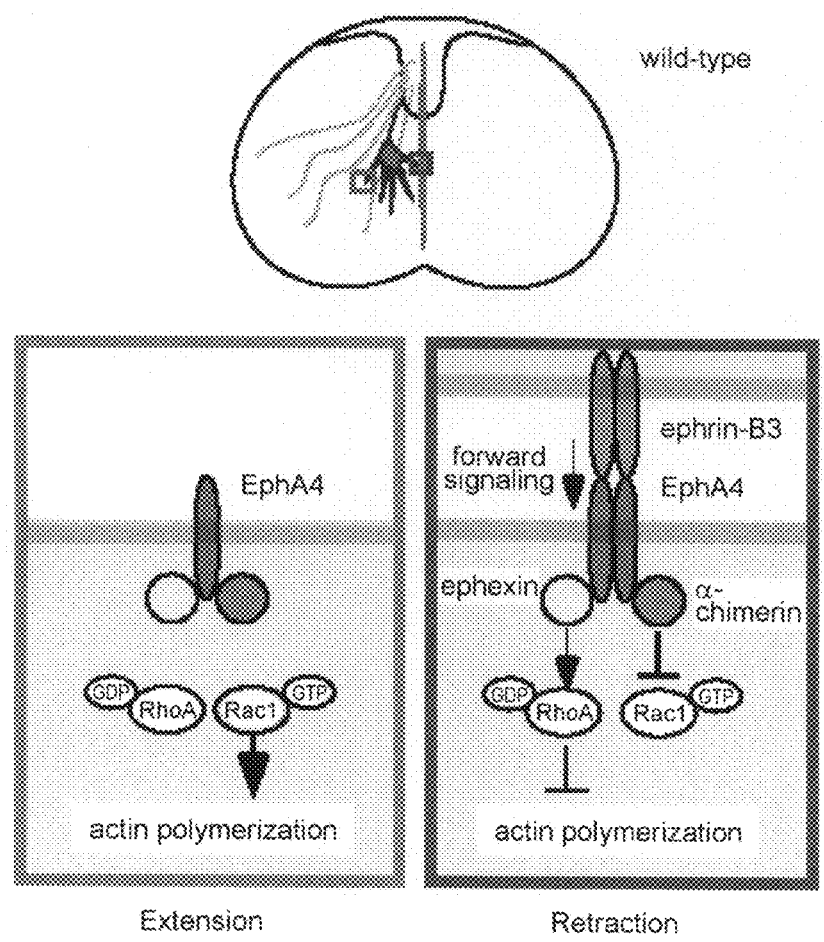
FIG. 7A is a diagram showing a model of ephrinB3/EphA4 forward signaling in CST axon guidance at the midline in wild-type mice.
Figure 7B:
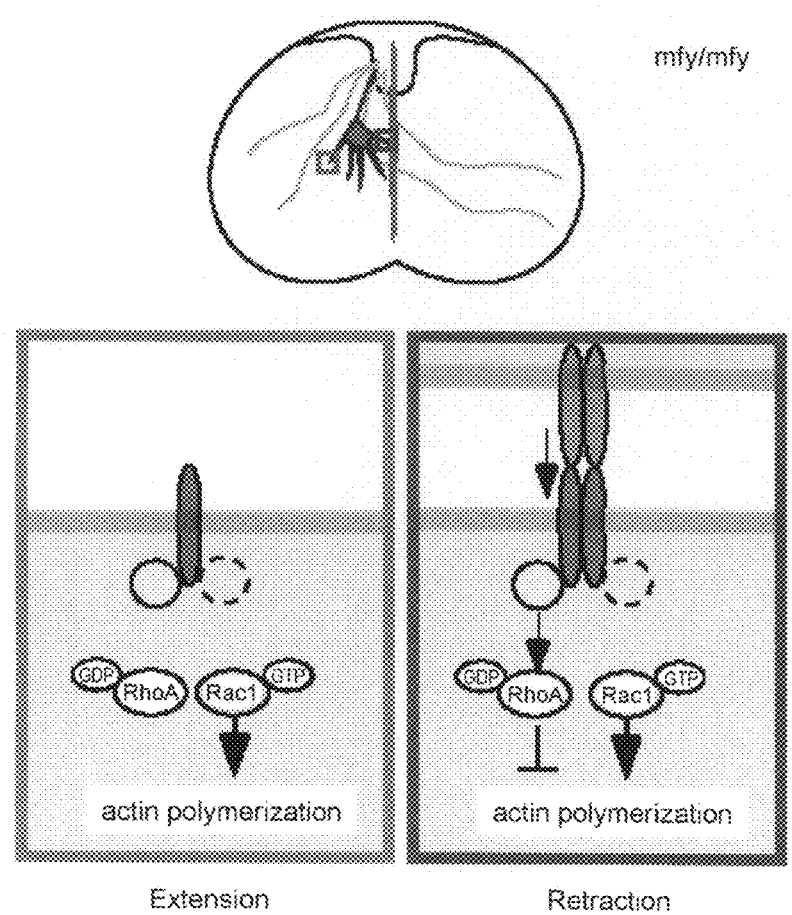
FIG. 7B is a diagram showing a model of ephrinB3/EphA4 forward signaling in CST axon guidance at the midline in mfy mice.

The present Examples demonstrated that: (1) α-chimerin is co-localized with EphA4 in the developing CST (FIG. 13); (2) α-chimerin binds with EphA4 both in vitro and in vivo (FIGS. 5A to 5D); (3) when EphA4 is stimulated by ephrinB3, α-chimerin inactivates Rac, a positive regulator of process outgrowth (FIG. 5F); (4) the effect of inducing growth-cone collapse by ephrinB3 stimulation is reduced in cultured cortical neurons in which α-chimerin protein expression is suppressed by RNAi or mfy mutation (FIG. 6); and (5) repulsions of CST and CPG axons at the spinal cord midline are known to be dependent on ephrinB3/EphA4 forward signaling (Kullander et al., 2003, Science 299, 1889-1892; Kullander et al., 2001, Genes Dev. 15, 877-888; Kullander et al., 2001, Neuron 29, 73-84; and Yokoyama et al., 2001, Neuron 29, 85-97), and both of these processes are impaired in mfy and α-chimerin-KO mice (FIGS. 1B, 2D, and 4F). These results indicate that Rac-GAP α-chimerin mediates ephrinB3/EphA4 forward signaling and regulates CST and CPG axon guidance (FIG. 7). FIG. 7 shows a model of ephrinB3/EphA4 forward signaling in CST axon guidance at the midline. In wild-type mice, as shown in FIG. 7A, growth cones extend due to the basal activity of Rac, a positive regulator of process outgrowth, in the absence of ephrinB3 stimulation (left green box). By contrast, at the spinal cord midline that anchors ephrinB3, CST axons receive forward signals induced via EphA4. This forward signaling inactivates Rac via α-chimerin, leading to growth-cone retraction (right red box). It has been reported that ephrin/EphA signaling is also likely to activate RhoA, a negative regulator of process outgrowth, via ephexin. The cooperative action of the RhoA-activator ephexin and the Rac-inactivator α-chimerin might induce efficient retraction of axons. In mfy mice, as shown in FIG. 7B, growth cones fail to stop at the midline due to the absence of α-chimerin-induced Rac inactivation, even in the presence of ephexin.

Attention has been given recently to the findings that EphA regulates growth-cone dynamics via Rho-GEF ephexin1 (Shamah et al., 2001, Cell 105, 233-244). Activation of RhoA induces growth-cone collapse, while activation of Rac and Cdc42 promotes its extension (Etienne-Manneville and Hall, 2002, Nature 420, 629-635; and Luo, 2000, Nat. Rev. Neurosci. 1, 173-180). It has been reported that stimulation of Eph by ephrin induces the GEF activity of ephexin towards RhoA, thereby causing growth-cone collapse in in vitro experiments (FIG. 7A, Shamah et al., 2001, Cell 105, 233-244). On the other hand, it was shown in the present Examples that the binding of ephrin and Eph induces growth-cone collapse via Rac inactivation induced by the GAP activity of α-chimerin. As both ephexin1 and α-chimerin are widely expressed in the central nervous system (Hall et al., 2001, J. Neurosci. 21, 5191-5202; Hall et al., 1993, Mol. Cell Biol. 13, 4986-4998; and Shamah et al., 2001, Cell 105, 233-244), it is likely that the cooperative action of ephexin-induced RhoA activation and α-chimerin-induced Rac inactivation functions to induce efficient growth-cone collapse during axon guidance in various circuit formations. Ephexin1-KO mice have no particular abnormality (Sahin et al., 2005, Neuron 46, 191-204). This might be due to compensation by other ephexin-family members. Alternatively, the presence of α-chimerin might prevent growth-cone extension via Rac inactivation in response to ephrin/Eph signaling, even in the absence of ephexin-induced RhoA activation. Impaired CST and CPG axon guidance was found in α-chimerin mutant mice, compared with normal one in ephexin-knockout mice.

Critical Role of Rho-GTPase Inactivation in Ephrin/Eph Signaling

Ephrin-Eph signaling plays an important role in a wide range of biological processes, including oocyte maturation, early morphogenesis, segmentation, cell migration, synaptic plasticity, dendritic-spine formation, and axon guidance (Flanagan and Vanderhaeghen, 1998, Neurosci. 21, 309-345; Palmer and Klein, 2003, Genes Dev. 17, 1429-1450; and Pasquale, 2005, Nat. Rev. Mol. Cell Biol. 6, 462-475). Recent in vitro studies suggest that in various biological processes, ephrin/Eph signaling regulates actin dynamics by activating low-molecular-weight G proteins of the Rho family (Rho-GTPase), such as RhoA, Rac, and Cdc42 (Cowan et al., 2005, Neuron 46, 205-217; Fu et al., 2007, Nat. Neurosci. 10, 67-76; hie and Yamaguchi, 2002, Nat. Neurosci. 5, 1117-1118; Murai and Pasquale, 2005, Neuron 46, 161-163; Ogita et al., 2003, Circ. Res. 93, 23-31; Penzes et al., 2003, Neuron 37, 263-274; Shamah et al., 2001, Cell 105, 233-244; and Tanaka et al., 2004, EMBO J. 23, 1075-1088). The results of the present Examples suggest that a further mode of ephrin/Eph signaling exists, in which Ephs regulate actin dynamics by inactivating the Rho family through Rho-GAPs.

It has been suggested that Ephrin/Eph controls actin dynamics by regulating the balance between negative regulators of actin polymerization (such as RhoA) and positive regulators (such as Rac) (Sahin et al., 2005, Neuron 46, 191-204; and Shamah et al., 2001, Cell 105, 233-244). This theory only takes into account activation mechanisms of the Rho family. However, in the present Examples, it was shown that Rho inactivation is also important for the ephrin/Eph regulation of actin dynamics. The activity of each member in the Rho family may be regulated by the balance between its activation by Rho-GEFs and its inactivation by Rho-GAPs. Mammals have many diverse Rho-GEFs and Rho-GAPs with different substrate specificities that are regulated by different mechanisms (Etienne-Manneville and Hall, 2002, Nature 420, 629-635). Thus, it is possible that ephrin/Eph signaling in different biological processes employs combination of specific Rho-GEFs and Rho-GAPS, thereby appropriately controlling the activity of each member in the Rho family. In short, it is suggested that ephrin/Eph regulates actin dynamics in two ways: first, by regulating the balance between different Rho-GTPases (such as RhoA and Racy; and second, by regulating the balance between activation and inactivation of each individual Rho-GTPase.

Regulation and Roles of α-Chimerin in Neural Development and Function

The present Examples indicated the involvement of α-chimerin in ephrinB3/EphA4 forward signaling and also answered a question as to how ephrinB3/EphA4 activates α-chimerin. As EphA4 proteins lacking kinase activity fail to activate α-chimerin (FIG. 5F), it is apparent that the kinase activity of EphA4 is essential for the activation of α-chimerin. However, EphA4 proteins over-expressed in COS cells were phosphorylated (i.e., kinase-active), but were unable to fully activate α-chimerin in the absence of ephrinB3 stimulation (FIGS. 5E and 5F), showing that EphA4 kinase activity alone is not sufficient. Indeed, recent reports indicate that mice having constitutively active EphA4 have normal gate patterns, normal CST and CPG axon guidance at the midline, and normal morphology of the spinal cord (Egea et al., 2005, Neuron 47, 515-528). Cultured neurons derived from the cortex of the mice can induce normal growth-cone collapse in response to ephrinB3 stimulation. From these results, it has been proposed that EphA4 kinase activity alone is not sufficient for ephrinB/EphA4 signaling in vivo, and that clustering of EphA4 is an essential component of the signaling (Egea et al., 2005, Neuron 47, 515-528). The patterns of regulation of α-chimerin in cultured cells shown in the present Examples are consistent with the patterns of ephrinB3/EphA4 signaling in vivo.

Both α1-chimerin and α2-chimerin isoforms have a single copy of the C1 domain, which can be activated by the binding of phorbol ester or DAG thereto (Hall et al., 1990, J. Mol. Biol. 211, 11-16; and Hall et al., 1993, Mol. Cell Biol. 13, 4986-4998). Recently, it has been reported that Cdk5 regulates EphA4-mediated dendritic-spine retraction (Fu et al., 2007, Nat. Neurosci. 10, 67-76). It has also been reported Cdk5 binds with α2-chimerin (Qi et al., 2004, FEBS Lett. 561, 177-180). Thus, it is possible that a protein complex formed by clustering of EphA4 recruits some additional proteins required for linking EphA4 activation to α-chimerin activation. Such additional proteins could include Cdk5/p35 and DAG-producing enzymes (such as phospholipase Cγ). It should be noted that these (or functionally equivalent) molecules do not appear to be specific for neurons, but rather are ubiquitous, as only the expression of EphA4 and α2-chimerin in COS cells is sufficient for ephrinB3-induced Rac inactivation (FIGS. 5E and 5F).

The α-chimerin gene is widely expressed in the central nervous system both during development and in adulthood (Hall et al., 2001, J. Neurosci. 21, 5191-5202; Hall et al., 1990, J. Mol. Biol. 211, 11-16; and Hall et al., 1993, Mol. Cell Biol. 13, 4986-4998). The α-chimerin protein is expressed not only in axons but also in dendrites (Hall et al., 2001, J. Neurosci. 21, 5191-5202). It would be interesting to analyze whether α-chimerin plays a role in dendrite development in the brain. Recent experiments using over-expression or siRNA-induced knockdown in cultured hippocampal neurons or cerebellar slices suggest that α-chimerin regulates dendritic morphology and dendritic-spine density (Buttery et al., 2006, Proc. Natl. Acad. Sci. USA 103, 1924-1929; and Van de Ven et al., 2005, J. Neurosci. 25, 9488-9496). As α-chimerin binds with NMDA glutamic acid receptors in vitro (Van de Ven et al., 2005, J. Neurosci. 25, 9488-9496), it might also be involved in NMDA receptor-mediated developmental plasticity, such as maturation of the barrel cortex as well as in learning and memory (Iwasato et al., 2000, Nature 406, 726-731; and Iwasato et al., 1997, Neuron 19, 1201-1210). The mfy mouse is thus a promising experimental material for elucidating the roles of α-chimerin Rac-GAP in the development and function of the central nervous system.

[Free Text for Sequence List]

SEQ ID NOs: 1 to 93: synthetic

---

What is claimed is:

1. A method for screening an agent for activity as a regulator of axon extension, comprising
   (a) administering candidate agents to a cell or an animal;
   (b) detecting promotion or inhibition of interaction between EphA4 and α-chimerin, compared with the case where the agent is not administered;
   (c) selecting as a regulator of axon extension from among the agents one that promotes or inhibits interaction between EphA4 and α-chimerin.

2. The method of claim 1, wherein interaction between EphA4 and α-chimerin is assayed by precipitation of an EphA4:α-chimerin complex.

3. The method of claim 2, wherein the precipitation is measured using an anti-α-chimerin antibody.

4. The method of claim 2, wherein the precipitation is measured using a protein tag fused to EphA4.

5. The method of claim 1, wherein interaction between EphA4 and α-chimerin is assayed by detecting co-localization of EphA4 and α-chimerin in a cell.

6. The method of claim 5, wherein the co-localization is detected by an immunohistochemical assay.

7. The method of claim 1 that further comprises detecting an increase in ephrinB3-mediated phosphorylation of EphA4.

* * * * *

SEQUENCE LISTING

```
<160> NUMBER OF SEQ ID NOS: 99

<210> SEQ ID NO 1
<211> LENGTH: 18
<212> TYPE: PRT
<213> ORGANISM: Artificial
<220> FEATURE:
<223> OTHER INFORMATION: synthetic

<400> SEQUENCE: 1

Met Ala Leu Thr Leu Phe Asp Thr Asp Glu Tyr Arg Pro Pro Val Trp
1               5                   10                  15

Lys Cys

<210> SEQ ID NO 2
<211> LENGTH: 20
<212> TYPE: DNA
<213> ORGANISM: Artificial
<220> FEATURE:
<223> OTHER INFORMATION: synthetic

<400> SEQUENCE: 2
ggctcagtgt ggtgctttgg                                              20
```

```
<210> SEQ ID NO 3
<211> LENGTH: 20
<212> TYPE: DNA
<213> ORGANISM: Artificial
<220> FEATURE:
<223> OTHER INFORMATION: synthetic

<400> SEQUENCE: 3
tagttggtac cacgcagcag                                               20

<210> SEQ ID NO 4
<211> LENGTH: 20
<212> TYPE: DNA
<213> ORGANISM: Artificial
<220> FEATURE:
<223> OTHER INFORMATION: synthetic

<400> SEQUENCE: 4
agctttgagc ctggtgatct                                               20

<210> SEQ ID NO 5
<211> LENGTH: 20
<212> TYPE: DNA
<213> ORGANISM: Artificial
<220> FEATURE:
<223> OTHER INFORMATION: synthetic

<400> SEQUENCE: 5
agaacgatgt gctacacatg                                               20

<210> SEQ ID NO 6
<211> LENGTH: 20
<212> TYPE: DNA
<213> ORGANISM: Artificial
<220> FEATURE:
<223> OTHER INFORMATION: synthetic

<400> SEQUENCE: 6
ctggcatttc actgaacaca                                               20

<210> SEQ ID NO 7
<211> LENGTH: 20
<212> TYPE: DNA
<213> ORGANISM: Artificial
<220> FEATURE:
<223> OTHER INFORMATION: synthetic

<400> SEQUENCE: 7
ttagggccgt tctgtttgac                                               20

<210> SEQ ID NO 8
<211> LENGTH: 20
<212> TYPE: DNA
<213> ORGANISM: Artificial
<220> FEATURE:
<223> OTHER INFORMATION: synthetic

<400> SEQUENCE: 8
cctcaacact gactgaacta                                               20

<210> SEQ ID NO 9
<211> LENGTH: 20
<212> TYPE: DNA
<213> ORGANISM: Artificial
<220> FEATURE:
<223> OTHER INFORMATION: synthetic

<400> SEQUENCE: 9
```

```
tcttaatgca ctgcagtgtc                                              20

<210> SEQ ID NO 10
<211> LENGTH: 20
<212> TYPE: DNA
<213> ORGANISM: Artificial
<220> FEATURE:
<223> OTHER INFORMATION: synthetic

<400> SEQUENCE: 10
tatgagatgt cgtctctcgg                                              20

<210> SEQ ID NO 11
<211> LENGTH: 20
<212> TYPE: DNA
<213> ORGANISM: Artificial
<220> FEATURE:
<223> OTHER INFORMATION: synthetic

<400> SEQUENCE: 11
tgtgttccga cgaactatcc                                              20

<210> SEQ ID NO 12
<211> LENGTH: 20
<212> TYPE: DNA
<213> ORGANISM: Artificial
<220> FEATURE:
<223> OTHER INFORMATION: synthetic

<400> SEQUENCE: 12
ggtgatttgg cttctgcaca                                              20

<210> SEQ ID NO 13
<211> LENGTH: 19
<212> TYPE: DNA
<213> ORGANISM: Artificial
<220> FEATURE:
<223> OTHER INFORMATION: synthetic

<400> SEQUENCE: 13
tgagctgtcc taaacacac                                               19

<210> SEQ ID NO 14
<211> LENGTH: 20
<212> TYPE: DNA
<213> ORGANISM: Artificial
<220> FEATURE:
<223> OTHER INFORMATION: synthetic

<400> SEQUENCE: 14
aaggtatgcc tgctgctcat                                              20

<210> SEQ ID NO 15
<211> LENGTH: 20
<212> TYPE: DNA
<213> ORGANISM: Artificial
<220> FEATURE:
<223> OTHER INFORMATION: synthetic

<400> SEQUENCE: 15
cacgatgccc ccgaaaaagg                                              20

<210> SEQ ID NO 16
<211> LENGTH: 20
<212> TYPE: DNA
<213> ORGANISM: Artificial
```

```
<220> FEATURE:
<223> OTHER INFORMATION: synthetic

<400> SEQUENCE: 16
cagcccaaaa cctgctatgg                                                   20

<210> SEQ ID NO 17
<211> LENGTH: 20
<212> TYPE: DNA
<213> ORGANISM: Artificial
<220> FEATURE:
<223> OTHER INFORMATION: synthetic

<400> SEQUENCE: 17
tgctatggcc acgtctatac                                                   20

<210> SEQ ID NO 18
<211> LENGTH: 20
<212> TYPE: DNA
<213> ORGANISM: Artificial
<220> FEATURE:
<223> OTHER INFORMATION: synthetic

<400> SEQUENCE: 18
gacgccaaga tggggaagtc                                                   20

<210> SEQ ID NO 19
<211> LENGTH: 20
<212> TYPE: DNA
<213> ORGANISM: Artificial
<220> FEATURE:
<223> OTHER INFORMATION: synthetic

<400> SEQUENCE: 19
gagaaatgga accctattcc                                                   20

<210> SEQ ID NO 20
<211> LENGTH: 20
<212> TYPE: DNA
<213> ORGANISM: Artificial
<220> FEATURE:
<223> OTHER INFORMATION: synthetic

<400> SEQUENCE: 20
aagaactcaa cgcttgctgg                                                   20

<210> SEQ ID NO 21
<211> LENGTH: 20
<212> TYPE: DNA
<213> ORGANISM: Artificial
<220> FEATURE:
<223> OTHER INFORMATION: synthetic

<400> SEQUENCE: 21
tctgattgtt gaccagcaac                                                   20

<210> SEQ ID NO 22
<211> LENGTH: 20
<212> TYPE: DNA
<213> ORGANISM: Artificial
<220> FEATURE:
<223> OTHER INFORMATION: synthetic

<400> SEQUENCE: 22
aggccagttt ggaagtggag                                                   20
```

```
<210> SEQ ID NO 23
<211> LENGTH: 20
<212> TYPE: DNA
<213> ORGANISM: Artificial
<220> FEATURE:
<223> OTHER INFORMATION: synthetic

<400> SEQUENCE: 23
ttctgggctc cgaacatgag                                          20

<210> SEQ ID NO 24
<211> LENGTH: 20
<212> TYPE: DNA
<213> ORGANISM: Artificial
<220> FEATURE:
<223> OTHER INFORMATION: synthetic

<400> SEQUENCE: 24
tggagctctc gactgttctc                                          20

<210> SEQ ID NO 25
<211> LENGTH: 20
<212> TYPE: DNA
<213> ORGANISM: Artificial
<220> FEATURE:
<223> OTHER INFORMATION: synthetic

<400> SEQUENCE: 25
gagagatgct gcatgctttg                                          20

<210> SEQ ID NO 26
<211> LENGTH: 20
<212> TYPE: DNA
<213> ORGANISM: Artificial
<220> FEATURE:
<223> OTHER INFORMATION: synthetic

<400> SEQUENCE: 26
ccatggctct gaccctgttc                                          20

<210> SEQ ID NO 27
<211> LENGTH: 20
<212> TYPE: DNA
<213> ORGANISM: Artificial
<220> FEATURE:
<223> OTHER INFORMATION: synthetic

<400> SEQUENCE: 27
agggctttcc ttgctgtgtc                                          20

<210> SEQ ID NO 28
<211> LENGTH: 20
<212> TYPE: DNA
<213> ORGANISM: Artificial
<220> FEATURE:
<223> OTHER INFORMATION: synthetic

<400> SEQUENCE: 28
cgccaggaag aaagatgttc                                          20

<210> SEQ ID NO 29
<211> LENGTH: 20
<212> TYPE: DNA
<213> ORGANISM: Artificial
<220> FEATURE:
<223> OTHER INFORMATION: synthetic

<400> SEQUENCE: 29
```

```
ccgcttttct cagctgtgac                                           20

<210> SEQ ID NO 30
<211> LENGTH: 20
<212> TYPE: DNA
<213> ORGANISM: Artificial
<220> FEATURE:
<223> OTHER INFORMATION: synthetic

<400> SEQUENCE: 30
atgagctcgt acttcgtgaa                                           20

<210> SEQ ID NO 31
<211> LENGTH: 20
<212> TYPE: DNA
<213> ORGANISM: Artificial
<220> FEATURE:
<223> OTHER INFORMATION: synthetic

<400> SEQUENCE: 31
tgaacccgct gtactccaac                                           20

<210> SEQ ID NO 32
<211> LENGTH: 20
<212> TYPE: DNA
<213> ORGANISM: Artificial
<220> FEATURE:
<223> OTHER INFORMATION: synthetic

<400> SEQUENCE: 32
aagaaggtgt gcccaaggct                                           20

<210> SEQ ID NO 33
<211> LENGTH: 20
<212> TYPE: DNA
<213> ORGANISM: Artificial
<220> FEATURE:
<223> OTHER INFORMATION: synthetic

<400> SEQUENCE: 33
gaagccacta tttacctcgg                                           20

<210> SEQ ID NO 34
<211> LENGTH: 20
<212> TYPE: DNA
<213> ORGANISM: Artificial
<220> FEATURE:
<223> OTHER INFORMATION: synthetic

<400> SEQUENCE: 34
agcgagccat gagctcttac                                           20

<210> SEQ ID NO 35
<211> LENGTH: 20
<212> TYPE: DNA
<213> ORGANISM: Artificial
<220> FEATURE:
<223> OTHER INFORMATION: synthetic

<400> SEQUENCE: 35
ctctgctcgt cttagcgttg                                           20

<210> SEQ ID NO 36
<211> LENGTH: 20
<212> TYPE: DNA
<213> ORGANISM: Artificial
```

```
<220> FEATURE:
<223> OTHER INFORMATION: synthetic

<400> SEQUENCE: 36
ccaggagcca tttatctcag                                               20

<210> SEQ ID NO 37
<211> LENGTH: 20
<212> TYPE: DNA
<213> ORGANISM: Artificial
<220> FEATURE:
<223> OTHER INFORMATION: synthetic

<400> SEQUENCE: 37
gcaagacaga tgggactttc                                               20

<210> SEQ ID NO 38
<211> LENGTH: 20
<212> TYPE: DNA
<213> ORGANISM: Artificial
<220> FEATURE:
<223> OTHER INFORMATION: synthetic

<400> SEQUENCE: 38
gcatctgacc caatccctca                                               20

<210> SEQ ID NO 39
<211> LENGTH: 20
<212> TYPE: DNA
<213> ORGANISM: Artificial
<220> FEATURE:
<223> OTHER INFORMATION: synthetic

<400> SEQUENCE: 39
atcttcaggc tctacgcttg                                               20

<210> SEQ ID NO 40
<211> LENGTH: 20
<212> TYPE: DNA
<213> ORGANISM: Artificial
<220> FEATURE:
<223> OTHER INFORMATION: synthetic

<400> SEQUENCE: 40
actgtgacaa gctgtaaagg                                               20

<210> SEQ ID NO 41
<211> LENGTH: 19
<212> TYPE: DNA
<213> ORGANISM: Artificial
<220> FEATURE:
<223> OTHER INFORMATION: synthetic

<400> SEQUENCE: 41
ggttagacta ccattcgca                                                19

<210> SEQ ID NO 42
<211> LENGTH: 20
<212> TYPE: DNA
<213> ORGANISM: Artificial
<220> FEATURE:
<223> OTHER INFORMATION: synthetic

<400> SEQUENCE: 42
gtgctcatgt gagtatcttc                                               20
```

```
<210> SEQ ID NO 43
<211> LENGTH: 20
<212> TYPE: DNA
<213> ORGANISM: Artificial
<220> FEATURE:
<223> OTHER INFORMATION: synthetic

<400> SEQUENCE: 43
aaaacaccca tcccccaag                                                     20

<210> SEQ ID NO 44
<211> LENGTH: 20
<212> TYPE: DNA
<213> ORGANISM: Artificial
<220> FEATURE:
<223> OTHER INFORMATION: synthetic

<400> SEQUENCE: 44
ctctaggagt cgttgggacc                                                    20

<210> SEQ ID NO 45
<211> LENGTH: 20
<212> TYPE: DNA
<213> ORGANISM: Artificial
<220> FEATURE:
<223> OTHER INFORMATION: synthetic

<400> SEQUENCE: 45
ttatgtcgga ggatggctcg                                                    20

<210> SEQ ID NO 46
<211> LENGTH: 20
<212> TYPE: DNA
<213> ORGANISM: Artificial
<220> FEATURE:
<223> OTHER INFORMATION: synthetic

<400> SEQUENCE: 46
tgctccgaag ctctgttgag                                                    20

<210> SEQ ID NO 47
<211> LENGTH: 20
<212> TYPE: DNA
<213> ORGANISM: Artificial
<220> FEATURE:
<223> OTHER INFORMATION: synthetic

<400> SEQUENCE: 47
ttaccagggc agtgaggaag                                                    20

<210> SEQ ID NO 48
<211> LENGTH: 20
<212> TYPE: DNA
<213> ORGANISM: Artificial
<220> FEATURE:
<223> OTHER INFORMATION: synthetic

<400> SEQUENCE: 48
ctagcacttg agttcgttac                                                    20

<210> SEQ ID NO 49
<211> LENGTH: 20
<212> TYPE: DNA
<213> ORGANISM: Artificial
<220> FEATURE:
<223> OTHER INFORMATION: synthetic

<400> SEQUENCE: 49
```

```
tctggcactt aagtcttagg                                               20

<210> SEQ ID NO 50
<211> LENGTH: 20
<212> TYPE: DNA
<213> ORGANISM: Artificial
<220> FEATURE:
<223> OTHER INFORMATION: synthetic

<400> SEQUENCE: 50
agatgacctg cccaaggtca                                               20

<210> SEQ ID NO 51
<211> LENGTH: 20
<212> TYPE: DNA
<213> ORGANISM: Artificial
<220> FEATURE:
<223> OTHER INFORMATION: synthetic

<400> SEQUENCE: 51
tgtgagacat acacgtaggc                                               20

<210> SEQ ID NO 52
<211> LENGTH: 20
<212> TYPE: DNA
<213> ORGANISM: Artificial
<220> FEATURE:
<223> OTHER INFORMATION: synthetic

<400> SEQUENCE: 52
tcagcctctg ctcatccttg                                               20

<210> SEQ ID NO 53
<211> LENGTH: 20
<212> TYPE: DNA
<213> ORGANISM: Artificial
<220> FEATURE:
<223> OTHER INFORMATION: synthetic

<400> SEQUENCE: 53
aggacatgta gaacactgca                                               20

<210> SEQ ID NO 54
<211> LENGTH: 20
<212> TYPE: DNA
<213> ORGANISM: Artificial
<220> FEATURE:
<223> OTHER INFORMATION: synthetic

<400> SEQUENCE: 54
tctgggtatt tggccaaacc                                               20

<210> SEQ ID NO 55
<211> LENGTH: 20
<212> TYPE: DNA
<213> ORGANISM: Artificial
<220> FEATURE:
<223> OTHER INFORMATION: synthetic

<400> SEQUENCE: 55
tacagtcttc ggagtcacag                                               20

<210> SEQ ID NO 56
<211> LENGTH: 20
<212> TYPE: DNA
<213> ORGANISM: Artificial
```

```
<220> FEATURE:
<223> OTHER INFORMATION: synthetic

<400> SEQUENCE: 56
atccagttga aggcacatgg                                              20

<210> SEQ ID NO 57
<211> LENGTH: 20
<212> TYPE: DNA
<213> ORGANISM: Artificial
<220> FEATURE:
<223> OTHER INFORMATION: synthetic

<400> SEQUENCE: 57
tggtgtccac cagtatatac                                              20

<210> SEQ ID NO 58
<211> LENGTH: 20
<212> TYPE: DNA
<213> ORGANISM: Artificial
<220> FEATURE:
<223> OTHER INFORMATION: synthetic

<400> SEQUENCE: 58
caagagcagt gacattaagg                                              20

<210> SEQ ID NO 59
<211> LENGTH: 20
<212> TYPE: DNA
<213> ORGANISM: Artificial
<220> FEATURE:
<223> OTHER INFORMATION: synthetic

<400> SEQUENCE: 59
ccgggtcttc gagaagcaaa                                              20

<210> SEQ ID NO 60
<211> LENGTH: 20
<212> TYPE: DNA
<213> ORGANISM: Artificial
<220> FEATURE:
<223> OTHER INFORMATION: synthetic

<400> SEQUENCE: 60
aaggctcttg agcctgagaa                                              20

<210> SEQ ID NO 61
<211> LENGTH: 20
<212> TYPE: DNA
<213> ORGANISM: Artificial
<220> FEATURE:
<223> OTHER INFORMATION: synthetic

<400> SEQUENCE: 61
cgtttaggca ggtagctaag                                              20

<210> SEQ ID NO 62
<211> LENGTH: 20
<212> TYPE: DNA
<213> ORGANISM: Artificial
<220> FEATURE:
<223> OTHER INFORMATION: synthetic

<400> SEQUENCE: 62
cctcacagca tcatcacgtg                                              20
```

```
<210> SEQ ID NO 63
<211> LENGTH: 20
<212> TYPE: DNA
<213> ORGANISM: Artificial
<220> FEATURE:
<223> OTHER INFORMATION: synthetic

<400> SEQUENCE: 63
tcacgctgat gataccatca                                               20

<210> SEQ ID NO 64
<211> LENGTH: 20
<212> TYPE: DNA
<213> ORGANISM: Artificial
<220> FEATURE:
<223> OTHER INFORMATION: synthetic

<400> SEQUENCE: 64
agcaaggggg tttctgttgg                                               20

<210> SEQ ID NO 65
<211> LENGTH: 20
<212> TYPE: DNA
<213> ORGANISM: Artificial
<220> FEATURE:
<223> OTHER INFORMATION: synthetic

<400> SEQUENCE: 65
ccagacatct ggatgtcagt                                               20

<210> SEQ ID NO 66
<211> LENGTH: 20
<212> TYPE: DNA
<213> ORGANISM: Artificial
<220> FEATURE:
<223> OTHER INFORMATION: synthetic

<400> SEQUENCE: 66
gagagatgct gcatgctttg                                               20

<210> SEQ ID NO 67
<211> LENGTH: 20
<212> TYPE: DNA
<213> ORGANISM: Artificial
<220> FEATURE:
<223> OTHER INFORMATION: synthetic

<400> SEQUENCE: 67
tgaagcactt cttcacaagg                                               20

<210> SEQ ID NO 68
<211> LENGTH: 20
<212> TYPE: DNA
<213> ORGANISM: Artificial
<220> FEATURE:
<223> OTHER INFORMATION: synthetic

<400> SEQUENCE: 68
gctacctcat ccgtgagagc                                               20

<210> SEQ ID NO 69
<211> LENGTH: 20
<212> TYPE: DNA
<213> ORGANISM: Artificial
<220> FEATURE:
<223> OTHER INFORMATION: synthetic

<400> SEQUENCE: 69
```
cccaacaaag tgctttccat                                              20

<210> SEQ ID NO 70
<211> LENGTH: 20
<212> TYPE: DNA
<213> ORGANISM: Artificial
<220> FEATURE:
<223> OTHER INFORMATION: synthetic

<400> SEQUENCE: 70
agggctttcc ttgctgtgtc                                              20

<210> SEQ ID NO 71
<211> LENGTH: 20
<212> TYPE: DNA
<213> ORGANISM: Artificial
<220> FEATURE:
<223> OTHER INFORMATION: synthetic

<400> SEQUENCE: 71
taggtccctt ctcatgaacc                                              20

<210> SEQ ID NO 72
<211> LENGTH: 21
<212> TYPE: DNA
<213> ORGANISM: Artificial
<220> FEATURE:
<223> OTHER INFORMATION: synthetic

<400> SEQUENCE: 72
gttgacatca cttgttagaa g                                            21

<210> SEQ ID NO 73
<211> LENGTH: 76
<212> TYPE: DNA
<213> ORGANISM: Artificial
<220> FEATURE:
<223> OTHER INFORMATION: synthetic

<400> SEQUENCE: 73
tcaaaggcat ccaaagatga gcctgtaaca ctgcacactc caagcactga gcattccctt     60
gaccaagttg ctgaag                                                  76

<210> SEQ ID NO 74
<211> LENGTH: 20
<212> TYPE: DNA
<213> ORGANISM: Artificial
<220> FEATURE:
<223> OTHER INFORMATION: synthetic

<400> SEQUENCE: 74
agggctttcc ttgctgtgtc                                              20

<210> SEQ ID NO 75
<211> LENGTH: 20
<212> TYPE: DNA
<213> ORGANISM: Artificial
<220> FEATURE:
<223> OTHER INFORMATION: synthetic

<400> SEQUENCE: 75
acgtctcctg acaccattcc                                              20

<210> SEQ ID NO 76
<211> LENGTH: 20

```
<212> TYPE: DNA
<213> ORGANISM: Artificial
<220> FEATURE:
<223> OTHER INFORMATION: synthetic

<400> SEQUENCE: 76
ggagttccag ctccattgtg                                              20

<210> SEQ ID NO 77
<211> LENGTH: 20
<212> TYPE: DNA
<213> ORGANISM: Artificial
<220> FEATURE:
<223> OTHER INFORMATION: synthetic

<400> SEQUENCE: 77
accatgacag tgagctttcc                                              20

<210> SEQ ID NO 78
<211> LENGTH: 20
<212> TYPE: DNA
<213> ORGANISM: Artificial
<220> FEATURE:
<223> OTHER INFORMATION: synthetic

<400> SEQUENCE: 78
cttcacgaag cactgagatc                                              20

<210> SEQ ID NO 79
<211> LENGTH: 20
<212> TYPE: DNA
<213> ORGANISM: Artificial
<220> FEATURE:
<223> OTHER INFORMATION: synthetic

<400> SEQUENCE: 79
aggttctctg cactcatcag                                              20

<210> SEQ ID NO 80
<211> LENGTH: 33
<212> TYPE: DNA
<213> ORGANISM: Artificial
<220> FEATURE:
<223> OTHER INFORMATION: synthetic

<400> SEQUENCE: 80
tgagctctag aagctgggat tttctatttc atc                               33

<210> SEQ ID NO 81
<211> LENGTH: 33
<212> TYPE: DNA
<213> ORGANISM: Artificial
<220> FEATURE:
<223> OTHER INFORMATION: synthetic

<400> SEQUENCE: 81
tgcggccgct cagacaggaa ccatcctgcc atg                               33

<210> SEQ ID NO 82
<211> LENGTH: 23
<212> TYPE: DNA
<213> ORGANISM: Artificial
<220> FEATURE:
<223> OTHER INFORMATION: synthetic

<400> SEQUENCE: 82
ccatggctgg gattttctat ttc                                          23
```

```
<210> SEQ ID NO 83
<211> LENGTH: 23
<212> TYPE: DNA
<213> ORGANISM: Artificial
<220> FEATURE:
<223> OTHER INFORMATION: synthetic

<400> SEQUENCE: 83
aagttctaac accttgattc aaa                                            23

<210> SEQ ID NO 84
<211> LENGTH: 33
<212> TYPE: DNA
<213> ORGANISM: Artificial
<220> FEATURE:
<223> OTHER INFORMATION: synthetic

<400> SEQUENCE: 84
tgagctctag aagctgggat tttctatttc atc                                 33

<210> SEQ ID NO 85
<211> LENGTH: 33
<212> TYPE: DNA
<213> ORGANISM: Artificial
<220> FEATURE:
<223> OTHER INFORMATION: synthetic

<400> SEQUENCE: 85
aagggatcca caaagttct aacaccttga ttc                                  33

<210> SEQ ID NO 86
<211> LENGTH: 21
<212> TYPE: DNA
<213> ORGANISM: Artificial
<220> FEATURE:
<223> OTHER INFORMATION: synthetic

<400> SEQUENCE: 86
cgaagacccc aaccaggcag t                                              21

<210> SEQ ID NO 87
<211> LENGTH: 21
<212> TYPE: DNA
<213> ORGANISM: Artificial
<220> FEATURE:
<223> OTHER INFORMATION: synthetic

<400> SEQUENCE: 87
gctcagacag gaaccatcct g                                              21

<210> SEQ ID NO 88
<211> LENGTH: 37
<212> TYPE: DNA
<213> ORGANISM: Artificial
<220> FEATURE:
<223> OTHER INFORMATION: synthetic

<400> SEQUENCE: 88
gtggatccct ttacattcga agacccaac caggcag                              37

<210> SEQ ID NO 89
<211> LENGTH: 33
<212> TYPE: DNA
<213> ORGANISM: Artificial
<220> FEATURE:
<223> OTHER INFORMATION: synthetic
```

```
<400> SEQUENCE: 89
tgcggccgct cagacaggaa ccatcctgcc atg                                33

<210> SEQ ID NO 90
<211> LENGTH: 64
<212> TYPE: DNA
<213> ORGANISM: Artificial
<220> FEATURE:
<223> OTHER INFORMATION: synthetic

<400> SEQUENCE: 90
tcgaggcttc ctctcatcac ctacgattca agagatcgta ggtgatgaga ggaattttt   60 ggaa                                                               64

<210> SEQ ID NO 91
<211> LENGTH: 64
<212> TYPE: DNA
<213> ORGANISM: Artificial
<220> FEATURE:
<223> OTHER INFORMATION: synthetic

<400> SEQUENCE: 91
ctagaaggtt ttttaaggag agtagtggat gctagagaac ttagcatcca ctactctcct   60
tcgg                                                               64

<210> SEQ ID NO 92
<211> LENGTH: 64
<212> TYPE: DNA
<213> ORGANISM: Artificial
<220> FEATURE:
<223> OTHER INFORMATION: synthetic

<400> SEQUENCE: 92
tcgaggcttc agtacatcct cctccattca agagatggag gaggatgtac tgaattttt   60 ggaa                                                               64

<210> SEQ ID NO 93
<211> LENGTH: 64
<212> TYPE: DNA
<213> ORGANISM: Artificial
<220> FEATURE:
<223> OTHER INFORMATION: synthetic

<400> SEQUENCE: 93
ctagaaggtt ttttaagtca tgtaggagga ggtagagaac ttacctcctc ctacatgact   60
tcgg                                                               64

<210> SEQ ID NO 94
<211> LENGTH: 1263
<212> TYPE: DNA
<213> ORGANISM: Mus musculus

<400> SEQUENCE: 94
gagagatgct gcatgctttg tatggtagca cagactgatt tcctctgcag actcttaagt   60
tttcagaagc ttaaatatag agccctgtta taaaggaag agagaatttg tgtgttaaat   120
cggccttgtg aagaagtgct tcatcactct cctgcacctc cctgtgctct ggtgcgtggc   180
gtggccacgg ctctctaggt tagggctcgg agctggctgc agcatgctca tgtgctagct   240
gagtagagtt caccggcagt cgcaggctga cacagggttt tttggttttt gtctttctat   300
tccgttgaat atcagaatgc catccaaaga gtcttggtcg gggaggaaag ctaacagagc   360
```

```
cacagtccac aaagcaaaac ccgagggccg gcagcaaggc ttactgatag cagccttggg      420
aatgaaactg ggctctcaaa agtcatctgt gacaatctgg caacctctga aactctttgc      480
ttattcgcag ttgacatcac ttgttagaag agcaactctg aaagaaaatg aacaaattcc      540
aaaatatgaa aaggttcaca atttcaaggt gcatacgttc cgagggccac actggtgtga      600
atactgtgcc aacttcatgt ggggcctcat tgctcaggga gtgaaatgtg caggtcttaa      660
ttctgaagga ctctaccgag tgtcaggatt tagtgacctg attgaagatg tcaagatggc      720
ttttgataga gatggtgaga aggcggatat ttctgtgaac atgtatgagg acatcaacat      780
tatcactggt gcacttaaac tgtacttcag ggatctgcca attcctctca tcacatacga      840
tgcctacccc aagttcattg agtctgccaa aattatggac cctgacgagc aattggagac      900
ccttcacgaa gcactgagat cgctgccgcc tgcccactgc gagacgctcc ggtacctcat      960
ggcgcatctc aagagagtga cccttcatga aaggagaat ctgatgagtg cagagaacct     1020
tgggatcgtg tttggaccaa ccctcatgag atccccagag ctcgacccca tggccgccct     1080
gaacgacata cgctatcaga gactggtggt ggagctgctt atcaaaaacg aagacatttt     1140
attttagagt tttgatttga ggagaagaaa atggtttac agatgaagga atgttttcta     1200
gtaatttaat tagcttcatt agctgaattg tttcttcgtt agaggtttgg ccaaataccc     1260
aga                                                                   1263

<210> SEQ ID NO 95
<211> LENGTH: 1324
<212> TYPE: DNA
<213> ORGANISM: Mus musculus

<400> SEQUENCE: 95
ccatggctct gaccctgttc gatacagatg aatatagacc tcctgtttgg aaatcttact       60
tataccagct gcagcaggaa gcccctcacc ctcgaagggt cacctgcact tgtgaggtag      120
aaaacagacc aaagtattat ggaagagagt atcatggcat gatctctaga aagagactg      180 accagctcct gagtgtggct gaggggagct acctcatccg tgagagccag cggcagccag      240
gaacgtacac tttggcttta agatttggaa gtcagaccag aaacttcagg ctgtactacg      300
atggaaagca ctttgttggg gagaaacgct ttgagtccat ccacgatctg gtgactgatg      360
gcttgattac tctctatatt gaaaccaagg cagcagaata cattgccaag atgacgataa      420
acccaattta tgagcacata ggatacacaa ccttaaacag agagccagca tacaaacagc      480
acatggcagt cctgaaagag acacatgatg agaaagaggc tacaggccag gatggggtat      540
cagagaaaag gttgacatca cttgttagaa gagcaactct gaaagaaaat gaacaaattc      600
caaaatatga aaaggttcac aatttcaagg tgcatacgtt ccgagggcca cactggtgtg      660
aatactgtgc caacttcatg tggggcctca ttgctcaggg agtgaaatgt gcaggtctta      720
attctgaagg actctaccga gtgtcaggat ttagtgacct gattgaagat gtcaagatgg      780
cttttgatag agatggtgag aaggcggata tttctgtgaa catgtatgag gacatcaaca      840
ttatcactgg tgcacttaaa ctgtacttca gggatctgcc aattcctctc atcacatacg      900
atgcctaccc caagttcatt gagtctgcca aaattatgga ccctgacgag caattggaga      960
cccttcacga agcactgaga tcgctgccgc ctgcccactg cgagacgctc cggtacctca     1020
tggcgcatct caagagagtg acccttcatg agaaggagaa tctgatgagt gcagagaacc     1080
ttgggatcgt gtttggacca accctcatga gatccccaga gctcgacccc atggccgccc     1140
tgaacgacat acgctatcag agactggtgg tggagctgct tatcaaaaac gaagacattt     1200
```

| | |
|---|---|
| tattttagag ttttgatttg aggagaagaa aaatggttta cagatgaagg aatgttttct | 1260 |
| agtaatttaa ttagcttcat tagctgaatt gtttcttcgt tagaggtttg gccaaatacc | 1320 |
| caga | 1324 |

<210> SEQ ID NO 96
<211> LENGTH: 3970
<212> TYPE: DNA
<213> ORGANISM: Mus musculus

<400> SEQUENCE: 96

| | |
|---|---|
| agggctttcc ttgctgtgtc ccccaggcag aaggtggaac gtcaggagaa ggcagaagag | 60 |
| aaaaccctct cccttaggcc tcttcatagc accattgacc ggttcatgag aagggaccta | 120 |
| acaccttcca gaaggcctca cctctcagta tgtcataaga attatgaaga aaacagactc | 180 |
| agatcttagc attggtgatg tgacattcta ttatgtgtaa ttatttaaca cttaatagtt | 240 |
| tttgtgtagg gaatccatca tttgattttg ttttgctttc tggggtcat ttaggaactt | 300 |
| aaataatgaa gcactaacca gaatcctagc cttgttgggt gtgatggcac atgcctttaa | 360 |
| ttgcagcatt cagagggcaa tgactggcag atatctagag gccaacctgg tctatgtaga | 420 |
| gagttctggg tcagccaggg ctacatagtg agaccctatc tcaaaaagaa agaaaatcct | 480 |
| gtcctagctc taatcaaact ctcccaagag gagagagctg atgttcctct ccttggagga | 540 |
| gctgcacttc tgctgaaaga aacactccag aaagcccagg ctggaaatag tcacgacttt | 600 |
| tccttcattc ttttcacaga ttgtgggttg aatgttcaca agcagtgttc caattgtctt | 660 |
| agtcagggtt tctattcctg cacaaacatc atgaccaaga agcaagttgg ggaggaaagg | 720 |
| gtttattcgg cttacacttc catactgctg ttcatcacca aggaagccag gactggaact | 780 |
| caagcaggtc aggaaacagg agctgatgca gaggccatgg agggatgttc tttactggct | 840 |
| tgcctcccct ggcttgctca gcctgctctc ttataaaacc caagactacc agccagggat | 900 |
| ggtctcaccc acaaggggcc tttccccctt gatcactaat tgagaaaatg ccttacagtt | 960 |
| ggatctcatg gaggcatttc tcaacagaa gctcctttct ctgtgataac tccagctgtg | 1020 |
| tcaagttgac acaaaattag ccagtacaat tgaccccttg tcaacttgac acacaaaaac | 1080 |
| atcactagta agcctcaacc cttacaatct tattcatccc caagatctaa ataactttaa | 1140 |
| aagtcccaca gcctttacat attcttaaaa tttcaatctc tttaaaatat ccatctcttt | 1200 |
| taaaatccaa agtcttttta caattaaaag tctcttaact gtgggctcca ctaaaacagt | 1260 |
| ttcttccttc aagagggaaa atatcagggc acagtcacaa tcaaaagcaa aagtcaatct | 1320 |
| ccaaccgtcc aatgtctggg atccaactca cgatcttctg ggctcctcca agggcttggg | 1380 |
| taacttctcc agccaggccc tttgtagcac acgcatcgtc ctctaggctc cagatgcctg | 1440 |
| taccccactg ctgctgctgc tcttggtggt catctcatgg tactggcatc tccaaaacac | 1500 |
| tgcatgaccc cttcagtcct gggccttcaa ttgcaactga ggctgcacct tcaccaatgg | 1560 |
| ccttccatgg cctctcacag taccgaacct cagctgcttt gcgtgacccc ttcatgcctt | 1620 |
| caaaaccagt accactgggg tgacccttac atattaccaa gtcccactgc agcaggagta | 1680 |
| catccttggc catctctgga acactgcctc tttgtgcttt cagaaaacac ttcccagaag | 1740 |
| atgtcacctc aatgatgctg gtctcttctt aatcaccgct aatttcttag ctccagctaa | 1800 |
| ccagcatcaa tagtcccagt aatgcaaagt ttttgctttg gtagttctgg tatcttgtta | 1860 |
| atcacagctg attcttcagc cccagctaac cagaactaca gaatcttcac aaacaaaaca | 1920 |
| gcaatggccc tgaaaagagt ctttaatttt tcctctgaaa tttcacaaac cagagctcca | 1980 |

```
tcttctgcag tgttctcaac attatcttcc aagctcctac atgacatccg acagagctct    2040
taacaacgga tggatcttca agcccaaagt tccaaagtcc ttccacagtc ctccccaaaa    2100
catggtcaga ttgtcacagg aatacccccac tctgctggta ccaatttgtc ttagtcaggg   2160
tttctattcc tgcacaaaca tcatgaccaa gaagcaagtt ggggaggaaa gggtttattc    2220
ggcttacact tccatactgc tgttcatcac caaggaagcc aggactggaa ctcaagcagg    2280
tcaggaaaca ggagctgatg cagaggccat ggagggatgt tctttactgg cttgcctccc    2340
ctggcttgct cagcctgctc tcttataaaa cccaagacta ccagccaggg atggtctcac    2400
ccacaagggg cctttccccc ttgatcacta attgagaaaa tgccttacag ttggatctca    2460
tggaggcatt tcctcaacag aagctccttt ctctgtgata actccagctg tgtcaagttg    2520
acacaaaatt agccagtaca gtccccaatg actgtaagcc agatctgaag cacgtgaaga    2580
aggtgtacag ctgtgacctg acaacgctcg tgaaagctca catccaccaag cggccaatgg   2640
tggtagacat gtgcatcagg gagatcgagt ccagaggtga ggtgtttgga cgaaggctgc    2700
cgacgccttc acttggggct ccctaggcgc ttgccttgtc attgatgtgg ggaatggtgt    2760
caggagacgt gtgctctcac agtgcagtgt attaatgagc aagcagcttg atttcaagga    2820
acatttaact ggtgatggaa agtagtattt aggatacatt aatggatggt gtctgcagtc    2880
tgcaaaaatc tctgggcaga gatgtattca cctttcaggt tttaagttct tctcatgcca    2940
ggacaaagac agaaatgccc tattaaaacg tccagagcag aaacctgagc cgcaccctaa    3000
ttattcttgc ccccttggga aaacagccat aggcctgctg atgcaggctt tctgttctgt    3060
aaaagacttt atgatggaat tgggtgatga atggtctccc ttaagattta acattacttg    3120
gtctaattag gcaacatgat ggccaaatta taaatatcca ggtgacagta ggtcagaagt    3180
aaaaattgtg gaacagattc acttttggag gatgtgggag aagacttcta ggcatgtgtg    3240
tttttttctaa cacatcgttt gtccagcttg aagtatggag atgttgaa atgagaagga    3300
aagtcatgag ttaacagaaa agtagttccc atgcttcatt cattcattca ttttttttcag   3360
gtcttaattc tgaaggactc taccgagtgt caggatttag tgacctgatt gaagatgtca    3420
agatggcttt tgatagagat ggtgagaagg cggatatttc tgtgaacatg tatgaggaca    3480
tcaacattat cactggtgca cttaaactgt acttcaggga tctgccaatt cctctcatca    3540
catacgatgc ctaccccaag ttcattgagt ctgccaaaat tatggaccct gacgagcaat    3600
tggagaccct tcacgaagca ctgagatcgc tgccgcctgc ccactgcgag acgtccggt     3660
acctcatggc gcatctcaag agagtgaccc ttcatgagaa ggagaatctg atgagtgcag    3720
agaaccttgg gatcgtgttt ggaccaaccc tcatgagatc cccagagctc daccccatgg   3780
ccgccctgaa cgacatacgc tatcagagac tggtggtgga gctgcttatc aaaaacgaag    3840
acattttatt ttagagtttt gatttgagga gaagaaaat ggtttacaga tgaaggaatg     3900
ttttctagta atttaattag cttcattagc tgaattgttt cttcgttaga ggtttggcca    3960
aatacccaga                                                           3970
```

<210> SEQ ID NO 97
<211> LENGTH: 1403
<212> TYPE: DNA
<213> ORGANISM: Mus musculus

<400> SEQUENCE: 97

```
agggctttcc ttgctgtgtc ccccaggcag aaggtggaac gtcaggagaa ggcagaagag      60
aaaaccctct cccttaggcc tcttcatagc accattgacc ggttcatgag aagggaccta    120
```

```
acaccttcca gaaggcctca cctctcagta tgtcataaga attatgaaga aaacagactc    180
agatcttagc attggtgatg tgacattcta ttatgtgtaa ttatttaaca cttaatagtt    240
tttgtgtagg gaatccatca tttgattttg tttttgcttt ctggggtcat ttaggaactt    300
aaataatgaa gcactaacca gaatcctagc cttgttgggt gtgatggcac atgcctttaa    360
ttgcagcatt cagagggcaa tgactggcag atatctagag gccaacctgg tctatgtaga    420
gagttctggg tcagccaggg ctacatagtg agaccctatc tcaaaagaa agaaaatcct     480 gtcctagctc taatcaaact ctcccaagag gagagagctg atgttcctct ccttggagga    540
gctgcacttc tgctgaaaga aacactccag aaagcccagg ctggaaatag tcacgacttt    600
tccttcattc ttttcacaga ttgtgggttg aatgttcaca agcagtgttc caagatggtc    660
cccaatgact gtaagccaga tctgaagcac gtgaagaagg tgtacagctg tgacctgaca    720
acgctcgtga agctcacat caccaagcgg ccaatggtgg tagacatgtg catcagggag     780
atcgagtcca gaggtcttaa ttctgaagga ctctaccgag tgtcaggatt tagtgacctg    840
attgaagatg tcaagatggc ttttgataga gatggtgaga aggcggatat ttctgtgaac    900
atgtatgagg acatcaacat tatcactggt gcacttaaac tgtacttcag ggatctgcca    960
attcctctca tcacatacga tgcctacccc aagttcattg agtctgccaa aattatggac   1020
cctgacgagc aattggagac ccttcacgaa gcactgagat cgctgccgcc tgcccactgc   1080
gagacgctcc ggtacctcat ggcgcatctc aagagagtga cccttcatga aggagaat     1140 ctgatgagtg cagagaacct tgggatcgtg tttggaccaa ccctcatgag atccccagag   1200
ctcgacccca tggccgccct gaacgacata cgctatcaga gactggtggt ggagctgctt   1260
atcaaaaacg aagacatttt attttagagt tttgatttga ggagaagaaa atggtttac    1320 agatgaagga atgttttcta gtaatttaat tagcttcatt agctgaattg tttcttcgtt   1380
agaggtttgg ccaaataccc aga                                           1403

<210> SEQ ID NO 98
<211> LENGTH: 2770
<212> TYPE: DNA
<213> ORGANISM: Mus musculus

<400> SEQUENCE: 98
agggctttcc ttgctgtgtc ccccaggcag aaggtggaac gtcaggagaa ggcagaagag     60
aaaaccctct cccttaggcc tcttcatagc accattgacc ggttcatgag aagggaccta   120
acaccttcca gaaggcctca cctctcagta tgtcataaga attatgaaga aaacagactc    180
agatcttagc attggtgatg tgacattcta ttatgtgtaa ttatttaaca cttaatagtt    240
tttgtgtagg gaatccatca tttgattttg tttttgcttt ctggggtcat ttaggaactt    300
aaataatgaa gcactaacca gaatcctagc cttgttgggt gtgatggcac atgcctttaa    360
ttgcagcatt cagagggcaa tgactggcag atatctagag gccaacctgg tctatgtaga    420
gagttctggg tcagccaggg ctacatagtg agaccctatc tcaaaagaa agaaaatcct     480 gtcctagctc taatcaaact ctcccaagag gagagagctg atgttcctct ccttggagga    540
gctgcacttc tgctgaaaga aacactccag aaagcccagg ctggaaatag tcacgacttt    600
tccttcattc ttttcacaga ttgtgggttg aatgttcaca agcagtgttc caattgtctt    660
agtcagggtt ctattcctg cacaaacatc atgaccaaga agcaagttgg ggaggaaagg     720
gtttattcgg cttacacttc catactgctg ttcatcacca aggaagccag gactggaact    780
caagcaggtc aggaaacagg agctgatgca gaggccatgg agggatgttc tttactggct    840
```

```
tgcctcccct ggcttgctca gcctgctctc ttataaaacc caagactacc agccagggat      900
ggtctcaccc acaaggggcc tttccccctt gatcactaat tgagaaaatg ccttacagtt      960
ggatctcatg gaggcatttc ctcaacagaa gctcctttct ctgtgataac tccagctgtg     1020
tcaagttgac acaaaattag ccagtacaat tgaccccttg tcaacttgac acacaaaaac     1080
atcactagta agcctcaacc cttacaatct tattcatccc caagatctaa ataactttaa     1140
aagtcccaca gcctttacat attcttaaaa tttcaatctc tttaaaatat ccatctcttt     1200
taaaatccaa agtcttttta caattaaaag tctcttaact gtgggctcca ctaaaacagt     1260
ttcttccttc aagagggaaa atatcagggc acagtcacaa tcaaaagcaa aagtcaatct     1320
ccaaccgtcc aatgtctggg atccaactca cgatcttctg ggctcctcca agggcttggg     1380
taacttctcc agccaggccc tttgtagcac acgcatcgtc ctctaggctc cagatgcctg     1440
taccccactg ctgctgctgc tcttggtggt catctcatgg tactggcatc tccaaaacac     1500
tgcatgaccc cttcagtcct gggccttcaa ttgaactga ggctgcacct tcaccaatgg      1560
ccttccatgg cctctcacag taccgaacct cagctgcttt gcgtgacccc ttcatgcctt     1620
caaaaccagt accactgggg tgacccttac atattaccaa gtcccactgc agcaggagta     1680
catccttggc catctctgga acactgcctc tttgtgcttt cagaaaacac ttcccagaag     1740
atgtcacctc aatgatgctg gtctcttctt aatcaccgct aatttcttag ctccagctaa     1800
ccagcatcaa tagtcccagt aatgcaaagt ttttgctttg gtagttctgg tatcctgtta     1860
atcacagctg attcttcagc cccagctaac cagaactaca gaatcttcac aaacaaaaca     1920
gcaatggccc tgaaaagagt ctttaatttt tcctctgaaa tttcacagac cagagctcca     1980
tcttctgcag tgttctcaac attatcttcc aagctcctac atgacatccg acagagctct     2040
taacaacgga tggatcttca agcccaaagt tccaaagtcc ttccacagtc ctccccaaaa     2100
catggtcaga ttgtcacagg aatacccccac tctgctggta ccaatttgtc ttagtcaggg    2160
tttctattcc tgcacaaaca tcatgaccaa gaagcaagtt ggggaggaaa gggtttattc     2220
ggcttacact tccatactgc tgctcatcac caaggaagcc aggactggaa ctcaagcagg     2280
tcaggaaaca ggagctgatg cagaggccat ggagggatgt tctttactgg cttgcctccc     2340
ctggcttgct cagcctgctc tcttataaaa cccaagacta ccagccaggg atggtctcac     2400
ccacaagggg cctttccccc ttgatcacta attgagaaaa tgccttacag ttggatctca     2460
tggaggcatt tcctcaacag aagctccttt ctctgtgata actccagctg tgtcaagttg     2520
acacaaaatt agccagtaca gtccccaatg actgtaagcc agatctgaag cacgtgaaga     2580
aggtgtacag ctgtgacctg acaacgctcg tgaaagctca catcaccaag cggccaatgg     2640
tggtagacat gtgcatcagg gagatcgagt ccagaggtga ggtgtttgga cgaaggctgc     2700
cgacgccttc acttggggct ccctaggcgc ttgccttgtc attgatgtgg ggaatggtgt     2760
caggagacgt                                                            2770
```

<210> SEQ ID NO 99
<211> LENGTH: 2607
<212> TYPE: DNA
<213> ORGANISM: Homo sapiens

<400> SEQUENCE: 99

```
gagctcgtgg gagacgctat cgcaagatgg cgtctgcgag gccgcgggat gcggagtgag       60
```

-continued

```
cgcgccccgc gggggctgt gcgaggctgc tgctgctctc cccgtcgccg ccgccgccgc    120
cgccagtgcg gcgccgcctc tccgccagcc actgcgccgc ggccaagcct cctgcctcgc    180
aggtacctcc tcccgcgcgc acgctccgcg cctgatggca gcgacaagtg ccggctcgcg    240
gagagctagc ggggctccct gggccccggtg cgcccgacaa taacgcgtga ataactttt     300 cttgcagcgg tccccgcgt cccggcctgc agcctccccg ggcgccggcg ccccagcac      360 gccccatcgg gcaccccact ctctccgagg tgtgggtgcg gcgggctgat gaggtgatcc    420
ctagcccgcc tgggaggagc gcctggactc gcgggcggcg gcgagcgcct ttacaatggc    480
cctgacccct tttgatacag atgaatatag acctcctgtt tggaaatctt acttatatca    540
gctacaacag gaagcccctc atcctcgaag aattacctgt acttgcgagg tggaaaacag    600
accaaagtat tatggaagag agtttcatgg catgatctcc agagaagcag ccgaccagct    660
cttgattgtg gctgagggga gctacctcat ccgggagagc cagcggcagc cagggaccta    720
cactttggct ttaagatttg gaagtcaaac cagaaacttc aggctctact acgatggcaa    780
gcactttgtt ggggagaaac gctttgagtc catccacgat ctggtgactg atggcttgat    840
tactctctat attgaaacca aggcagcaga atacattgcc aagatgacga taaacccaat    900
ttatgagcac gtaggataca caaccttaaa cagagagcca gcatacaaaa aacatatgcc    960
agtcctgaaa gagacacatg atgagagaga ttctacaggc caggatgggg tgtcagagaa   1020
aaggttgaca tcacttgtta gaagagcaac tctgaaagaa aacgagcaaa ttccaaaata   1080
tgaaaagatt cacaatttca aggtgcatac attcagaggg ccacactggt gtgaatactg   1140
tgccaacttt atgtggggtc tcattgctca gggagtgaaa tgtgcagatt gtggtttgaa   1200
tgttcataag cagtgttcca agatggtccc aaatgactgt aagccagact gaagcatgt    1260 caaaaggtg tacagctgtg accttacgac gctcgtgaaa gcacatacca ctaagcggcc    1320
aatggtggta gacatgtgca tcagggagat tgagtctaga ggtcttaatt ctgaaggact   1380
ataccgagta tcaggattta gtgacctaat tgaagatgtc aagatggctt tcgacagaga   1440
tggtgagaag gcagatattt ctgtgaacat gtatgaagat atcaacatta tcactggtgc   1500
acttaaactg tacttcaggg atttgccaat tccactcatt acatatgatg cctaccctaa   1560
gtttatagaa tctgccaaaa ttatggatcc ggatgagcaa ttggaaaccc ttcatgaagc   1620
actgaaacta ctgccacctg ctcactgcga aaccctccgg tacctcatgg cacatctaaa   1680
gagagtgacc ctccacgaaa aggagaatct tatgaatgca gagaaccttg aatcgtctt    1740 tggacccacc cttatgagat ctccagaact agacgccatg gctgcattga atgatatacg   1800
gtatcagaga ctggtggtgg agctgcttat caaaaacgaa gacatttat ttaaatttt     1860 taatttgagg ggaaaagaaa tgttttacag atgaaggaat gttttatagt aatttaattt   1920
gctcctgtag ctgcattatt tcttgattag aggtttgggc atataaccag attaaagtga   1980
aggaactttc tgttgttttt gtagcaccgc tcagctgtct tgtaaaacag tgaacacacg   2040
ctttctggtt ctagtaatcc tgggtgttta tcacgttcag agaaactcaa gctattgcat   2100
gattagcccc ctatctggca aggaaacccc atacagaaga acaacaaac ctgcgcctgc    2160 accgcctctg cgtcctgggt agtctgtgct tgtaatccag catgtttcac agagtaagcc   2220
tgttgtgact ttgcttttgg ggtctatgtc attggtttct gatgcttgta caaacacgca   2280
cacacaaatg gataaaacag cacctctggc tgttacatta ccataaacca tatcacatgc   2340
ctacatttta caaatgattt ctggtttctc ttagttcttc tctaacatag tactttcttt   2400
ccagcaaaag caaaatgtgt tttcagattt gttactttaa taaaggttat ccataccaat   2460
```

```
aaaaagtgta caacacagca ttttctgtta aattattatt ggttttcagt tgtaatttgg    2520
tattttttct ggcatgcgtt tattaattta ttaaattggc ttttagaaat aaaaaatatt    2580
gatagcttac ttttttctca taagaat                                        2607
```